US007652029B2

(12) United States Patent
Llompart et al.

(10) Patent No.: US 7,652,029 B2
(45) Date of Patent: Jan. 26, 2010

(54) THERAPEUTIC COMPOUND AND TREATMENTS

(75) Inventors: Javier Llompart, Valencia (ES); Jorge Galvez, Valencia (ES); Kollol Pal, Needham, MA (US)

(73) Assignee: Medisyn Technologies, Inc., Minnetonka, MN (US)

( * ) Notice: Subject to any disclaimer, the term of this patent is extended or adjusted under 35 U.S.C. 154(b) by 517 days.

(21) Appl. No.: 11/179,796

(22) Filed: Jul. 11, 2005

(65) Prior Publication Data

US 2006/0014770 A1 Jan. 19, 2006

Related U.S. Application Data

(60) Provisional application No. 60/586,519, filed on Jul. 9, 2004.

(51) Int. Cl.
*A61K 31/4365* (2006.01)
*A61K 31/438* (2006.01)
(52) U.S. Cl. .................................. 514/287; 514/278
(58) Field of Classification Search ................ 514/278, 514/287; 546/15, 18, 65
See application file for complete search history.

(56) References Cited

U.S. PATENT DOCUMENTS

| 6,290,929 | B1 | 9/2001 | Camden |
| 6,352,844 | B1 | 3/2002 | Maurer et al. |
| 6,919,376 | B2 | 7/2005 | Llompart et al. |

OTHER PUBLICATIONS

Medvedeva, S. M., et al. "1,3-Dipolar Cycloaddition of Ethyl Propiolate To 4,4-Dimethyl-4,5-Dihydro-1,2-Dithiolo-[5,4-c]Quinoline-1-1Thiones", Chemistry of Heterocyclic Compounds, vol. 38, No. 8 (2002).
Medvedeva, S. M., et al., "Novel Heterocyclic Systems Based on 8-R-4,5-Dihydro-4,4-Dimethyle-[1,2]Dithiolo[3,4-c]Quinoline-1-1Thiones," Chemistry of Heterocyclic Compounds, vol. 42, No. 4 (2006).
Shikhaliev, Kh.S., et al., "4,4-Dimethyl-4,5-Dihydro-1,2-Dithiolo-[3,4-c]Quinoline-1-Thiones in 1,3-Dipolar Cycloaddition Reactions With Acetylenic Dipolarophiles", Chemistry of Heterocyclic Compounds, vol. 35, No. 5 (1999).
Shikhaliev, Kh. S., et al. "New Heterocyclic Compounds Derived from 8-R-4,4-Dimethyl-2,3-dithiolo-[5,4-c]quinoline-1-thiones", Russian Journal of General Chemistry, vol. 70, No. 3 pp. 450-452 (2000).
Boyd et al., "Some Practical Considerations and Applications of the NCI in vitro Drug Discovery Screen", Drug Dev. Res. 34:91-109 (1995).
Boyd, "The NCI In Vitro Anticancer Drug Discovery Screen, Concept, Implementation, and Operation 1985-1995", Drug Development: Preclinical Screening, Clinical Trials and Approval, (Teicher, ed.) Totowa, NJ, Humana Press, 1997, pp. 23-42.

De Julián-Ortiz, "Prediction of Properties of Chiral Compounds by Molecular Topology", Journal of Molecular Graphics and Modeling, 16:14-18 (1998).
Duart et al., "Optimization of a mathematical topological pattern for the prediction of antihistaminic activity", Journal of Computer-Aided Molecular Design, 15:561-572 (2001).
Gálvez et al., "Charge Indexes. New Topological Descriptors", J. Chem Inf. Comput. Sci., 34(3): 520-525 (1994).
Gálvez et al., "Topological Approach to Analgesia", J. Chem Inf. Comput. Sci., 34(5):1198-1203 (1994).
Gálvez et al., "Topological Approach to Drug Design", J. Chem Inf. Comput. Sci., (35)2:272-284 (1995).
Gálvez et al., "New Cytostatic Agents Obtained by Molecular Topology", Bioorganic & Medicinal Chemistry Letters, 6(19):2301-2306 (1996).
Gálvez, "On a topological interpretation of electronic and vibrational molecular energies", Journal of Molecular Structure (Theochem), 429: 255-264.
Gálvez et al., Pharmacological distribution diagrams: A tool for de novo drug design, Journal of Molecular Graphics, 14:272-276 (1996).
Gozalbes et al., "Prediction of Quinolone Activity against/ Mycobacterium avium by Molecular topology and Virtual Computational Screening", Antimicrobial Agents and Chemotherapy, 44(10):2764-2770 (2000).
Gray et al. "Evaluation of Anchorage-Independent Proliferation in Tumorigenic Cells Using the Redox Dye alamarBlue™", BioTechniques, 21(5):780-781 (1996).
Lahuerta Zamora et al., "Prediction of the Chemiluminescent Behavior of Pharmaceuticals and Pesticides", Analytical Chemistry, 73(17):4301-4306 (2001).
Brown., Reactions of 2,2-Dialkyl-1,2-dihydroquinolines. Part IV. 4,5-Dihydro-4,4-dimethyl-1H-1,2-dithiolo[3,4-c]quinoline-1thiones, J. Chem. Soc.(C), p. 1074 (1968).
De Julián-Ortiz et al., "Virtual Combinatorial Syntheses and Computational Screening of New Potential Anti-Herpes Compounds", J. Med. Chem, 42(17): 3308-3314 (1999).
Graham, "Theoretical Studies Applied To Drug Design: ab initio Electronic Distributions In Bioisosteres", Journal of Molecular Structure (Theochem), 343:105-109 (1995).
Lipinski, "Bioisosterism in Drug Design", Annual Reports in Medicinal Chemistry, Allen, ed., 283-291, 1986.
Llompart et al., Database Hcaplus on STN (Columbus, OH, USA, DN 140:281362, 'N,-N-dicyclohexyl-(IS)-isoborneol-10sulfonamide MT103 family members as anittumor and other therapeutic agents and corresponding treatemnets and compositions, U.S. PSre-Grant Publication 20040325, Mar. 25, 2004 (Abstract).
Ranu et al., "Efficient microwave-assisted synthesis of quinolines and dihydroquinolines under solvent-free conditions", Tetrahedron, 59:813-819 (2003).
Theoclitou et al., "Novel facile synthesis of 2,2,4 substituted 1,2-dihydroquinolines via a modified Skraup reaction", Tetrahedron Letters, 43:3907-3910 (2002).

(Continued)

Primary Examiner—Charanjit S Aulakh
(74) Attorney, Agent, or Firm—Ropes & Gray LLP

(57) ABSTRACT

Compositions and uses associated with the MT477 family of compounds are disclosed. Particular structural features and properties of the compounds are described in detail. Uses include administering an MT477 family member to a patient for therapeutic purposes. Compositions include chemicals belonging to the MT477 family and pharmaceuticals that contain such chemicals.

11 Claims, 15 Drawing Sheets

OTHER PUBLICATIONS

Yun, "Application of Bioisosterism To New Drug Design" *Hwahak Sekye*, 33:576-579 (1993).

Zhao, "Bioisosteric Replacement And Development Of Lead Compounds In Drug Design", Huaxue Tongbao, pp. 34-38 (1995).

Jasinski, et al., "A novel quinoline, MT477: suppresses cell signaling through Ras molecular pathway, inhibits PKC activity, and demonstrates in vivo anti-tumor activity against human carcinoma cell lines", Invest New Drugs, 10637-007-9096 (2007).

Jasinski, et al., "Novel Ras pathway inhibitor induces apoptosis and growth inhibition of K-ras-mutated cancer cells in vitro and in vivo", Translational Research, vol. 152(5), pp. 203-212 (2008).

THERAPEUTIC COMPOUND AND TREATMENTS

CROSS REFERENCE TO RELATED APPLICATIONS

This application claims priority to U.S. Patent Ser. No. 60/586,519 filed Jul. 9, 2004, entitled "THERAPEUTIC AGENTS AND CORRESPONDING TREATMENTS", which is hereby incorporated by reference herein.

FIELD OF THE INVENTION

The application is generally related to methods of treating patients with chemical agents, and methods of inhibiting cell growth, including cancer.

BACKGROUND OF THE INVENTION

Cancer is a disease that afflicts many people and is a leading cause of death in humans and non-human animals. Cancers typically involve cells that grow by uncontrolled growth of the cells that creates many new cells. Many anti-cancer drugs are agents that inhibit or stop cell growth.

Many anti-cancer drugs are known to be effective against cancers and tumor cells, but some cancers and tumors respond poorly to these drugs. Further, many anti-cancer drugs also destroy other cells in the body. Thus, new anti-cancer drugs are desired, and drugs that are able to target specific cancer types can provide useful therapeutic options.

Agents that inhibit cell growth are useful as anti-cancer drugs. The National Cancer Institute (NCI) is an agency of the United States government that is involved in the testing of anti-cancer drugs. NCI often conducts initial screening tests of potential anti-cancer drugs using a three cell line test. Each of the three cell lines is a type of cancerous cell. The cells are exposed to the drug candidates, and the drugs' effectiveness in stopping cell growth and/or killing the cells is measured.

The NCI typically tests the most promising drugs with a further battery of approximately about 60 cell lines, which is referred to conventionally as the 60-cell line test, and the dose of the drug that is required to stop cell growth and to kill cells is measured. The dose of the drug that is required to inhibit approximately 50% of the growth of a cancer cell is reported as the $GI_{50}$ concentration of the drug. The lower the $GI_{50}$, the more effective is the anti-cancer drug. The $GI_{50}$ is sometimes reported in the units of $-\log(GI_{50})$, so that the higher the value for $-\log(GI_{50})$, the more effective is the anti-cancer drug. The dose of the drug that is required to stop approximately 100% of cell growth is reported as the total growth inhibition (TGI) concentration of the drug. The dose of the drug that is required to reduce the number of the cells to 50% of the original number of cells is referred to as the $LC_{50}$ concentration. The lower the TGI or $LC_{50}$, the more potent is the anti-cancer drug.

SUMMARY OF THE INVENTION

The invention includes embodiments related to the MT477 family of therapeutic compounds, as shown for example, in Formulas 1(a) and 1(b), below. Tests, reported herein, show that MT477 is more effective than a leading cancer drug, cisplatin, in many applications. An embodiment of the invention is a method of using an MT477 family member for treatment of patients, for example, as a cancer therapeutic, apoptosis agent, and protein kinase agent. Another embodiment is using a MT477 family member as a therapeutic, antibacterial, antifungal, apoptosis agent, protein kinase agent, and/or hormonal antagonist. Another embodiment is a therapeutic, apoptosis agent, protein kinase agent, and/or hormonal antagonist that comprises an MT477 family member, e.g., a chemical according to one of Formulas 1-35 below. Embodiments of the invention include compositions and methods for treating a patient, including providing to, or administering to, a patient a therapeutically effective amount of a composition comprising a chemical as in Formulas 1-35.

Another embodiment is a chemical according to one of Formulas 1-35 below, or a species thereof. Another is embodiment is a pharmaceutical composition associated with a chemical according to one of Formulas 1-35 below, or a species thereof. Another embodiment is a method that includes exposing a cell to a composition comprising a chemical according to one of Formulas 1-35 below, or a species thereof, e.g., for diagnosis, testing, screening, or treatment in vitro or in vivo.

DETAILED DESCRIPTION OF THE PREFERRED EMBODIMENTS

Figure 1:
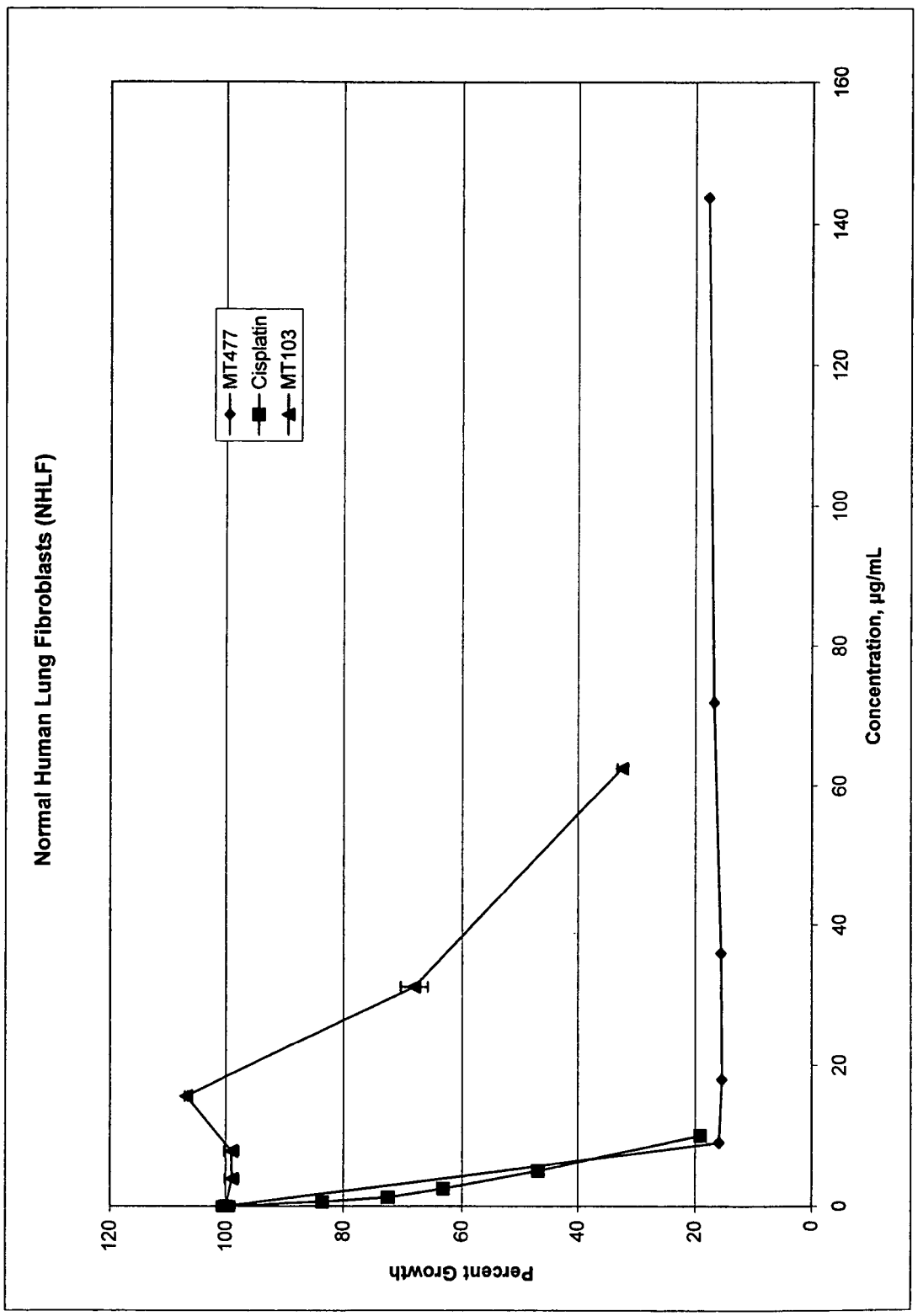
FIG. 1 is a graph of the growth response of normal human lung fibroblasts exposed to various concentrations of MT477, MT103, and cisplatin.

An anti-cancer agent referred to herein as MT477 is disclosed (Formula 2(a)), along with derivatives of this molecule expected to have an anti-cancer activity. These compounds were developed using computer models that analyze topological features of molecules and help to predict which ones will be effective. The predictive power of these processes have been verified by successful in vitro and in vivo tests of candidate compounds, including those set forth in the Examples. Variations of the MT477 molecule are described herein that have structural similarity to MT477 that is expected to give them anti-cancer properties.

The creation of new anti-cancer drugs is a challenging process. An important step is the selection of drug candidates for initial screening. Many approaches for selecting these drug candidates are used. One approach is to use computer modeling to design molecules that have physicochemical properties that are useful as anti-cancer agents.

Computer Modeling

A topological computer modeling program that incorporates a molecular shape learning system has been used to identify the new family of drugs exemplified by MT477. The modeling program takes topological information about chemicals that are known to be effective anti-cancer drugs, and in a next step identifies common topological features that the drugs should share to show activity in the property under study. Then the program identifies new chemicals that have the common topological features. The program is designed not only to identify chemicals that are anti-cancer compounds but also to identify chemicals that are useful to combat specific types of cancer. MT477 was identified by the program as a chemical that would inhibit the growth of cancer cells. Further, MT477 was identified as a compound having particular efficacy against non-small lung cancer cells. The fact that a compound was successfully identified with that function is proof of the efficacy and utility of the compounds predicted by the computer model.

The computer modeling approach relies on molecular topology to determine physicochemical properties of molecules. The topological approach relies on mathematical means to describe and construct descriptive computer models. Through these models, it is possible to forward engineer specific structural activity relations of a molecular charge density alone or in response to adjacent electrotopological features. The topological approach accounts for the true structural invariant of a molecule that is not affected by vibrational or conformational changes. Aspects of this approach are set forth by Galvez in J. Gálvez et al., *J. Chem Inf. Comput. Sci.*, Vol. 34, No. 3, 1994; J. Gálvez et al., *J. Chem Inf. Comput. Sci.*, Vol. 34, No. 5, 1994; J. Gálvez et al., *J. Chem Inf. Comput. Sci.*, Vol. 35, No. 2, 1995; J. Gálvez et al., *Bioorganic & Medicinal Chemistry Letters*, Vol. 6, No. 19, 1996; J. Gálvez et al., *Journal of Molecular Graphics*, Vol. 14, 1996; J. Gálvez, *Journal of Molecular Structure* (Theochem), Vol. 429, 1998; J. V. de Julián-Ortiz, *Journal of Molecular Graphics and Modeling*, Vol. 16, 1998; Jesus V. de Julián-Ortiz et al., *Journal of Medicinal Chemistry*, Vol. 42, No. 17; Rafael Gozalbes et al., *Antimicrobial Agents and Chemotherapy*, Vol. 44, No. 10, October 2000; M. J. Duart et al., *Journal of Computer-Aided Molecular Design*, Vol. 15, 2001; L. Lahuerta Zamora et al., *Analytical Chemistry*, Vol. 73, No. 17, Sep. 1, 2001.

Trained models predict the bioactive topology of molecules and can be readily interpreted to guide the design of new active compounds. This approach combines three advances: a representation that characterizes surface shape such that structurally diverse molecules exhibiting similar surface characteristics are treated as similar; a new machine learning methodology that can accept multiple orientations and conformations of both active and inactive molecules; and an iterative process that applies intermediate models to generate new molecular orientations to produce better predictive models. Two aspects of the program described above, the method of iterative reposing objects to produce better models and the method of training a model when each object has multiple representations, are applicable not only to biological activity modeling but also to other physicochemical characteristics.

The efficacy of the compounds generated by the topological computer modeling program can be confirmed using routine screening by using known cancer cell lines. Cell lines are available from NCI, American Tissue Type Culture, or other laboratories. The NCI has assembled a three cell-line test and the 60 cell-line test for identifying anti-cancer drugs (see M. R. Boyd and K. D. Paul, Some Practical Considerations and Applications of the NCI in vitro Drug Discovery Screen, Drug Dev. Res. 34:91109, 1995; M. R. Boyd, The NCI In Vitro Anticancer Drug Discovery Screen, Concept, Implementation, and Operation 1985-1995, In Drug Development: Preclinical Screening, Clinical trials and Approval, (Teicher, ed.) Totowa, N.J., Humana Press, 1997, pp. 23-42.

These same computer models successfully predicted the efficacy of a compound referred to as MT103. Detailed testing information with respect to MT103 is provided in U.S. Pat. No. 6,919,376. Herein, MT477 was compared with MT103 as a benchmark of MT477's activity.

Cisplatin was also compared, herein, to MT477. Cisplatin has been one of the most widely prescribed and effective treatments for many cancers. Cisplatin is used to treat many types of cancer, and is widely prescribed for testicular, ovarian, bladder, lung, and stomach cancers. Without being bound to a particular theory, cisplatin is believed to kill cancer cells by binding to DNA and interfering with the cell's repair mechanism, which eventually leads to cell death.

As reported herein, MT477 is generally more effective and less toxic than Cisplatin. The following examples show that the MT477 family of compounds is effective general anti-cancer agents.

Terminology

The term heterocyclic is used herein, meaning a cyclic compound having as a ring member at least two different elements. Cyclic compounds may be aromatic or non-aromatic with at least one ring, e.g., one, two, three, or more rings. Cyclic compounds may be poly cyclic meaning that the each ring shares at least one member with the other rings, e.g., a bicyclic ring with two common members, bicyclic ring with one common member, a tricyclic group having two rings that each share two members with a center ring, or a tricyclic group with three rings that each share at least one member with each other. An aromatic group can be any conjugated ring system containing $4n+2$ π-electrons. There are many criteria available for determining aromaticity. A widely employed criterion for the quantitative assessment of aromaticity is the resonance energy. In some embodiments, the resonance energy of the aromatic group is at least 10 KJ/mol.

In further embodiments, the resonance energy of the aromatic group is greater than 0 KJ/mol. Aromatic groups may be classified as an aromatic heterocyclic group which contains at least a heteroatom in the 4n+2 π-electron ring, or as an arene or aryl group which does not contain a heteroatom in the 4n+2 π-electron ring. Nonetheless, either the aromatic heterocyclic or the arene or aryl group may have at least one heteroatom in a substituent attached to the 4n+2 π-electron ring. Furthermore, either the aromatic heterocyclic or the arene or aryl group may comprise a monocyclic or polycyclic (such as bicyclic, tricyclic, etc.) aromatic ring. An arene is a monocyclic or polycyclic aromatic hydrocarbon; an aryl is formed by removal of a hydrocarbon from a ring carbon atom of an arene.

Non-limiting examples of the aromatic heterocyclic group are furanyl, thiophenyl, pyrrolyl, indolyl, carbazolyl, benzofuranyl, benzothiophenyl, dibenzofuranyl, dibenzothiophenyl, pyridinyl, pyridazinyl, pyrimidinyl, pyrazinyl, triazinyl, tetrazinyl, petazinyl, quinolinyl, isoquinolinyl, cinnolinyl, phthalazinyl, quinazolinyl, quinoxalinyl, naphthyridinyl, pteridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4) dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6 di(10H-10-phenothiazinyl)hexane). The linking group may include an aliphatic group, an aromatic group, a heterocyclic group, or a combination thereof. Furthermore, either an aliphatic group or an aromatic group within a linking group may comprise at least one heteroatom such as O, S, and N. Non-limiting examples of the aryl group are phenyl, naphthyl, benzyl, or tolyl group, sexiphenylene, phenanthrenyl, anthracenyl, coronenyl, and tolanylphenyl. The aryl group may also include any combination of the above aryl groups bonded together either by a bond (as in biphenyl group) or by a linking group (as in stilbenyl, diphenyl sulfone, an arylamine group). The linking group may include an aliphatic group, an aromatic group, a heterocyclic group, or a combination thereof. Furthermore, either an aliphatic group or an aromatic group within a linking group may comprise at least one heteroatom such as O, S, and N. The term arylamine group includes an (N,N-disubstituted)arylamine group (e.g., diphenylamine, ethylphenylamine, and diethylamine group), a julolidinyl group, and a carbazolyl group.

An alicyclic compound is a cyclic aliphatic compound having at least one ring, e.g., one, two, three, or more rings. The term aliphatic compound refers to an organic compound that is an alkane or alkene or alkyne or their derivative. Examples of alicyclic compounds include cycloalkanes, e.g., cyclobutane, cyclopentane, cyclohexane, cyclooctane, and bicyclo [2.2.1] heptane group. A heterocyclic non-aromatic compound is a compound having at least one ring and at least two different elements in the ring, e.g., an N, O, or S substituted into at least one ring carbon of cylcohexane, cyclooctane, or bicyclo [2.2.1] heptane group.

The term alkyl, unless otherwise specified, refers to a saturated straight, branched, or cyclic hydrocarbon, and specifically includes, e.g., methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The alkyl group can be optionally substituted with any appropriate group, including but not limited to one or more groups selected from halo, hydroxyl, amino, alkylamino, arylarmino, alkoxy, aryloxy, nitro, cyano, sulfonic acid, sulfate, phosphonic acid, phosphate, or phosphonate, either unprotected, or protected as necessary, as known to those skilled in the art. The term alkenyl, unless otherwise specified, is a straight, branched, or cyclic (in the case of $C_{5-6}$) hydrocarbon with at least one double bond, and may be substituted as described above. The term alkynyl, unless otherwise specified, is a hydrocarbon, straight or branched, with at least one triple bond, and may be substituted as described above. In some embodiments, it is useful to limit the size of these substituents to, e.g., less than about 150, less than about 100, less than about 50, or less than about 20 atoms.

Substituent Groups and Substitution

Substitution is liberally allowed on the chemical groups, and on the atoms that occupy a position in a Formula depicted herein, for various physical effects on the properties of the compounds, such as mobility, sensitivity, solubility, compatibility, stability, and the like, as is known generally in the art. In the description of chemical substituents, there are certain practices common to the art that are reflected in the use of language. The term group indicates that the generically recited chemical entity (e.g., alkyl group, alkenyl group, aromatic group, epoxy group, arylamine group, aromatic heterocyclic group, aryl group, alicyclic group, aliphatic group, heterocyclic non-aromatic group etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents having heteroatom such as 3-ethoxylpropyl, 4-(N-ethylamino)butyl, 3-hydroxypentyl, 2-thiolhexyl, 1,2,3-tribromopropyl, and the like. However, as is consistent with such nomenclature, no substitution would be included within the term that would alter the fundamental bond structure of the underlying group. For example, where a phenyl group is recited, substitution such as 1-aminophenyl, 2,4-dihydroxyphenyl, 1,3,5-trithiophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution.

Suitable substitutions include, for example, bioisosteres, such as acid bioisosteres and ester bioisosteres. Acid bioisosteres are groups with chemical and physical similarities producing broadly similar biological similarities to a corresponding carboxyl group, as described for example in Lipinski, Annual Reports in Medicinal Chemistry, 1986, 21:p 283, "Bioisosterism in Drug Design;" Yun, Hwahak Sekye, 1993, 33:p576-579, "Application of Bioisosterism To New Drug Design;" Zhao, Huaxue Tongbao, 1995, P34-38, "Bioisosteric Replacement And Development Of Lead Compounds In Drug Design;" and Graham, Theochem, 1995, 343:p105-109, "Theoretical Studies Applied To Drug Design: ab initio Electronic Distributions In Bioisosteres," all of which are incorporated herein by reference. Examples of suitable acid bioisosteres include, for example, —C(=O)—NHOH, —C(=O)—NH—CN, —C(=O)—CH$_2$OH, —C(=O)—CH$_2$SH, —SO$_2$—NHR, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazomlidinyl or heterocyclic phenols, such as 3-hydroxyisoxazolyl and 3-hydroxy-1-methylpyrazolyl. Examples of suitable ester bioisosteres include, for example, —C(=O) SR, —COCH2R, —C(=O)NHR, 1,2,4-oxadiazoles and 1,2, 4-thiadiazoles.

All of these various groups may be optionally derivatized with Substituent Groups. Suitable Substituent Groups that may be present on such a "substituted" group include e.g. halogens such as fluoro, chloro, bromo and iodo; cyano; H, hydroxyl group; ester group; ether group; a carbamate, an oxo acid group, an oxocarbon group, an oxo carboxylic acid group, an oxo group, a ketone group; nitro; azido; sulfhydryl; alkanoyl e.g. $C_{1-6}$ alkanoyl group such as acetyl and the like; carboxamido; alkyl groups, alkenyl and alkynyl groups including groups having one or more unsaturated linkages; alkoxy groups having one or more oxygen linkages; aryloxy such as phenoxy; alkylthio groups; alkylsulfinyl groups; alkylsulfonyl groups; aminoalkyl groups such as groups having one or more N atoms; carbocyclic aryl; aryloxy such as phenoxy; aralkyl having 1 to 3 separate or fused rings; aralkoxy having 1 to 3 separate or fused rings; or a heteroaromatic, heterocyclic, or heteroalicyclic group having 1 to 4 separate or fused rings e.g., with one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl. Other substituents may include groups that include O, S, Se, N, P, Si, C and have between 2 and about 150 atoms. In some embodiments, it is useful to limit the size of any substituent to, e.g., less than about 150, less than about 100, less than about 50, or less than about 20 atoms.

Other suitable Substituent Groups include these and other N-containing compounds e.g, amines, amides, amidium ions, amine imides, amine oxides, aminium ions, aminonitrenes, nitrenes, aminoxides, nitriles, and nitrile imides. Other suitable Substituent Groups include these and other S-containing compounds, e.g., sulfonic acid, sulfate, sulfonates, sulfamic acids, sulfanes, sulfatides, sulfenamides, sulfenes, sulfenic acids, sulfenium ions, sulfenyl groups, sulfenylium ions, sulfenyl nitrenes, sulfenyl radicals, sulfides, sulfilimines, sulfimides, sulfimines, sulfinamides, sulfinamidines, sulfines, sulfinic acids, sulfinic anhydrides, sulfinimines, sulfinylamines, sulfolipids, sulfonamides, sulfonamidines, sulfonediimines, sulfones, sulfonic acids, sulfonic anhydrides, sulfonamides, sulfonium compounds, sulfonphthaleins, sulfonylamines, sulfoxides, sulfoximides, sulfoximines, sulfur diimides, thiols, thioacetals, thioaldehydes, thioaldehyde S-oxides, thioanhydrides, thiocarboxylic acids, thiocyanates, thioethers, thiohemiacetals, thioketones, thioketone S-oxides, thiolates, and thionylamines. Other suitable Substituent Groups include these and other O-containing compounds, e.g., having the form ROH (alcohol), RCOOH (carboxylic acids), RCHO (aldehydes), RR'C=O (ketones), ROR' (ethers), and RCOOR' (esters), with the R denoting a bond or atomic element. Other suitable Substituent Groups include these and other P-containing compounds, e.g., phosphanes, phosphanylidenes, phosphatidic acids, phosphazenes, phosphine oxides, phosphines, phosphinic acids, phosphinidenes, phosphinous acids, phosphoglycerides, phospholipids, phosphonic acids, phosphonitriles, phosphonium compounds, phosphonium ylides, phosphono, phosphonous acids, phosphoramides, and phosphoranes. Carbon is useful for making substituents and the number of carbons in a heteroatomic structure may be, e.g., between 1 and n−1 when between 2 and n atoms are used to form a substituent with, e.g., O, P, S, or N. Suitable substitutions on the substituents named herein include, for example, bioisosteres, such as acid bioisosteres and ester bioisosteres. In some embodiments, it is useful to limit the size of these substituents to, e.g., less than about 150, less than about 100, less than about 50, or less than about 20 atoms.

A variety of substituents are contemplated so that some potential combinations of claimed embodiments may be unstable or impractical to make. A person of ordinary skill in the art can select appropriate stable compounds within the disclosed genus of compounds based on the disclosure herein. Therefore, substituents generally are limited to those substituents that result in appropriate valence for the particular substituted element without forming a charged compound or a radical (except for titratable charged groups, stable zwitterionic forms and triplet neutral radicals with formal unpaired spins with full valencies), as can be conventionally determined by a person of ordinary skill in the art.

Introduction to MT477 Family

Formula 1(a) depicts an overall general structure of the MT477 family, with variations being set forth herein In all of the formulas, hydrogen atoms are not necessarily shown and can be presumed as needed at positions appropriate to complete the valence of the associated atoms. MT477 was suggested to be an anticancer agent using a topological computer model and determined to be an anticancer agent using in vitro cell culture experiments. Specifically, MT477 was tested by the NCI, and in other independent tests, and was shown to be an effective anti-cancer drug and an effective inhibitor of cell growth, as described in detail in the Examples below. The same model shows that the MT477 family is generally bioactive and inhibitory of cancer. Formula 1(a) shows motifs for the MT477 family, and has been found to be significant with respect to therapeutic function by computer modeling. An embodiment of the invention is a family of drugs, referred to herein as the MT477 family (Formulas 1-35), that is bioactive, affects cellular functions, and inhibits cancer.

Referring to Formula 1(a), A comprises a polycyclic group with at least a tricyclic group or a or a cyclic group with more than three connected rings; Z is a bond or a linking group; and Y comprises a cyclic group:

$$A\text{-}Z\text{-}Y \quad \text{Formula 1(a).}$$

The linking group Z comprises a backbone with at least one bond that joins A and at least one bond that joins to Y. Z may be a single bond that joins an atom of A to an atom of Y. With respect to the backbone that connects A to Y, the backbone is the path from A to B that has the fewest number of "steps"; if two paths have equally few steps, then one of the paths is treated as the backbone. A bond in the linker is a single "step" and may be a single bond, a double bond, or a triple bond. In some embodiments, the linking group connects to one member of A and one member of Y; alternatively, there may be more than one member of A and/or Y that is joined to the linking group; for example, a ring may join two members of A to at least one member of Y. In some embodiments, the backbone has between 1 and 20 bonds, between 1 and 30 bonds, or between 3 and 10 bonds; a person of ordinary skill will immediately appreciate that all ranges within these explicitly articulated bounds are contemplated, as well as other ranges that are suited to the structure and function of the compound. The backbone of the linking group may have substituents and substitutes, including, for example, those that are aliphatic, cyclic, heterocyclic, polycyclic, aromatic, aromatic heterocyclic, alicyclic, and heterocyclic non-aromatic.

In some circumstances, it is more convenient to describe the linking group, Z, as a —$(CH_2)_n$—X* group having at least one of C, S, O, N, or P; X, wherein X* is a bond, H, a halogen, a hydroxyl group, a thiol group, a carboxyl group, an amino group, an alkyl group, an alkoxy group, an alkenyl group, an alkynyl group, a heterocyclic group, or an aromatic group; and $-(CH_2)_n-$ is a group where n is an integer between 1 and about 50, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, a pi bond, H, a hydroxyl group, a thiol group, a carboxyl group, a carbamate, an oxocarbon group, an amino group, an amido group, an amide group, a phosphate group, a sulfonate group, an alkyl group, an alkoxy group, an alkenyl group, an alkynyl group, a heterocyclic group, an aromatic group, or a part of a ring group. The groups may be substituted as described herein. A person of ordinary skill in these arts can select appropriately stable compounds from the genera of compounds presented or claimed herein based on conventional chemical principles. A, Z, and Y may be joined to each other by a single bond, a double bond, a triple bond, or by interconnected ring structures.

Formulas 1(b)-1(d) depict a subgenus of Formula 1(a):

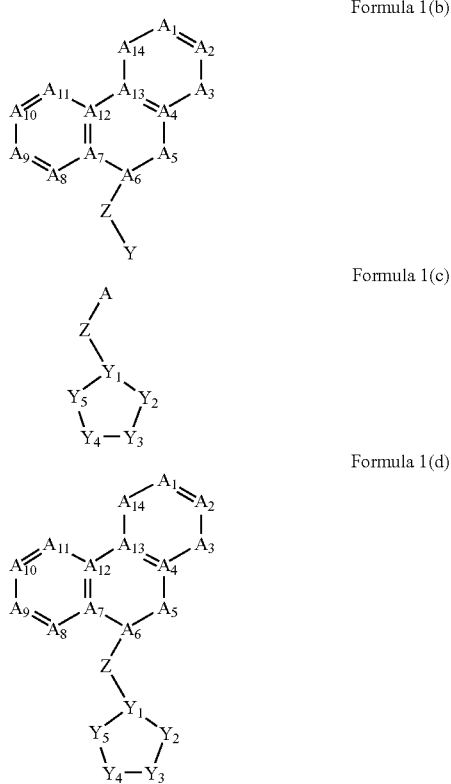

Referring to Formulas 1(b) to 1(d), each line joining two occupied positions is a chemical bond, and a line between an occupied position and a vacant position is a nullity, meaning that it is not necessary to posit each position as having an element or group therein, in which case that position and the bind associated therewith, may be considered to be absent form the formula. Formula 1(a), in one embodiment, has A comprising a tricyclic group with positions A1-A14, with Y comprising at least one cyclic group, as shown in Formula 1(bc). Formula 1(a), in another embodiment has Y comprising a cyclic group with positions Y1-Y5, as shown in Formula 1(c). Formula 1(a), in another embodiment, has A comprising a tricyclic group with positions A1-A14, with Y comprising a cyclic group with positions Y1-Y5, as shown in Formula 1(d). A, Z, Y, A1-A 14, and Y—Y5 may be joined to each other by a single bond, a double bond, a triple bond, or by interconnected ring structures.

In some embodiments, referring to Formulas 1(b) to 1(d), $A_1$-$A_7$ independently comprise C, S, O, P, or N. For example, A3 is S, A6 is N, and A8 is O, with A1, A2, A4, A5, and A being C. And Y1-Y5 independently comprise C, S, O, P, or N. For example, Y1 is N, and Y2-Y5 are C. Z is the linking group, for example with a backbone of 3 bonds to connect A6 to Y1. Above. Alternatively, other members of A or Y could be connected, e.g., one of A1-A14 and one of Y1-Y5. Suitable Substituent Groups include those set forth under the subheading "Substituent Groups and Substitution". Substituents for A, Z, and Y may include, for example, an 0 depending from at least one of A8, Y2, and Y5. And Z may include, for example a backbone of between 1 and 30 bonds, e.g., three C—C bonds, with substitutions as set forth under the subheading "Substituent Groups and Substitution". Formula 1(e) shows an example of a linking group that connects A6 to Y1 along a backbone of 3 bonds. Z1 and Z2 may be C, S, O, P, or N. Z1 and Z2 are groups, e.g., with Substituent Groups such as an oxygen with a double bond to Z1 and/or Z2.

Formula 1(e)

$$\begin{array}{c} A_6 \\ | \\ Z_2 \diagdown Z_1 \\ | \\ Y_1 \end{array}$$

The stereoisomers, e.g., diastereomers, of any of the structures depicted herein are expected to have the functions of the particular structures depicted or described herein. In the formulas set forth herein hydrogen atoms are not shown and can be presumed at all positions appropriate to complete the valence of the associated atoms.

Formula 2(a) depicts the structure of MT477, a compound that was tested, as described below, and found to have significant biological activities. Analogs of MT477 can be configurationally flexible analogs or conformationally restricted analogs. Conformationally restricted analogs have similar confirmations along the central nucleus or core structure of the molecule. Conformationally restricted analogs would be even more likely to have similar biological structure to MT477 relatively to other conformationally flexible analogs that have different confirmations along the core structure of the molecule. Similar conformational relationships can be followed for the other specific structures described herein. In other words, if other particular structures have desirable patterns of activity, conformationally restricted analogs would be expected in particular to have similar biological functionality.

Formulas 2(b)-2(g) show other embodiments that are expected have activity comparable to Formula 2(a), based on computer-driven simulations and structural commonality. Formula 2(h) shows a generic structure for some embodiments of the MT477 family. Substituents may be placed on the structures of Formulas 2(a)-2(h), with the substituents being as described herein in the "Substituent Groups and Substitution" section, above. Further, for the Formula 2(h) the C and S of Formula 2(h) are interchangeable with C, S, O, P, or N, depending upon the valence required for the position in light of the substituents of the embodiment being considered.

In some embodiments, the substituents for each numbered position each have less than 150 atoms each, less than 30 each, less than 10 each, or less than 5 each.
Formula 2(a)
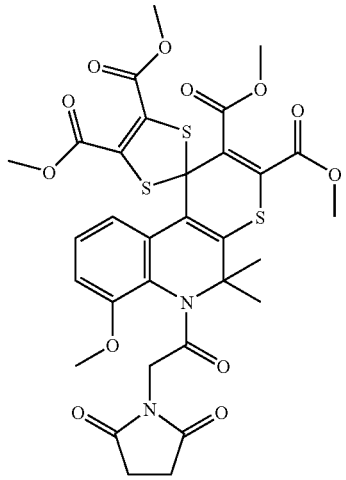
MT477
Formula 2(b)
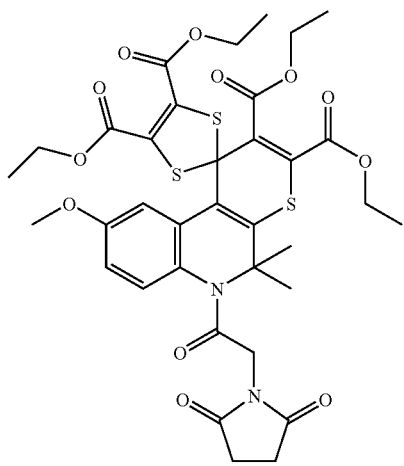
Formula 2(c)
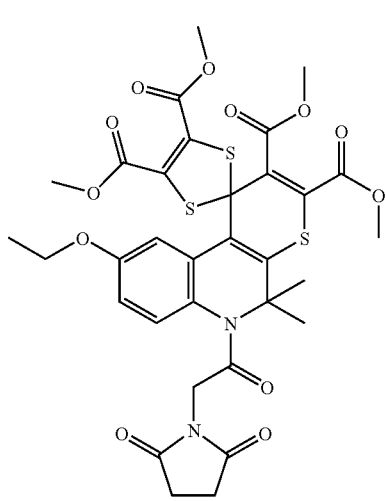
Formula 2(d)
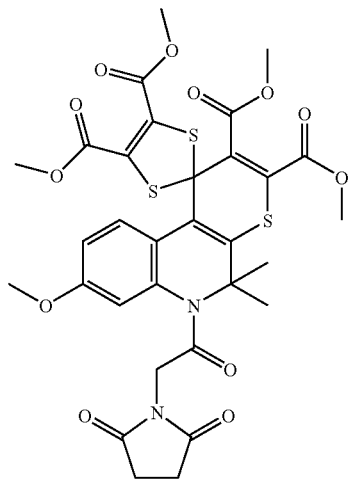
Formula 2(e)
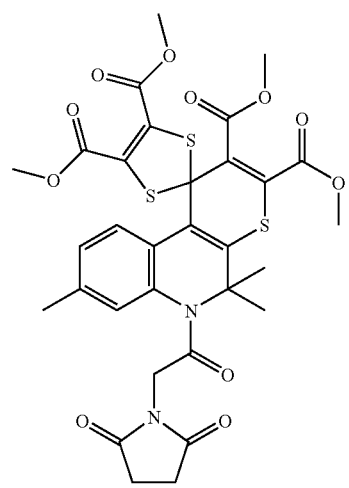
Formula 2(f)
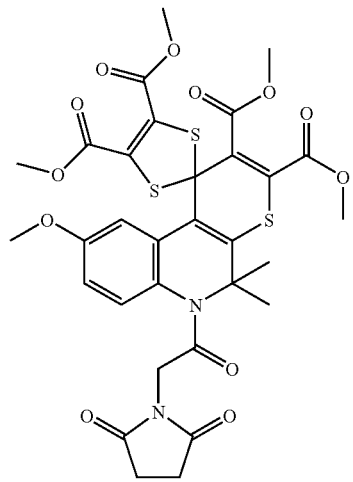

Formula 2(g)

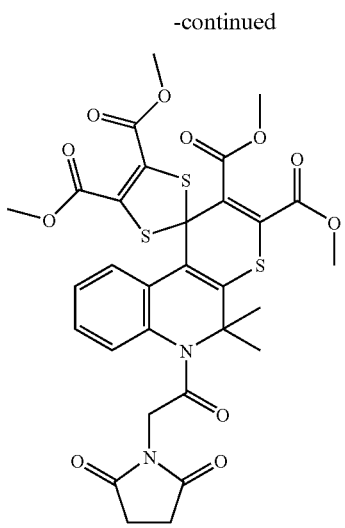

Formula 2(h)

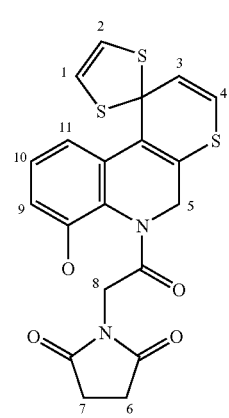

Another embodiment is shown in Formula 3(a). A1, A2, A3, A5, A6, A8, A9, A10, A11, A14, and Y1-Y5 each independently comprise C, S, O, P, or N. Positions R1-R8 and T1-T14 may be independently chosen to be, e.g., vacant, or a group that is member of the group consisting of a lone electron pair, a bond, a pi bond, H, a halogen, a hydroxyl group, a thiol group, a sulfonate group, a carboxyl group or carboxyl group bioisostere, an amino group, an amido group, an amide group, a phosphate group, an alkyl group, an alkenyl group, an alkynyl group, an alkoxy group, an oxo group, an ether, an ester or ester bioisostere, a ketone, a carboxyl, a cyclic group, an alicyclic group, a heterocyclic group, an aromatic group, groups that include O, S, Se, N, P, Si, C. In some embodiments, positions R1-R8 and T1-T14 have less than about 120 atoms, including substituents thereof. Z is a linking group. Further, in some embodiments, positions R1-R8 and T1-T14 are chosen so that they are interconnected with each other to form a cyclic structure, e.g., as in Formulas 9, 10, and 12 below. A, Z, Y, A1-A14, and Y—Y5 may be joined to each other by a single bond, a double bond, a triple bond, or by interconnected ring structures.

In some embodiments, at least one of T1-T14 is chosen to be a cyclic group, e.g., as in Formula 3(b), wherein B 1-B4 each independently comprise C, S, O, P, or N. Position An is a group that is an identity with one of A1-A14 or, alternatively, is a group that is C, S, O, P, or N that is connected to at least one of A1-A14 by a linking group having at least one bond, wherein the linking group may be Z, as described above. Referring to Formula 3(b), positions $_{v1-v8}$ may be independently chosen to be, e.g., vacant, or a group that is member of the group consisting of a lone electron pair, a bond, a pi bond, H, a halogen, a hydroxyl group, a thiol group, a sulfonate group, a carboxyl group, an amino group, an amido group, an amide group, a phosphate group, an alkyl group, an alkenyl group, an alkynyl group, an alkoxy group, an oxo group, an ether, an ester, a ketone, a carboxyl, a cyclic group, an alicyclic group, a heterocyclic group, an aromatic group, groups that include O, S, Se, N, P, Si, C. In some embodiments, positions $_{v1-v8}$ have less than about 120 atoms, including substituents thereof. Z is a linking group. In some embodiments, at least one of A1-A14 or Y1-Y5 is chosen to be vacant so as to provide a smaller ring.

Formula 3(a)

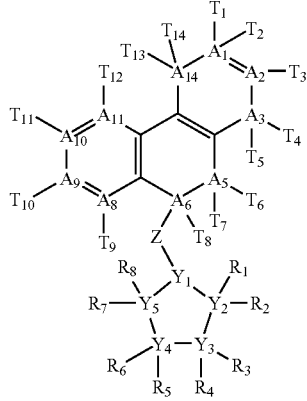

Formula 3(b)

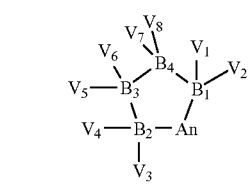

Another embodiment is shown in Formula 3(d), wherein A is depicted as a four-cyclic ring structure. A1, A2, A3, A5, A6, A8, A9, A10, A11, A14-A18 and Y1-Y5 each independently comprise C, S, O, P, or N. Positions R1-R8 and T1-T24 may be independently chosen to be, e.g., vacant, or a group that is member of the group consisting of a lone electron pair, a bond, a pi bond, H, a halogen, a hydroxyl group, a thiol group, a sulfonate group, a carboxyl group, an amino group, an amido group, an amide group, a phosphate group, an alkyl group, an alkenyl group, an alkynyl group, an alkoxy group, an oxo group, an ether, an ester, a ketone, a carboxyl, a cyclic group, an alicyclic group, a heterocyclic group, an aromatic group, groups that include O, S, Se, N, P, Si, C. In some embodiments, positions R1-R8 and T1-T24 have less than about 120 atoms, including substituents thereof. Z is a linking group. Further, in some embodiments, positions R1-R8 and T1-T24 are chosen so that they are interconnected with each other to form a cyclic structure. In some embodiments, at least one of A1-A24 or Y 1-Y5 is chosen to be vacant so as to provide a smaller ring. In some embodiments, at least one of T1-T14 is chosen to be a cyclic group, e.g., as in Formula 3(b), wherein B1-B4 each independently comprise C, S, O, P, or N. Positions An and positions $V_1$-$V_8$ may be chosen as described, above, with reference to Formula 3(b). A, Z, Y, B, V, $A_1$-$A_{14}$, $Y_1$-$Y_5$, $B_1$-$B_4$, and $V_1$-$V_8$ may be joined to each other by a single bond, a double bond, a triple bond, or by interconnected ring structures.

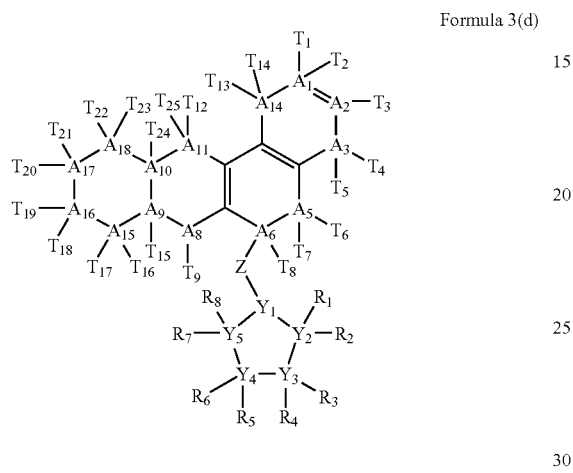

Formula 3(d)

Further, certain embodiments are related to Formula 4(a)-4(j). Formulas 4(a) and 4(b) show dotted lines to illustrate interconnection of the R positions with each other, with such interconnection among substituents being permissible, e.g., as described above. Embodiments without the illustrative dotted lines may also have interconnected positions.

Referring to Formulas 4(a)-4(k), X is independently chosen to be O, N, S, or P; Q is independently chosen to be N or C, and R, is a substituent as defined in the "Substituent Group" section, above. Consistent with this nomenclature, in some embodiments, a substituent, or each R may independently be a halogen, R', OR', a hydroxyl group, SR', a thiol group, $N(R')_2$, SO2R', OSO2R', N(R')2, NR'(CO)R', (CO)N(R')2, O(CO)N(R')2, an amino group, a 3-7 member saturated, partially unsaturated, or aryl ring having 0-2 heteroatoms independently selected from N, O. or S; with each R' being independently selected from H, an optionally saturated $C_1$-$C_6$ aliphatic group, 3-8 member saturated, partially unsaturated, or aryl ring having 0-4 heteroatoms independently selected from N, O, or S, wherein two R' on the same N, O, or S atom are optionally taken together with said N, O, or S to form a 3-membered saturated, partially unsaturated, or aryl ring having 1-4 heteroatoms independently selected from N, O, or S. Certain positions in Formulas 4(a)-4(j) have R replaced by O, e.g., as in 4(b). The 0 may be bonded with a single or double bond with corresponding other adjustments in the bonding as can be determined by a person of ordinary skill in the art and may, alternatively, be a hydroxyl, a carboxylic acid, sulfonic acid, phosphonic acid, phosphatidic acid, another acid or acid equivalent.

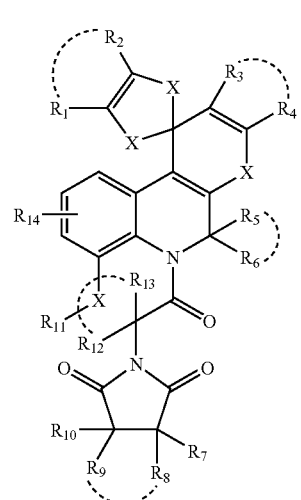

Formula 4(a)

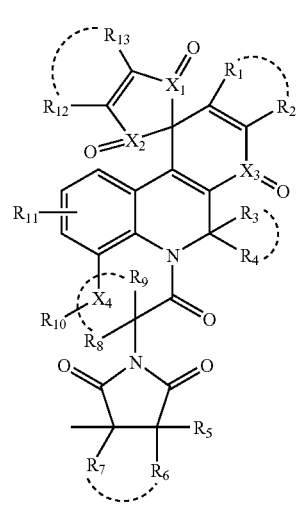

Formula 4(b)

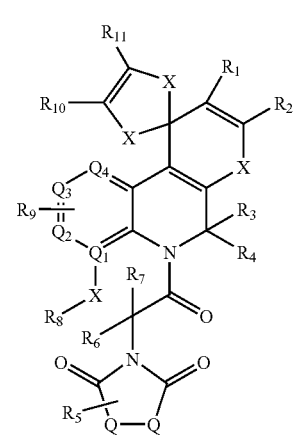

Formula 4(c)

-continued

Formula 4(d)
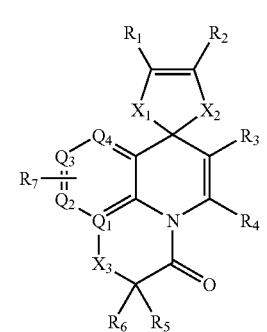

Formula 4(e)
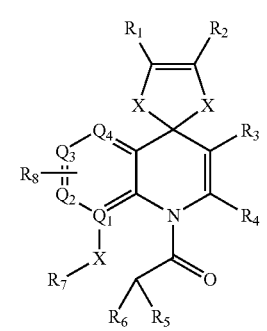

Formula 4(f)
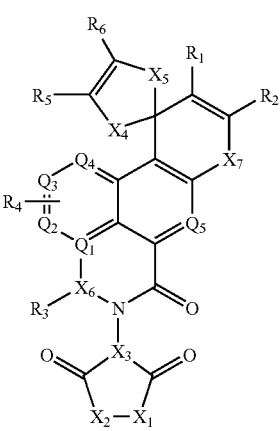

Formula 4(g)
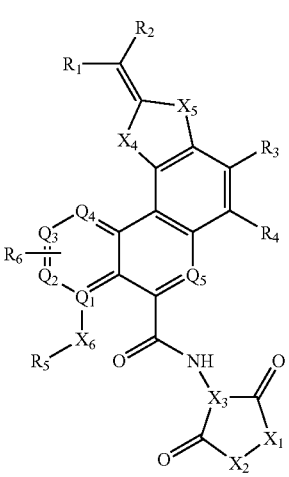

-continued

Formula 4(h)
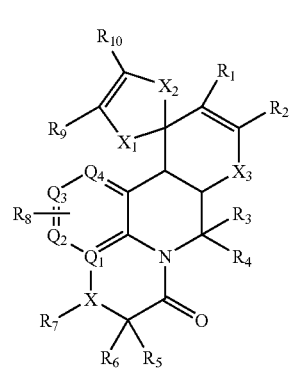

Formula 4(i)
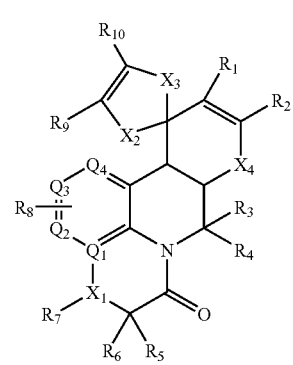

Formula 4(j)
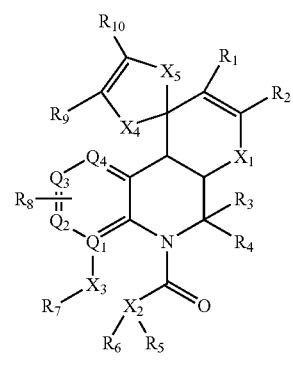

Formula 4(k)

Referring to Formula 4(k), and consistent with this description of Formulas 4(a)-4(j), $X_1$, and $X_2$ are independently chosen to be O, N, S, or P, and G is a group having at least two rings, with at least one ring having at least two members in common with at least one other ring. A substituent for Formula 4(k) may be as defined in the "Substituent Group" section, above. A substitution for a member of Formula 4(k) may be as described herein for substitution, see above. Examples of G, with G including an atom bound to $X_1$ and $X_2$ with suitable valency, are Certain embodiments of the above Formulas are shown in Formulas, 5-33, below
Formula 4(l)
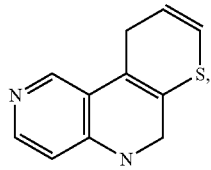
Formula 4(m)
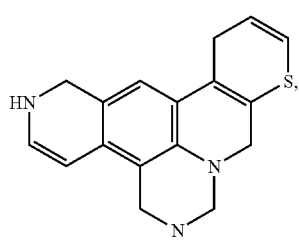
Formula 4(n)
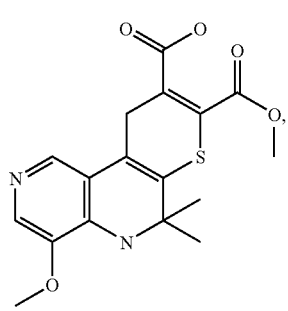
Formula 4(o)
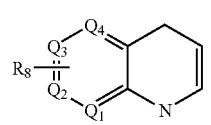
(with $Q_1$-$Q_4$ and $R_8$ being as described for Formula 4(e), above), and
Formula 4(p)
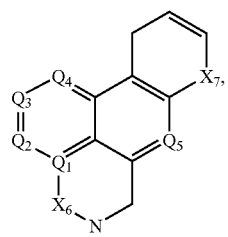
(with $Q_1$-$Q_5$, $X_6$, $X_7$, being as described for Formula 4(f), above).
Formula 5
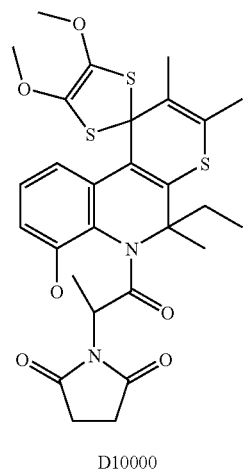
D10000
Formula 6
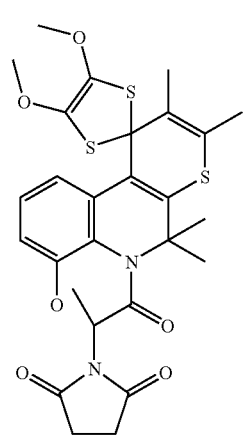
D10000A
Formula 7
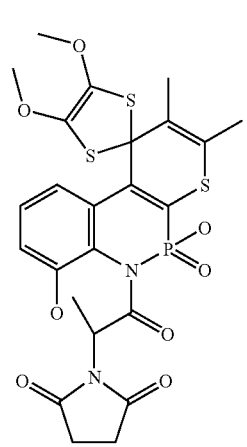
D10000B -continued
Formula 8
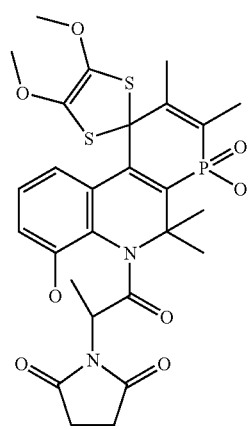
D10000C
Formula 9
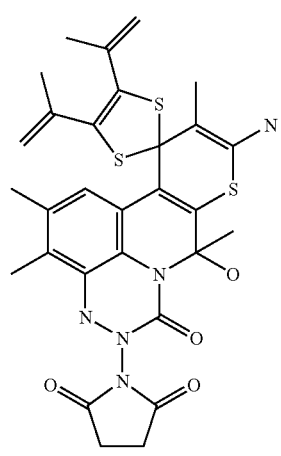
D20001
Formula 10
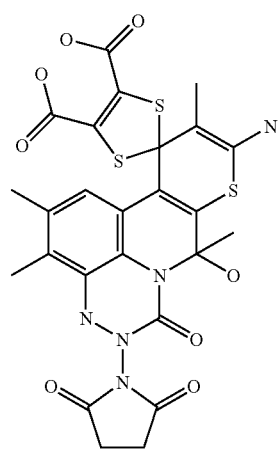
D20001A
-continued
Formula 11
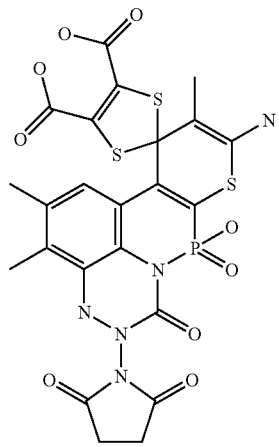
D20001B
Formula 12
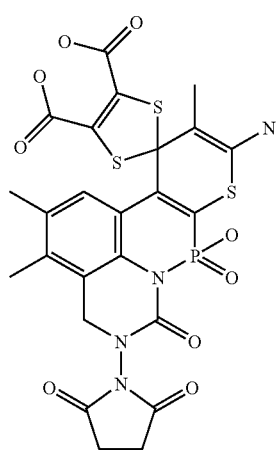
D20001C
Formula 13
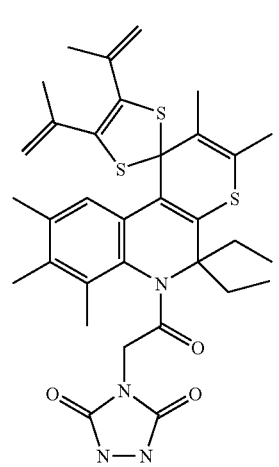
D30010

Formula 14
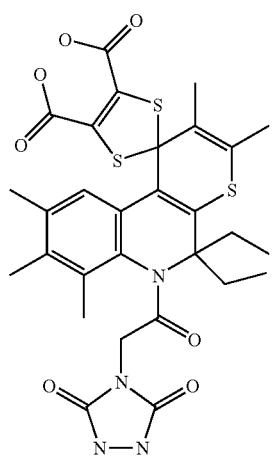
D30010A
Formula 15
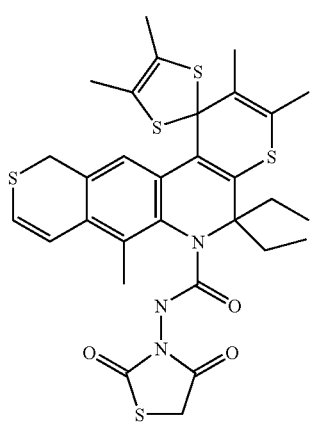
D40059
Formula 16
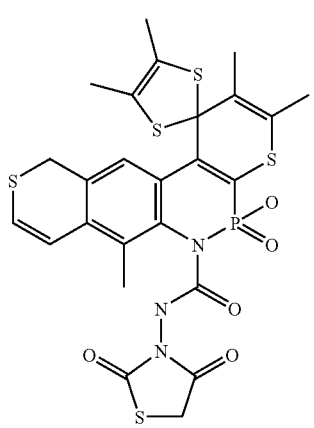
D40059A
Formula 17
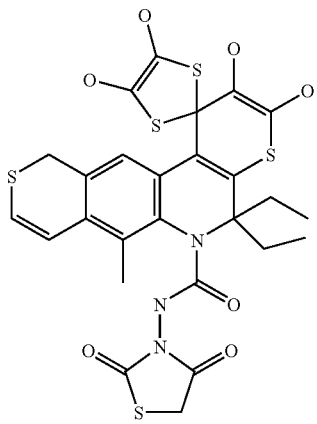
D40059B
Formula 18
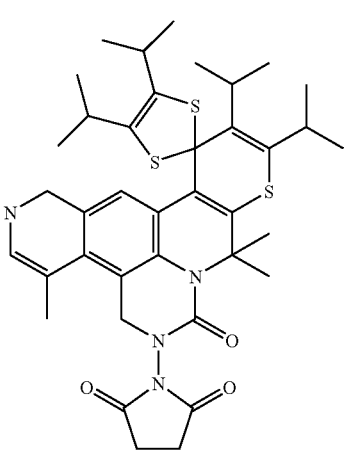
D60015
Formula 19
D60015A -continued
Formula 20
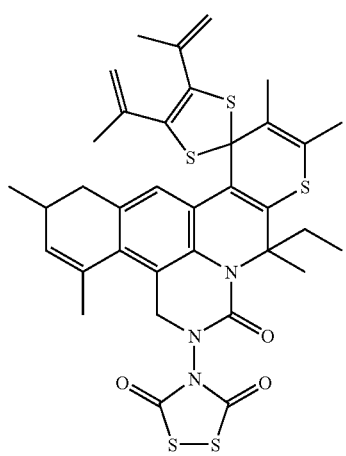
D70017
Formula 21
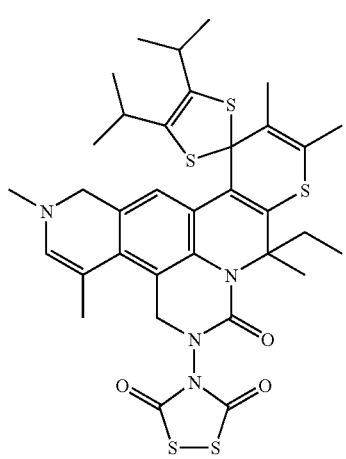
D70017A
Formula 22
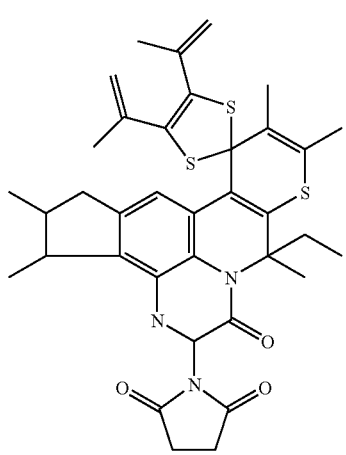
D80019
-continued
Formula 23
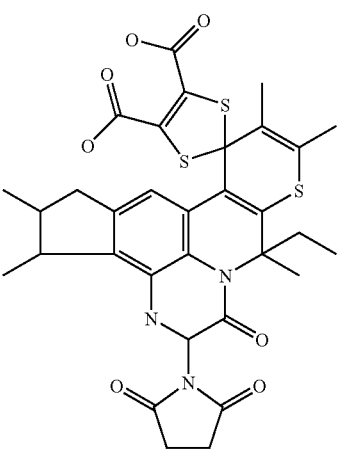
D80019A
Formula 24
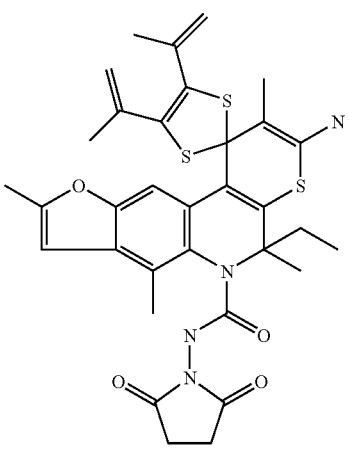
D90002
Formula 25
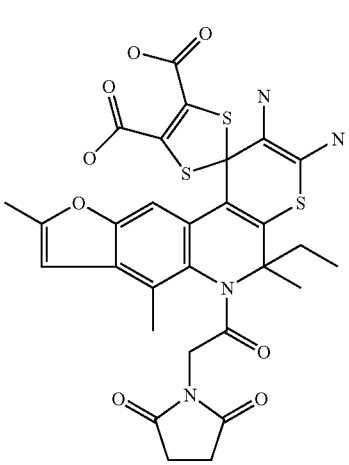
D90002A Formula 26
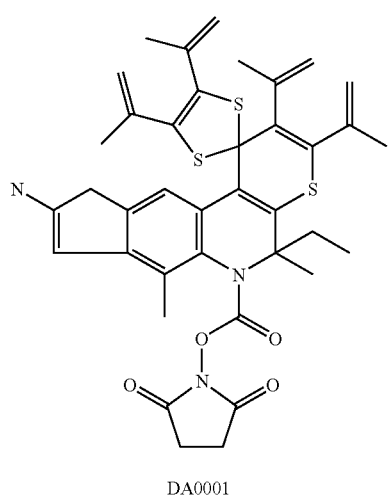
DA0001
Formula 27
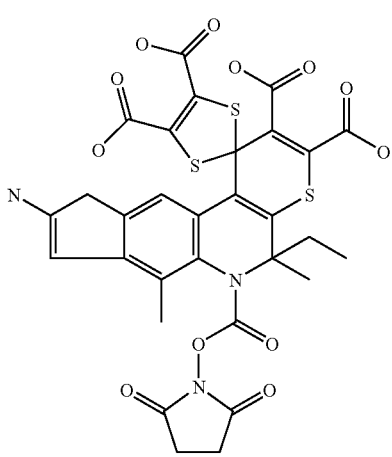
DA0001A
Formula 28
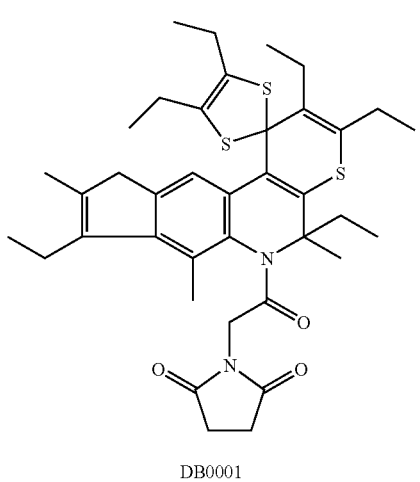
DB0001
Formula 29
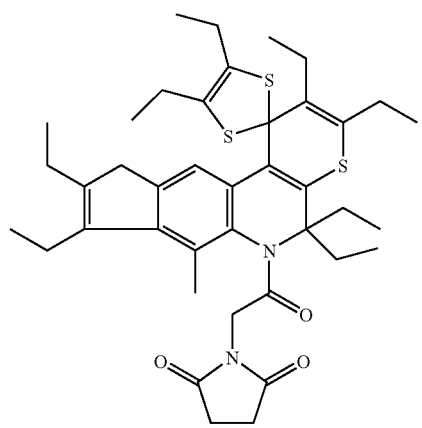
DB0001A
Formula 30
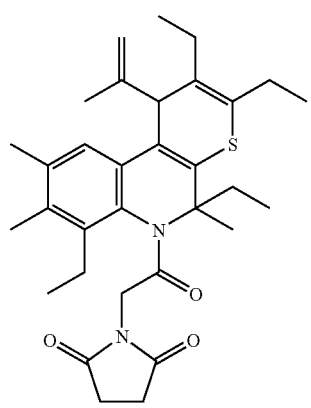
DC0001
Formula 31
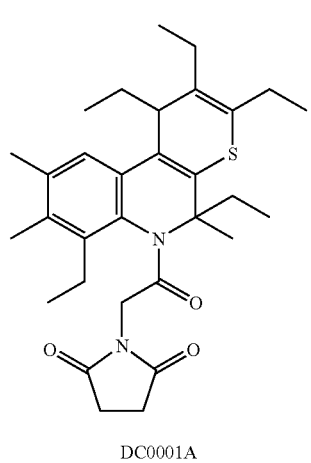
DC0001A Formula 32

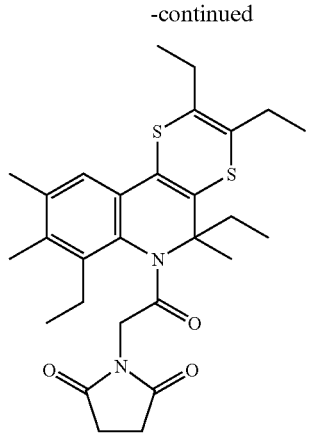

DC0001B

Formula 33

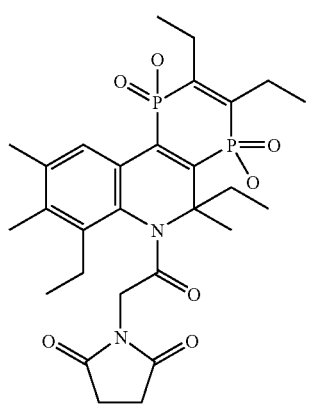

DC0001C

Some embodiments are, without being bound to a particular theory, believed to be relatively more biologically active than other embodiments. Formula 34 depicts a bicyclical ring structure, 1,4,8-Trithia-spiro[4.5]deca-2,6,9-triene, that may form a portion of some of the embodiments sort forth herein. The substituents at positions 2, 3, 9, 10 (see Formula 34) tend not to close rings, i.e. are acyclic. The presence of carboxyl, carbonyl, hydroxyl on these points may improves the Protein Kinase C-activation potency of the MT477 family as well as apoptosis. The presence of P (or phosphate) instead of S on position (8) may also be helpful. The groups of Formula 34 may be substituted or decorated with substituents as described for Formula 1.

Formula 34

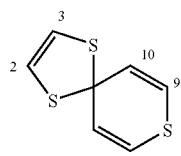

And Formula 35 depicts a compound having groups A, Z, and Y selected as indicated therein. The substituents on positions 6,7 of the hydroxyquinoline bicycle tend to close rings (cycles) but those on position 2 of the hydroxyquinoline bicycle do not close rings. The presence of different heteroatoms (N, S, O) on the positions 1' (the carbon of the N-methylpyrrolidine, see Formula 35) as well as 3' and 4' of the pyrrolidine ring, may lead to improved biological activity. Phosphorous (and phosphate groups) could also be effective at position 2 of Formula 35. The groups of Formula 35 may be substituted or decorated with substituents as described for Formula 1.

Formula 35

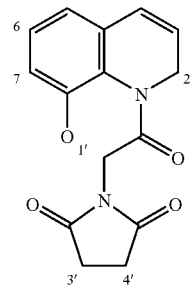

Certain embodiments of the above Formulas are shown in Formulas, 36-45, below:

Formula 36 (N1)

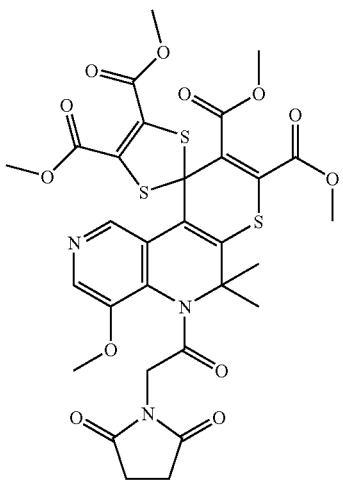

Formula 37 (D60015A)

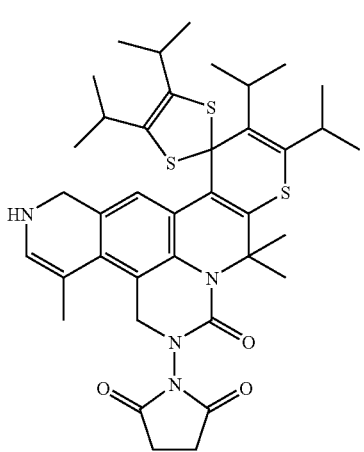

Formula 38 (N7)
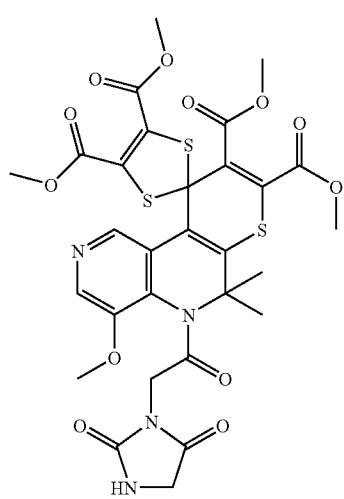
Formula 39 (N6)
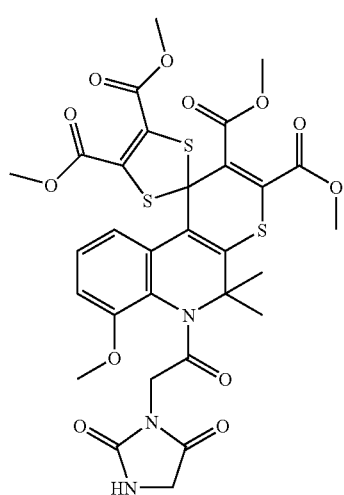
Formula 40 (N5)
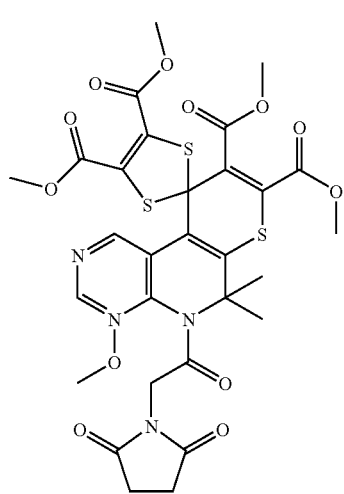
Formula 41 (N14)
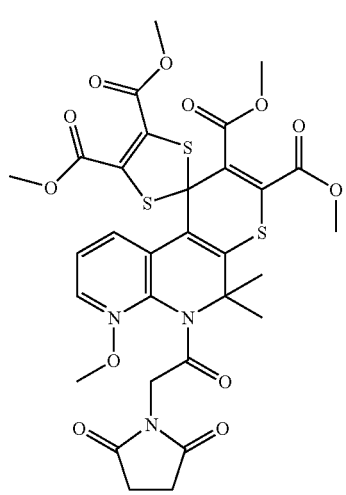
Formula 42 (N3)
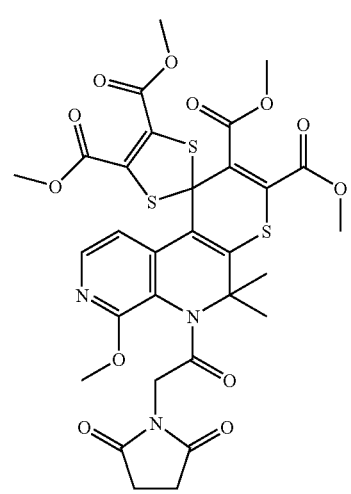
Formula 43 (N2)
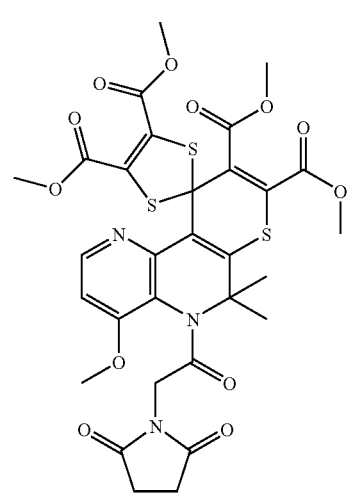

-continued
Formula 44 (MT477-30)
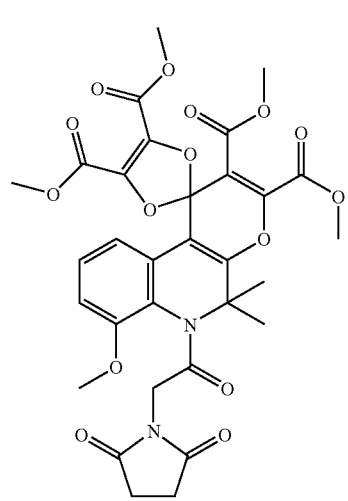
Formula 45 (3N)
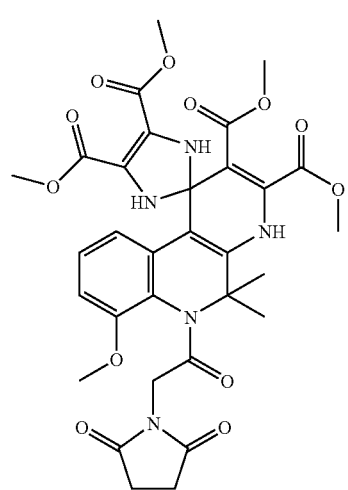
Synthesis of Compounds
An exemplary reaction scheme for the MT477 family is set forth, below, in Scheme I.
Scheme I
Synthetic Scheme
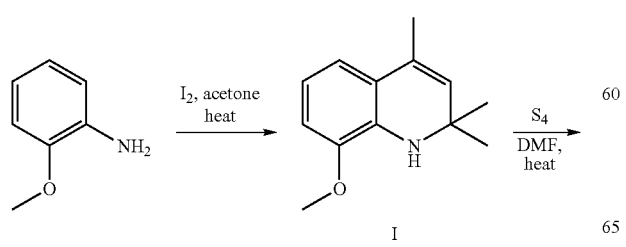
-continued
Reactant A
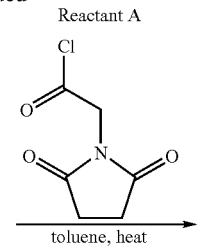 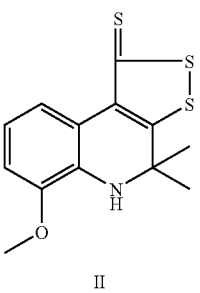
toluene, heat
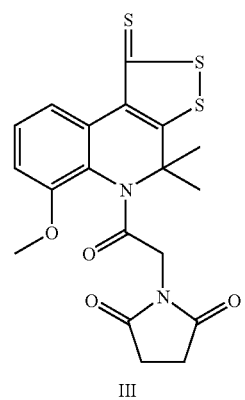
III
Reactant B
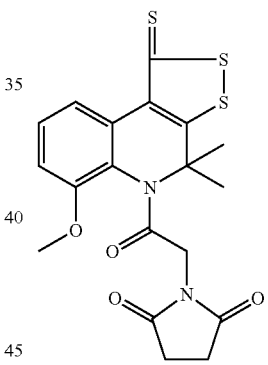 + 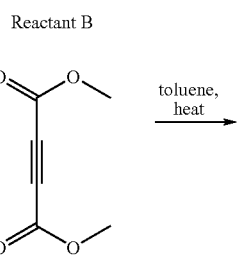 toluene, heat
III     2 eq
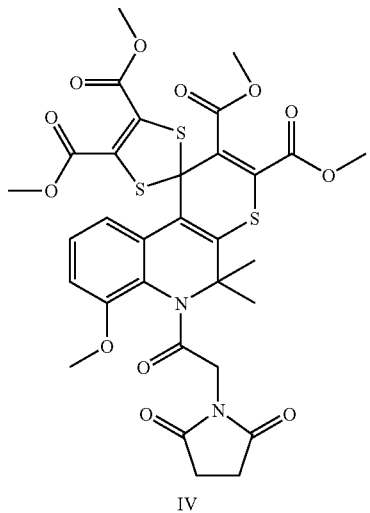
IV

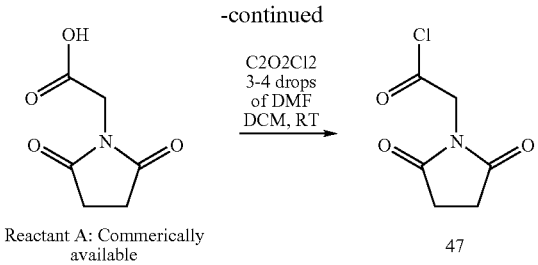

Reactant A: Commerically available

Scheme I depicts a synthesis route that can be used, in general, to make members of the MT477 family. Compound I is made from the indicated precursor by reaction with $I_2$ in acetone and heat. Compound I is reacted with $S_4$ in dimethylformamide with heat to produce Compound II, which is combined with Reactant A in toluene and heat to make Compound III. Compound III is combined with Reactant B in toluene with heat to form Compound IV. Scheme I further depicts the formation of Reactant A from a commercially available precursor. Beilstein contains further details with respect to these and related synthesis protocols. Artisans of ordinary skill will be able to synthesize such variants of MT477 as are set forth herein, and other chemicals that are in the family of chemicals that share the features of MT477.

Additional information is provided with respect to Compound I (CAS 51035-27-9) in 2,4-dimethylquinoline, organic synthesis, coll. Vol. 3, p. 329; vol. 28, p. 49, in Novel facile synthesis of 2,2,4 substituted 1,2-dihydroquinolines via a modified Skraup reaction, Tetrahedron Letters, volume 43, issue 21, 20 May 2003, pages 3907-3910, and in Efficient microwave-assisted synthesis of quinolones and dihydroquinolones under solvent-free conditions, Tetrahedron, volume 59, issue 6, 3 Feb. 2003, pages 813-819. Additional information with respect to Compound II is found in Reactions of 2,2-dialkyl-1,2-dihydroquinolines. Part IV. 4,5-dihydro-4,4-dimethyl-1H-1,2-dithiolo[3,4-c]quinoline-1-thiones. J. P. Brown. J. Chem. Soc. (C), 1968. p. 1074. Additional information with respect to Compound III is found in Zhurnal Oganisheskoi Khim. January 1988, volume 24, Number 1, part 2, page 208. Note that acid plus a peptide coupling type reaction is an alternative route. Additional information with respect to Compound IV is found in 4,4-dimethyl-4,5-dihydro-1,2-dithiolo-[3,4-c]quinolone-1-thiones in 1,3-dipolar cycloaddition reactions with acetylenic dipolarophiles. K. Shikhaliev, et al. Chemistry of Heterocyclic Compounds, vol. 35, no. 5, 1999.

Certain embodiments within the MT477 family are directed to a substitution or substituent of a group with an oxygen atom. Suitable reactions, for example, involve the formation of an ether linkage —C—O—C—. Persons or ordinary skill in the art recognize that ether linkages can be formed from a sulfuric acid catalyzed de-hydrolysis reaction of two corresponding alcohols or from a reaction between a halide substituted compounds with an alkoxide. In certain embodiments, a —C—C—C— linkage is required. Carbon-carbon bonds can be formed using a Grignard reagent, in which a compound R—C—MgBr reacts with a compound Br—C—R'R" to form R—C—C—R'R". Some embodiments are directed to the use of phosphorous in the MT477 family. Various other reaction schemes can be followed by a person of ordinary skill in the art to form the various stable compounds within the MT477 family based on the representative teachings herein.

Phosphorous is multivalent and can form bonds with varying number of atoms (Coordination Number), which can vary from 1 to 6. Phosphorus can form bonds with many other elements and can be substituted into Formulas and reaction schemes as appropriate to satisfy its valency requirements. It has empty d-orbitals which readily accept electrons from donors. In many circumstances, phosphorus can extend its number of bonds to take a new group and via a substitution reaction more readily than carbon. Phosphorus can form bonds readily with oxygen, nitrogen and sulfur, and also can form bonds with carbon. These four bonds enable the linkage of phosphorus to organic compounds to make organophosphorus compounds. References for phosphorous chemistry include, e.g., A Guide to Organophosphorus Chemistry, Louis D. Quin, January 2000 (ISBN: 0-471-31824-8); Organophosphorus Chemistry—A Practical Approach in Chemistry, Edited by Patrick J. Murphy, University of Wales, Bangor, June 2004. Various other reaction schemes can be followed by a person of ordinary skill in the art to form the various stable compounds within the MT477 family based on these and other representative teachings herein.

MT477 Family Compounds

The compounds described herein are designed for activity against various cancers. As shown in Examples 1-5, MT477 has demonstrated in vitro activity against multiple cancers, as evidenced with favorable results for inhibiting growth of cell lines that are predictive for leukemia, non-small cell lung cancer, colon cancer, central nervous system cancer, melanoma, ovarian cancer, renal cancer, prostate cancer, and breast cancer. The high $-\log_{10} GI50$ values measured for many cell lines all indicate that MT477, and related compounds, can be expected to be useful for treating cancer or otherwise inhibiting cell growth or survival.

Computer modeling and comparison to other chemicals shows that MT477 and the MT477 family are anti-cancer agents, inducers of apoptosis agents, protein kinase agents, and hormonal antagonists. Examples 1 and 5 show the results of computer models that predict efficacy for the MT477 family. As shown in Examples 1 and 5, chemicals used for such comparisons are paclitaxel, topotecan, etoposide, tamoxifen, anastrozole, and flutamide. The other Examples show that the computer models were successful for predicting the effectiveness of MT477.

Since the MT477 family of drugs generally have desirable characteristics, e.g., as outlined in Examples 1 and 5, and as shown by computer modeling and comparisons, they may be used to treat patients to inhibit cancer and to act in the patients as apoptosis agents, protein kinase agents (e.g., PKC-alpha modulation), and hormonal antagonists. Cells in vitro and in vivo may be exposed to members of the MT477 family for this purpose. MT477 and the MT477 family can be useful not only as drugs for treating or curing certain cancer types but also as drugs that inhibit certain cancer types in humans and non-human animals. Further, apoptotic agents, and hormonal antagonists are important commercial products that are used in many ways; similarly, members of the MT477 family may also be used for such purposes. Accordingly, potential uses would include use for diagnostics, cell testing, and as chemical reagents for commercial sale.

Further, the MT477 family of chemicals may be used in vitro or in vivo to slow or stop cell growth, kill cells, or to inhibit the growth of cells in vitro or in vivo. Apoptosis inductors, protein kinase agents, and hormonal antagonists are valuable research tools for in vitro and in vivo treatment of cells. Antibacterials and antifungals are valuable products for suppressing, inhibiting and/or killing bacteria and fungi in vitro, in vivo, ex vivo, and in a multitude of environments such as residential, commercial, hospital, and industrial settings. These compounds may be used alone or in combination with other drugs to achieve the most suitable therapy for a patient or other purposes. Appropriate patients include any animals that can benefit from such therapy and include mammals, such as humans, farm animals and pet animals.

Anti-cancer compounds that are effective against one type of cancer can be expected to have an anti-cancer effect against other types of cancers. As shown in Example 3, e.g., Table 3, MT477 displays activity against a wide variety of cancer types. While some compounds described herein may be clinically preferable for use in certain types of cancer, they are also expected to be useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma. According to another embodiment of the invention, compounds of the invention are directed to therapies for cell proliferative disorders, for example, Alzheimer's disease, viral infections, auto-immune diseases and neurodegenerative disorders.

MT477 and the MT477 family are also useful when delivered in combination with medical devices. For example, the devices may be implantable for a short period of time, or an extended time. Other medical devices are only transiently introduced into the body. Examples of implants made for an extended period of time are stents, e.g., use in blood vessels or other portions of the body, heart valves, pacemakers, defibrillators, angioplasty devices, artificial blood vessels, artificial hearts, and indwelling catheters. Examples of devices implantable for short periods of time include temporary catheters, oxygenator lines, blood pumps, blood filters, and drug delivery systems. Examples of devices introduced only transiently are guidewires, balloons for e.g., angioplasty, and rapidly degradable devices. Other medical devices used with a member of the MT477 family may be devices deployed temporarily, permanently, or semi-permanently in contact with blood, e.g., sensors, biosensors, and diagnostic kits.

One use of MT477 family compounds is to inhibit cell growth around an implanted device. The inhibition may be for a short time, for example while the body's inflammatory reaction is most active, or on a longer term basis. For example, an MT477 family member may be delivered using a strategy of sustained release, slow release, e.g., by enteric coating. The inhibition of cell growth is a significant strategy for the prevention of restenosis after angioplasty or implanting a stent in a blood vessel. Inhibition of cell growth is also a significant strategy for enhancing the biocompatibility of implanted devices so that the reaction of the body to the devices is minimized.

Cells may be exposed to a member of the MT477 family. Exposure can be useful for, e.g., therapeutic treatments, for testing, for diagnosis, and research. The activities of MT477 are useful for studying certain aspects of cellular metabolism and function, e,g., cell growth, or models of disease states such as cancer. Cells is a term used broadly, and includes cells in vitro, in vivo, prokaryotic, eukaryotic, and fungal.

Administration of Compositions

Pharmaceutically acceptable salts of the compounds described herein may be synthesized according to methods known to those skilled in this art, see, for example Pharmaceutical Salts: Properties, Selection, and Use, P. Heinrich Stahl (Editor), Camille G. Wermuth (Editor) June 2002. Generally, such salts are prepared by reacting the free base forms of these compounds with a stoichiometric amount of the appropriate acid in water or in an organic solvent, or in a mixture of the two; generally, nonaqueous media like ether, ethyl acetate, ethanol, isopropanol, or acetonitrile are preferred. Lists of some appropriate salts are found, for example, in Remington's Pharmaceutical Sciences, 17th ed., Mack Publishing Company, Easton, Pa., 1985.

In some embodiments, the compounds described herein are used in combination with one or more potentiators and/or chemotherapeutic agents for the treatment of cancer or tumors. Examples and descriptions of potentiatiors and combination therapies are provided in, for example, U.S. Pat. Nos. 6,290,929 and 6,352,844.

The compounds described herein may be administered as a single active drug or a mixture thereof with other anti-cancer compounds, and other cancer or tumor growth inhibiting compounds. The compounds may be administered in oral dosage forms that include tablets, capsules, pills, powders, granules, elixirs, tinctures, suspensions, syrups, and emulsions. Further, the compounds may be administered in intravenous (bolus or infusion), intraperitoneal, subcutaneous, or intramuscular form.

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Techniques and compositions for making dosage forms useful for materials and methods described herein are described, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S.

Davis, Clive G. Wilson, Eds.); Modern Pharmaceutics Drugs and the Pharmaceutical Sciences, Vol 40 (Gilbert S. Banker, Christopher T. Rhodes, Eds.).

Suitable binders, lubricants, disintegrating agents, coloring agents, flavoring agents, flow-inducing agents, and melting agents may be included as carriers, e.g., for pills. For instance, an active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like.

Suitable binders include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, for example, starch, methyl cellulose, agar, bentonite, xanthan gum, and the like.

The compounds may also be used with liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds may also be coupled to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

The active compounds can be administered orally in solid dosage forms, such as capsules, tablets, and powders, or in liquid dosage forms, such as elixirs, syrups, and suspensions. The active compounds can also be administered parenterally, in sterile liquid dosage forms.

Capsules may contain the active compound and powdered carriers, such as lactose, starch, cellulose derivatives, magnesium stearate, stearic acid, and the like. Similarly, such diluents can be used to make compressed tablets. Both tablets and capsules can be manufactured as immediate release products or as sustained release products to provide for continuous or long-term release of the active compounds. The deliverable form of the compounds can be sugar coated or film coated to mask any unpleasant taste and protect the tablet from the atmosphere, or enteric coated for selective disintegration in the gastrointestinal tract.

For oral administration as a liquid, the drug components may be combined with any oral, non-toxic, pharmaceutically acceptable inert carrier such as ethanol, glycerol, water, and the like. Examples liquid forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Liquid dosage forms may contain, for example, suitable solvents, preservatives, emulsifying agents, suspending agents, diluents, sweeteners, thickeners, and melting agents.

Liquid dosage forms for oral administration can contain coloring and flavoring, as needed. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds described herein may also be administered in intranasal form via use of suitable intranasal vehicles, or via transdermal routes, using those forms of transdermal skin patches known to those skilled in these arts. To be administered in the form of a transdermal delivery system, the dosage administration will generally be continuous rather than intermittent throughout the dosage regimen. Parenteral and intravenous forms may also include minerals and other materials to make them compatible with the type of injection or delivery system chosen.

The compounds set forth herein may also be used in pharmaceutical kits for the treatment of cancer, or other purposes, which comprise one or more containers containing a pharmaceutical composition comprising a therapeutically effective amount of the compound. Such kits may further include, if desired, one or more of various components, such as, for example, containers with the compound, containers with one or more pharmaceutically acceptable carriers, additional containers, and instructions. The instructions may be in printed or electronic form provided, for example, as inserts or labels, indicating quantities of the components to be administered, guidelines for administration, and/or guidelines for mixing the components.

Dosage levels include from about 0.01 mg to about 2000 mg of active compound per kilogram of body weight per day are preferable dosages; persons of ordinary skill in these arts will recognize that all doses and ranges between these explicit values are contemplated, e.g., 0.01 to 100, and 0.1 to 50 mg/kg. The amount of active compound that may be combined with the carrier materials to produce a single dosage form will vary depending upon the host treated and the particular mode of administration. Dosage unit forms will generally contain between from about 0.01 mg to about 10,000 mg of an active compound; persons of ordinary skill in these arts will recognize that all doses and ranges between these explicit values are contemplated. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy. For example, a suitable dosage adopted for oral or intravenous administration of a compound of the MT477 family may range from about 0.01 to about 1000 mg per dose, from once per week to 5 times daily.

The method of administration of the compounds set forth herein can be any suitable method that is effective in the treatment of the particular cancer or tumor type being treated. Treatment may be oral, rectal, topical, parenteral or intravenous administration or by injection into a tumor or cancer. The method of applying an effective amount also varies depending on the disorder or disease being treated. Parenteral treatment may be, e.g., by intravenous, subcutaneous, or intramuscular application of the compounds set forth herein, formulated with an appropriate carrier, additional cancer inhibiting compound or compounds or diluent to facilitate application. Certain embodiments of the invention include compositions that contain a compound as set forth herein, e.g., as in Formulas 1-5.

EXAMPLES

Example 1

MT477 Predicted to be an Effective Anti-Cancer Agent by Topological Computer Modeling Table 1 shows the output for the topological computer model for MT477. This output indicates that MT477 and related compounds, are effective anti-cancer agents. As a control for the computer model, the computer model was also used to predict the results for known anti-cancer agents such as paclitaxel and topotecan, as well as for ifosfamide and Busulfan, agents that are typically not employed as anti-cancer agents. As indicated in Table 1, MT477 is predicted to be effective for multiple types of cancer, with a $-\log GI_{50}$ value of at least 6.3 for the cancers described in Table 1.

Analogs having a structure similar to MT477 are expected to have similar pharmacokinetic properties.

Example 2

NCI Three Cell-Line Test Indicates that MT477 is an Effective Anti-Cancer Agent

This Example shows that MT477 is predicted by in vitro cell testing to be an effective anti-cancer agent. The testing in this Example was performed by NCI, as per their 3-cell line panel test. The results are reported as the percent of the growth of the treated cells compared to the untreated control cells. The criterion for being an effective compound and for being subjected to further testing is that the tested compound reduce the growth of any one of the three cell lines to approximately 32% or less. As shown in Table 2, MT477 was much more effective than the commonly accepted scientific accepted criterion; in fact, MT477 reduced the growth of all three cell lines to close to zero at the tested concentration of 0.05 millimolar.

TABLE 1

Topological computer model results for MT477 and selected anti-cancer compounds.

| Modeled Properties for Compounds | MT477 PREDICTED | MT477 ACTUAL | Paclitaxel | Topotecan | Ifosfamide | Busulfan |
|---|---|---|---|---|---|---|
| Activity against breast cancer NCI-MCF7 | >90%* | Yes | >90%* | >90%* | <10% probability | <10% probability |
| $-\log(GI_{50})$, molar | 7.2 | 5.8 | 8.8 | 7.5 | <5 | <5 |
| Activity against lung cancer NCI-H460 | >90%* | Yes | >90%* | >90%* | <10% probability | <10% probability |
| $-\log(GI_{50})$, molar | 6.3 | 5.76 | 7.4 | 7.6 | <5 | <5 |
| Activity against CNS cancer NCI-SF268 | >90%* | Yes | >90%* | >90%* | <10% probability | <10% probability |
| $-\log(GI_{50})$, molar | 7.3 | 5.6 | 7.6 | 7.0 | <5 | <5 |
| Protein Kinase C Inhibitor, Log Ki, nM | 0.2 | Not Tested | 0.1 | 2 | >4 | >4 |
| Induction of Apoptosis | 47% | Not Tested | 69% | 3.6% | 0% | 0% |

*predicted that activity was probable

The pharmacokinetic properties of MT477 have been calculated and result in some predictions that show the usefulness of the chemical. The predictions indicate that MT477 will decay according to a 2 or 3 compartment model with a predicted terminal elimination half-life of about 72 hours. An average peak plasma concentration of about 0.04 mg/L should occur about two hours after dosing. The total clearance is estimated to be about 55-80 L/h. The expected mean oral bioavailability of MT477 is about 20% and about 90% of the MT477 in the plasma is bound to protein in the body.

TABLE 2

MT477 shown to be effective by NCI 3 cell-line test.

| | Growth, Percentage | | |
|---|---|---|---|
| Concentration of MT477 in growth medium | MCF7 Cell line (Breast Cancer) | NCI-H4 60 cell line test (Non-Small cell Lung) | SF-268 Cell Line (Central Nervous System) |
| $5(10^{-5})$ Molar | about 0 | about 0 | about 0 |

The methods for conducting the test are described below in Example 3, except that the cells were exposed to a single concentration of MT477, at $5\times10^{-5}$ Molar, and colorimetric determinations were made with alamar blue (Biotechniques 21(5):780-782 (1996)).

Example 3

NCI Multiple Cell Line Test Shows that MT477 is an Effective Anti-Cancer Drug The NCI tested MT477 60 cell line test, and reported the $GI_{50}$, TGI, and $LC_{50}$ values of MT477 for each cell line, reported herein at Table 3.

TABLE 3

NCI multiple cell-line test for the drug MT477, results reported as molar, with maximum dose of 0.05 millimolar.

| Panel/Cell Line | $-\log_{10}GI50$ | $-\log_{10}TGI$ | $-\log_{10}LC50$ |
|---|---|---|---|
| Leukemia | | | |
| CCRF-CEM | 5.49 | * | * |
| HL-60 (TB) | 5.66 | 4.83 | * |
| K-562 | 5.79 | 4.99 | * |
| MOLT-4 | 5.99 | 5.64 | 4.68 |
| RPMI-8226 | 5.12 | 4.77 | 4.42 |
| Non-Small Cell Lung Cancer | | | |
| A549/ATCC | 5.42 | 4.77 | * |
| EKVX | 5.07 | 4.7 | 4.34 |
| HOP-92 | 5.78 | 5.21 | 4.6 |
| NCI-H226 | 5.15 | 4.72 | * |
| NCI-H23 | 6.02 | 5.72 | 5.42 |
| NCI-H322M | 5.19 | 4.87 | 4.55 |
| NCI-H460 | 5.76 | * | * |
| NCI-H522 | 5.03 | 4.31 | * |
| Colon Cancer | | | |
| COLO 205 | 5.78 | 5.19 | * |
| HCT-116 | 6.02 | 5.75 | 5.48 |
| HCT-15 | 5.83 | 5.27 | 4.69 |
| HT29 | 5.77 | 4.65 | * |
| KM12 | 5.64 | * | * |
| SW-620 | 5.78 | * | * |
| CNS Cancer | | | |
| SF-268 | 5.67 | 4.97 | * |
| SF-295 | 5.02 | 4.56 | * |
| SNB-19 | 5.1 | 4.78 | 4.46 |
| U251 | 5.7 | 5.14 | 4.72 |
| Melanoma | | | |
| LOX IMVI | 6.07 | 5.79 | 5.52 |
| M14 | 602 | 5.74 | 5.47 |
| SK-MEL-2 | 5.33 | 4.41 | * |
| SK-MEL-28 | 5.81 | 5.27 | * |
| SK-MEL-5 | 5.21 | 4.51 | * |
| UACC-257 | 5.83 | 5.53 | 4.55 |
| UACC-62 | 5.93 | 5.55 | 5.03 |
| Ovarian Cancer | | | |
| IGROV1 | 4.75 | 4.3 | * |
| OVCAR-3 | 6.09 | 5.74 | 5.39 |
| OVCAR-5 | 5.05 | 4.79 | 4.53 |
| OVCAR-8 | 5.16 | 4.77 | 4.37 |
| Renal Cancer | | | |
| 786-0 | 6.06 | 5.76 | 5.47 |
| ACHN | 6.05 | 5.77 | 5.5 |
| CAKI-1 | 5.18 | 4.83 | 4.48 |
| SN12C | 5.23 | 4.91 | 4.6 |
| TK-10 | 5.8 | 5.34 | 4.75 |
| UO-31 | 5.47 | 4.81 | * |
| Prostate Cancer | | | |
| PC-3 | 5.84 | 5.35 | 4.64 |

TABLE 3-continued

NCI multiple cell-line test for the drug MT477, results reported as molar, with maximum dose of 0.05 millimolar.

| Panel/Cell Line | $-\log_{10}GI50$ | $-\log_{10}TGI$ | $-\log_{10}LC50$ |
|---|---|---|---|
| Breast Cancer | | | |
| MCF7 | 5.75 | * | * |
| MDA-MB-231/ATCC | 6.07 | 5.76 | 5.46 |
| HS 578T | 5.18 | 4.68 | * |
| MDA-MB-435 | 5.77 | 5.27 | 4.58 |
| BT-549 | 5.45 | 4.86 | * |
| T-47D | 5.82 | 5.40 | * |

*effect not reached at maximum dose of 0.05 millimolar

Methodology: The NCI conducted a test of the MT477 drug against about 60 human cell lines, with a minimum of five concentrations of MT477 at 10-fold dilutions, with no more than $5(10)^{-5}$ molar of drug being used. A 48 hour continuous drug exposure was used, and a sulforhodamine B (SRB) protein assay was used to estimate cell viability and growth. The human tumor cell lines of the cancer screening panel were grown in RPMI 1640 medium containing 5% fetal bovine serum and 2 mM L-glutamine. Cells were inoculated into 96 well microtiter plates in 100 μL at plating densities ranging from 5,000 to 40,000 cells/well depending on the doubling time of individual cell lines. After cell inoculation, the microtiter plates are incubated at 37° C., 5% $CO_2$, 95% air, and 100% relative humidity for 24 h prior to addition of experimental drugs.

After 24 h, two plates of each cell line were fixed in situ with TCA, to represent a measurement of the cell population for each cell line at the time of drug addition (Tz). MT477 was solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 μg/ml gentamicin. Additional four, 10-fold or ½ log serial dilutions were made to provide a total of five drug concentrations plus control. Aliquots of 100 μl of these different drug dilutions were added to the appropriate microtiter wells already containing 100 μl of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air-dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 μl of 80% TCA (final concentration, 16% TCA). Using the seven absorbance measurements (time zero, (Tz), control growth, (C), and test growth in the presence of drug at the five concentration levels (Ti)), the percentage growth was calculated at each of the drug concentrations levels. Percentage growth inhibition was calculated as:

[(Ti−Tz)/(C−Tz)]×100 for concentrations for which Ti>/=Tz

[(Ti−Tz)/Tz]×100 for concentrations for which Ti<Tz.

Three dose response parameters were calculated for each experimental agent. Growth inhibition of 50% ($GI_{50}$) was calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment was calculated from [(Ti−Tz)/Tz]×100=−50. Values were calculated for each of these three parameters if the level of activity is reached; however, if the effect was not reached or was exceeded, the value for that parameter was expressed as greater or less than the maximum or minimum concentration tested.

Example 4

MT477 Family Effectively Inhibits Many Cancer Cell Types

This Example shows that MT477 is an effective drug for treating human cancer. MT477 was tested with various lung cancer cell lines, at a variety of concentrations, and effectively inhibited growth of the cancer cells, see FIGS. 1-15. Surprisingly, MT477 also, in many applications, is more potent than MT103 or cisplatin.

Methods

An independent laboratory adapted the methods of Example 3, above, to generate the data shown in FIGS. 1-15. Cell growth, however, were assessed with the MTT dye conversion assay. Descriptions of the MTT assay are provided at, for example, the :MTT Cell Assay" published by the American type Cell Culture Collection. Data was taken at 48 hours unless a 24 hour time period is indicated.

Figure 2:
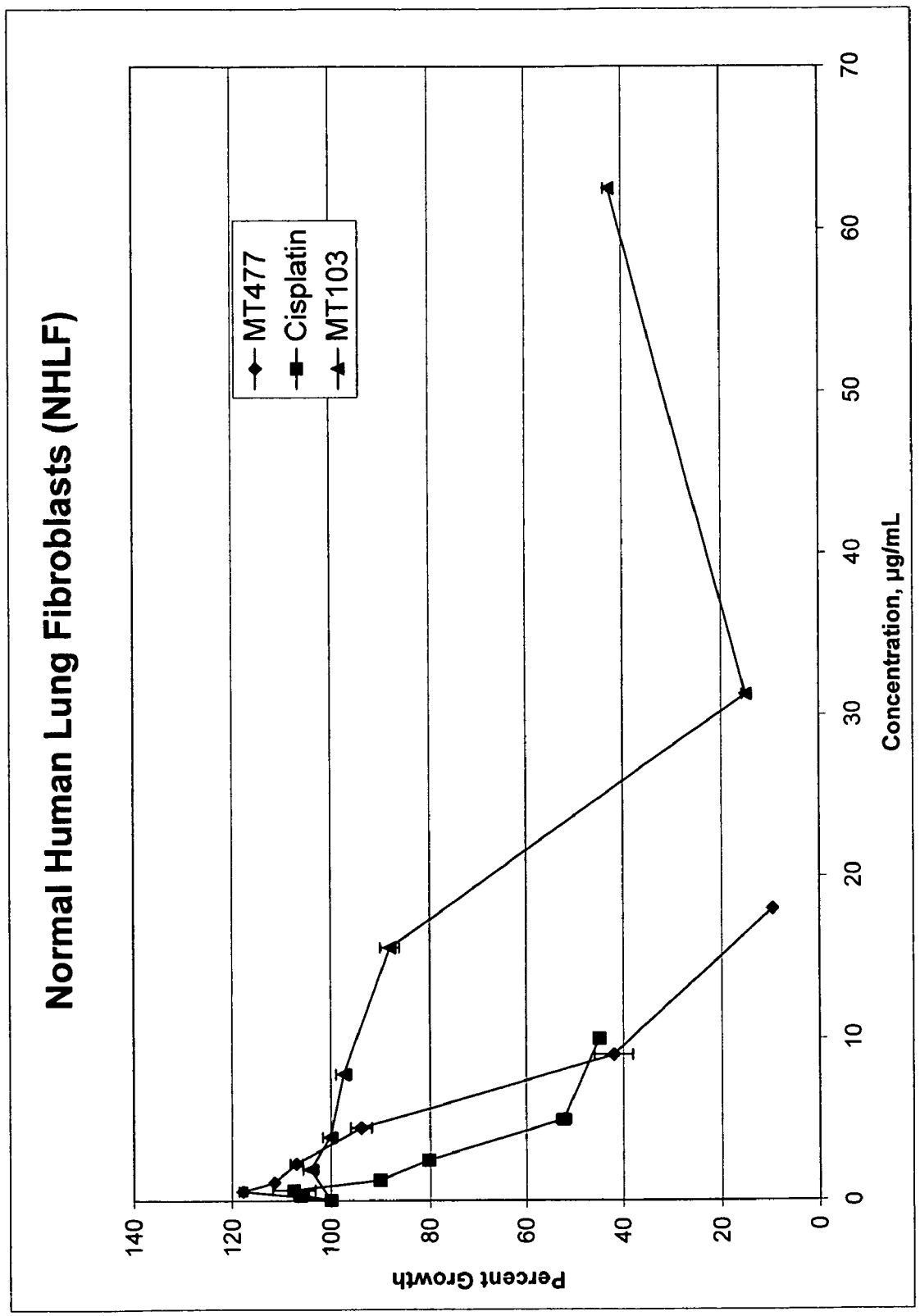
FIG. 2 is a graph of the growth response of normal human lung fibroblasts exposed to concentrations of MT477, MT103, and cisplatin that are relatively lower than those of FIG. 1.

FIGS. 1 and 2 show the response of normal human lung fibroblasts to MT103, MT477, and cisplatin. MT477 has a cytotoxicity profile that is similar to cisplatin.

Figure 3:
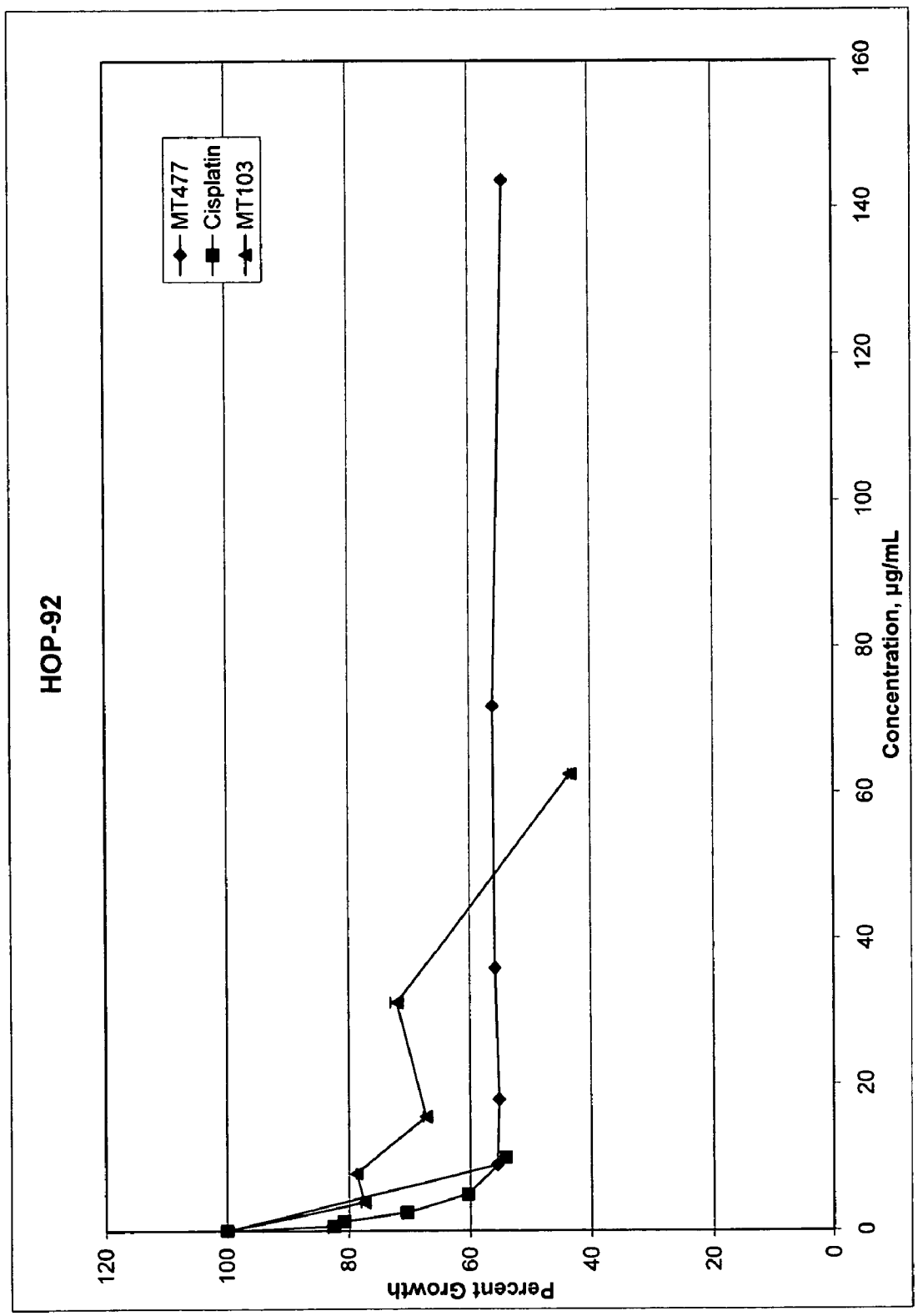
FIG. 3 is a graph of the growth response of HOP-92 cells exposed to various concentrations of MT477, MT103, and cisplatin.
Figure 4:
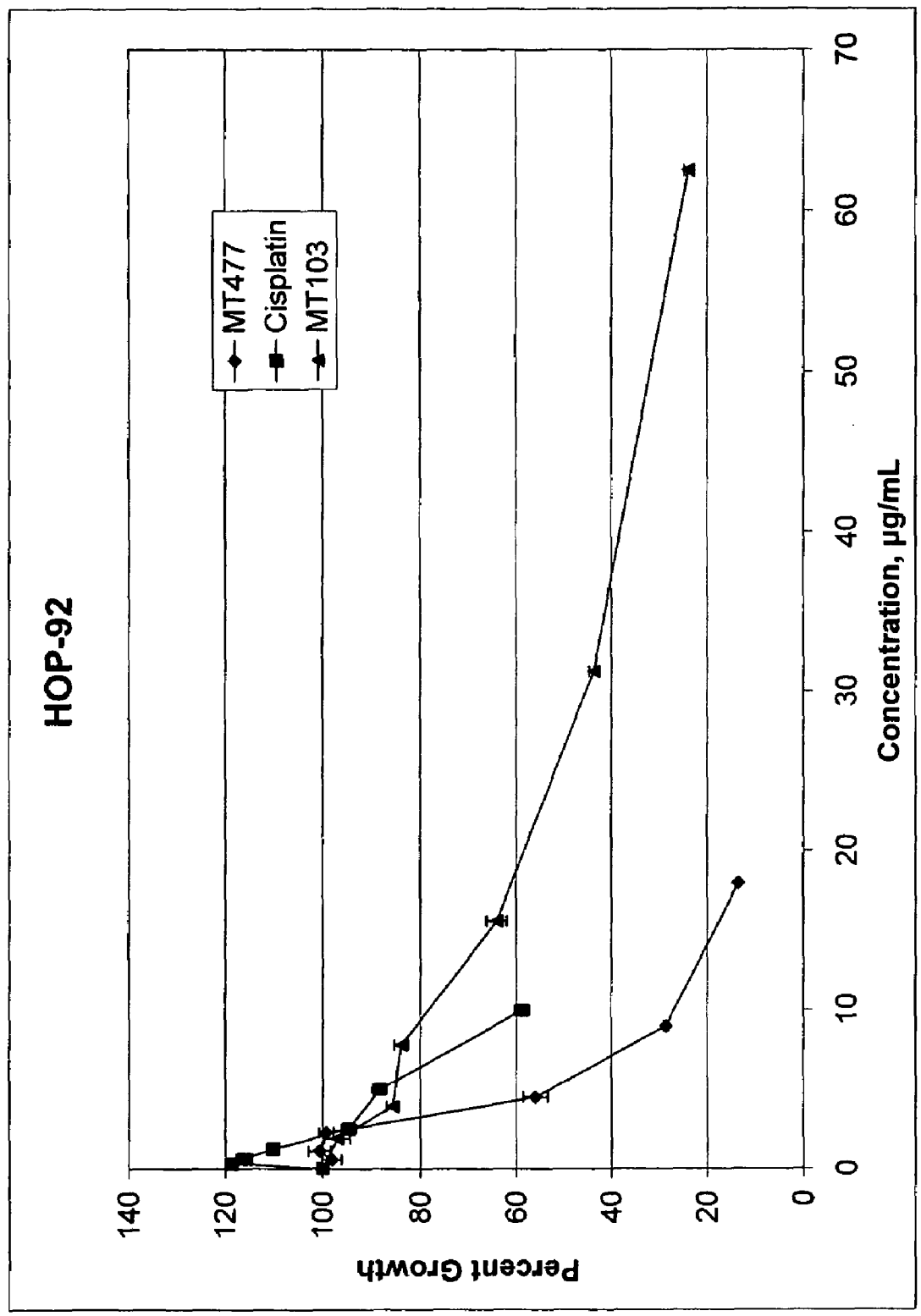
FIG. 4 is a graph of the growth response of HOP-92 cells exposed to concentrations of MT477, MT103, and cisplatin that are relatively lower than those of FIG. 3.

FIGS. 3 and 4 show the response of HOP-92 cells to MT103, MT477, and cisplatin.

Figure 5:
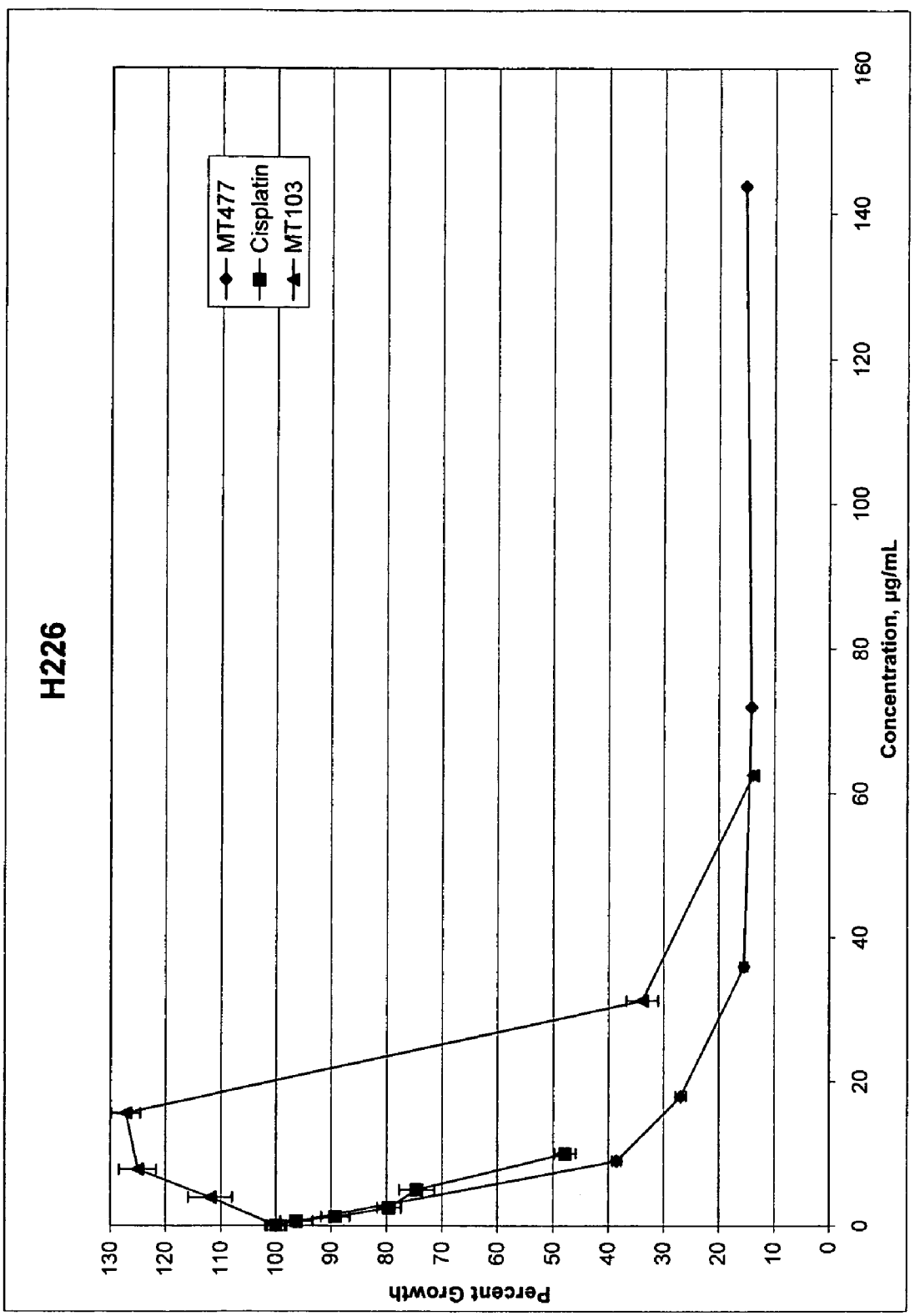
FIG. 5 is a graph of the growth response of H226 cells exposed to various concentrations of MT477, MT103, and cisplatin.

FIG. 5 shows the response of H226 cells to MT103, MT477, and cisplatin. Surprisingly, MT477 is more effective than cisplatin. HOP-92 cells and H226 cells are models for non-small cell lung cancer, and MT477 is therefore expected to be efficacious for treatment of that condition.

Figure 6:
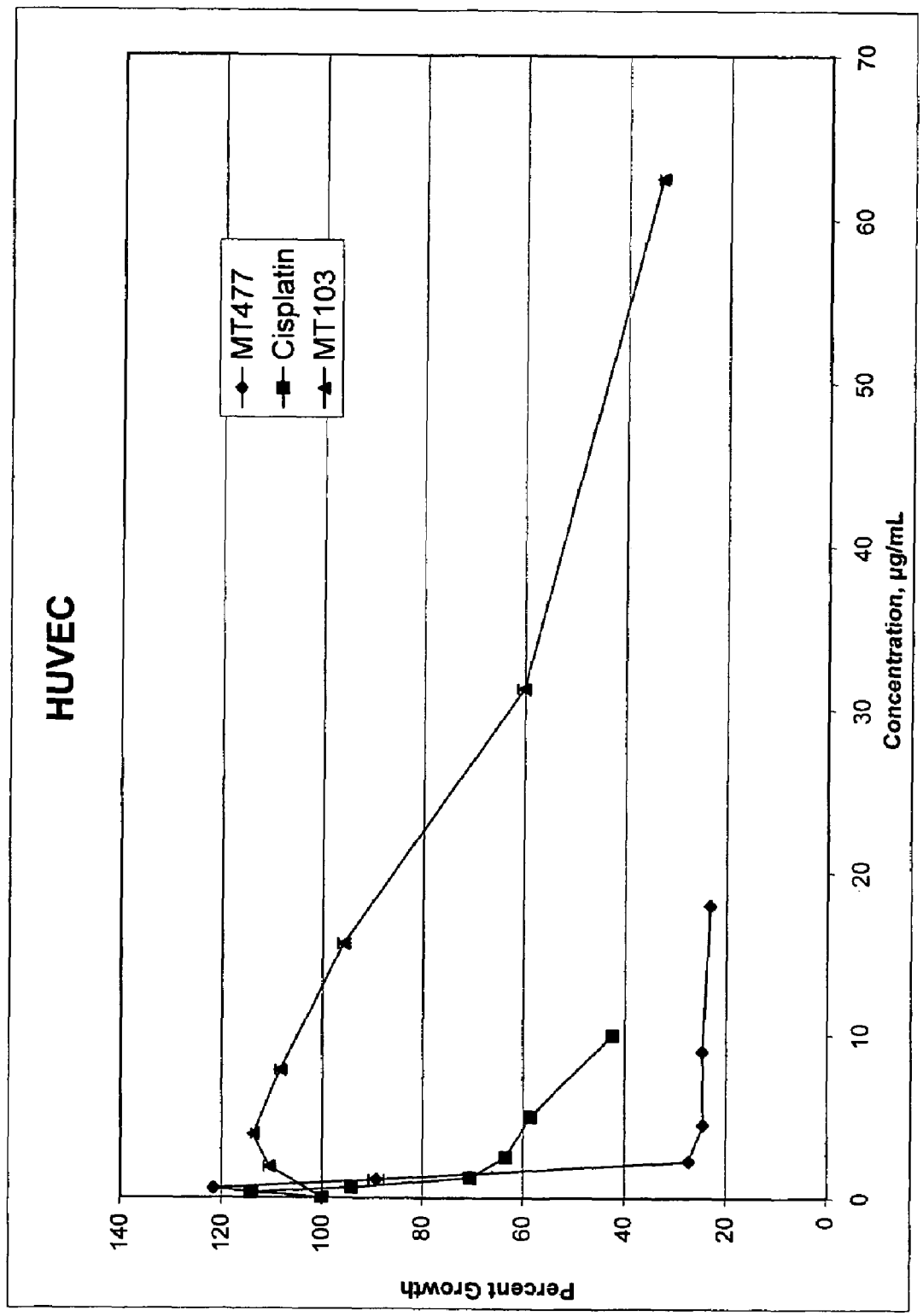
FIG. 6 is a graph of the growth response of human endothelial vein endothelial cells exposed to various concentrations of MT477, MT103, and cisplatin.

FIG. 6 shows the response of human endothelial vein cells (HUVECs) to MT103, MT477, and cisplatin. MT477 has a cytotoxicity profile that is similar to cisplatin.

Figure 7:
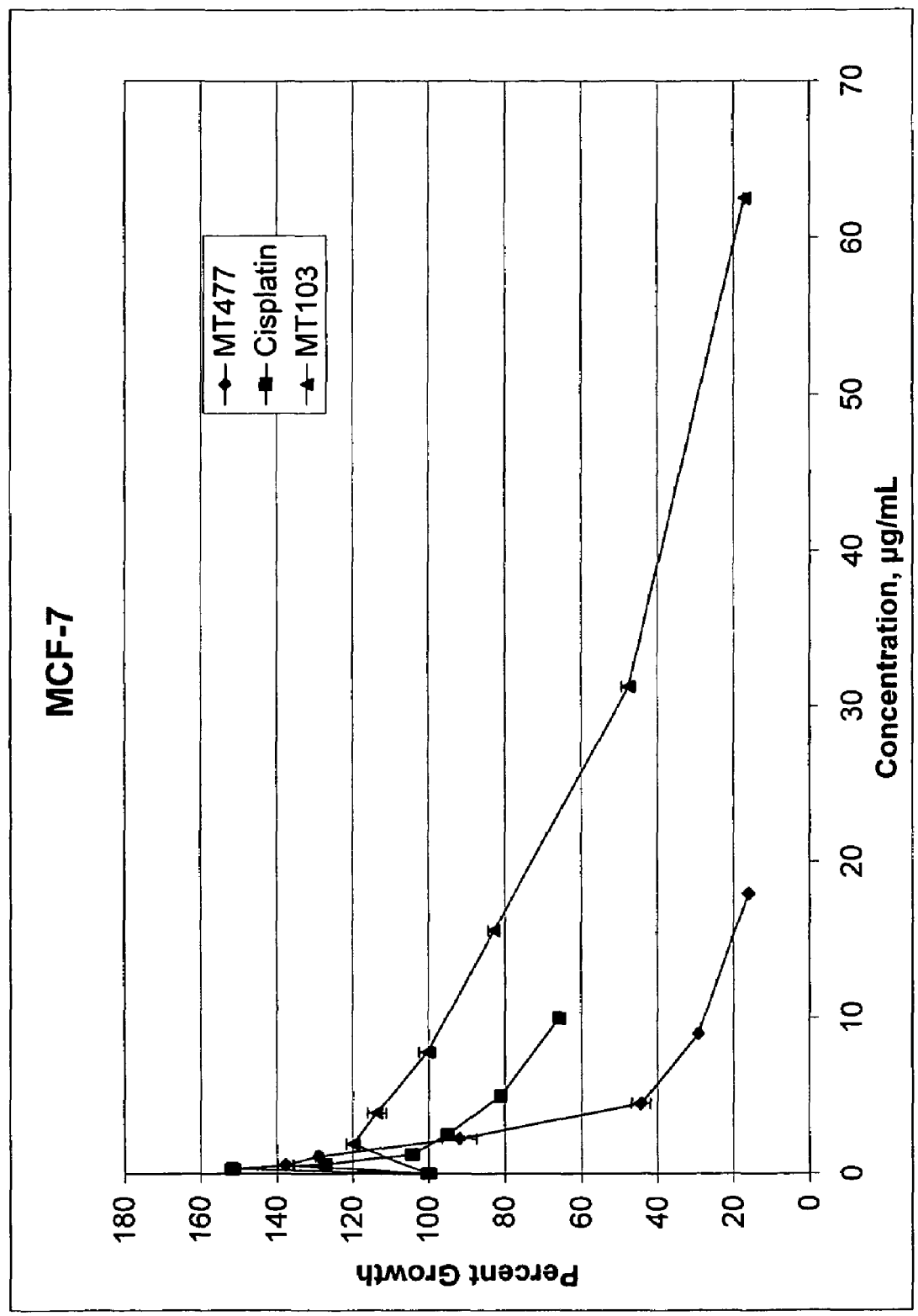
FIG. 7 is a graph of the growth response of MCF-7 cells exposed to various concentrations of MT477, MT103, and cisplatin.
Figure 8:
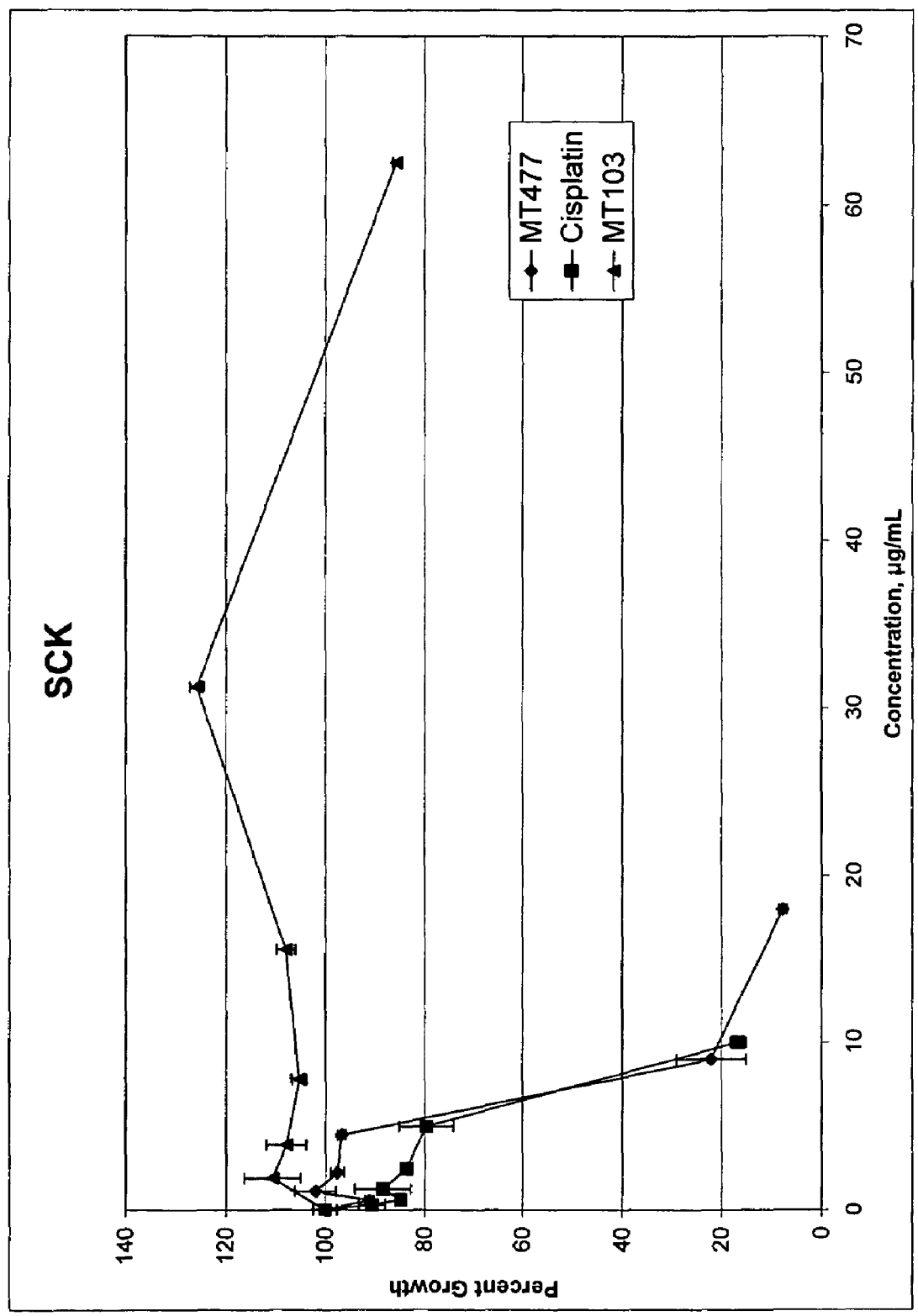
FIG. 8 is a graph of the growth response of SCK cells exposed to various concentrations of MT477, MT103, and cisplatin.

FIG. 7 shows the response of MCF-7 cells to MT103, MT477, and cisplatin. FIG. 8 shows the response of murine mammary cell lines. Surprisingly, MT477 is more effective than cisplatin. MCF-7 cells and SCK cells are models for breast cancer, and MT477 is therefore expected to be efficacious for treatment of that condition.

Figure 9:
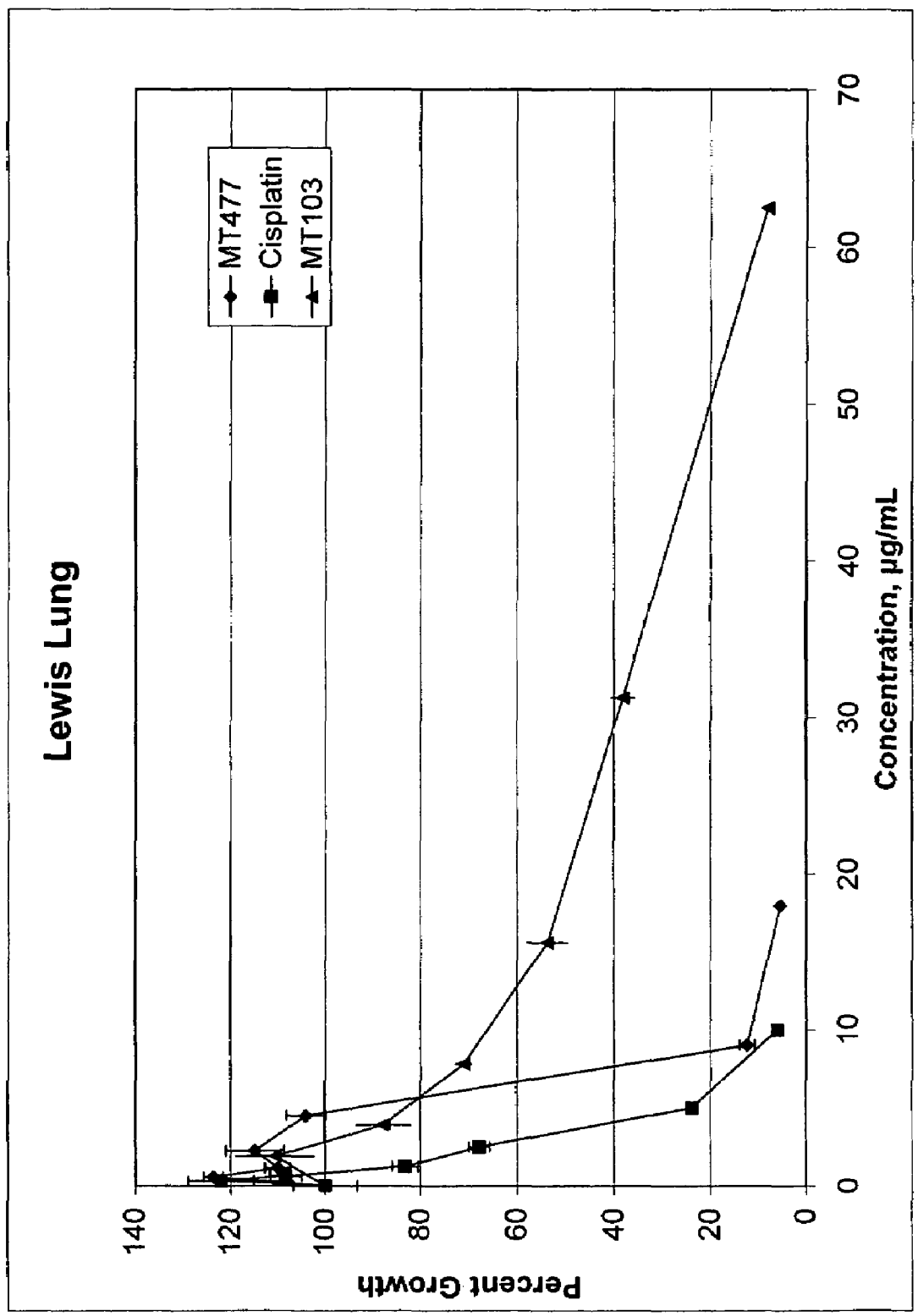
FIG. 9 is a graph of the growth response of Lewis lung cells exposed to various concentrations of MT477, MT103, and cisplatin.

FIG. 9 shows the response Lewis murine lung cells to MT103, MT477, and cisplatin.

Figure 10:
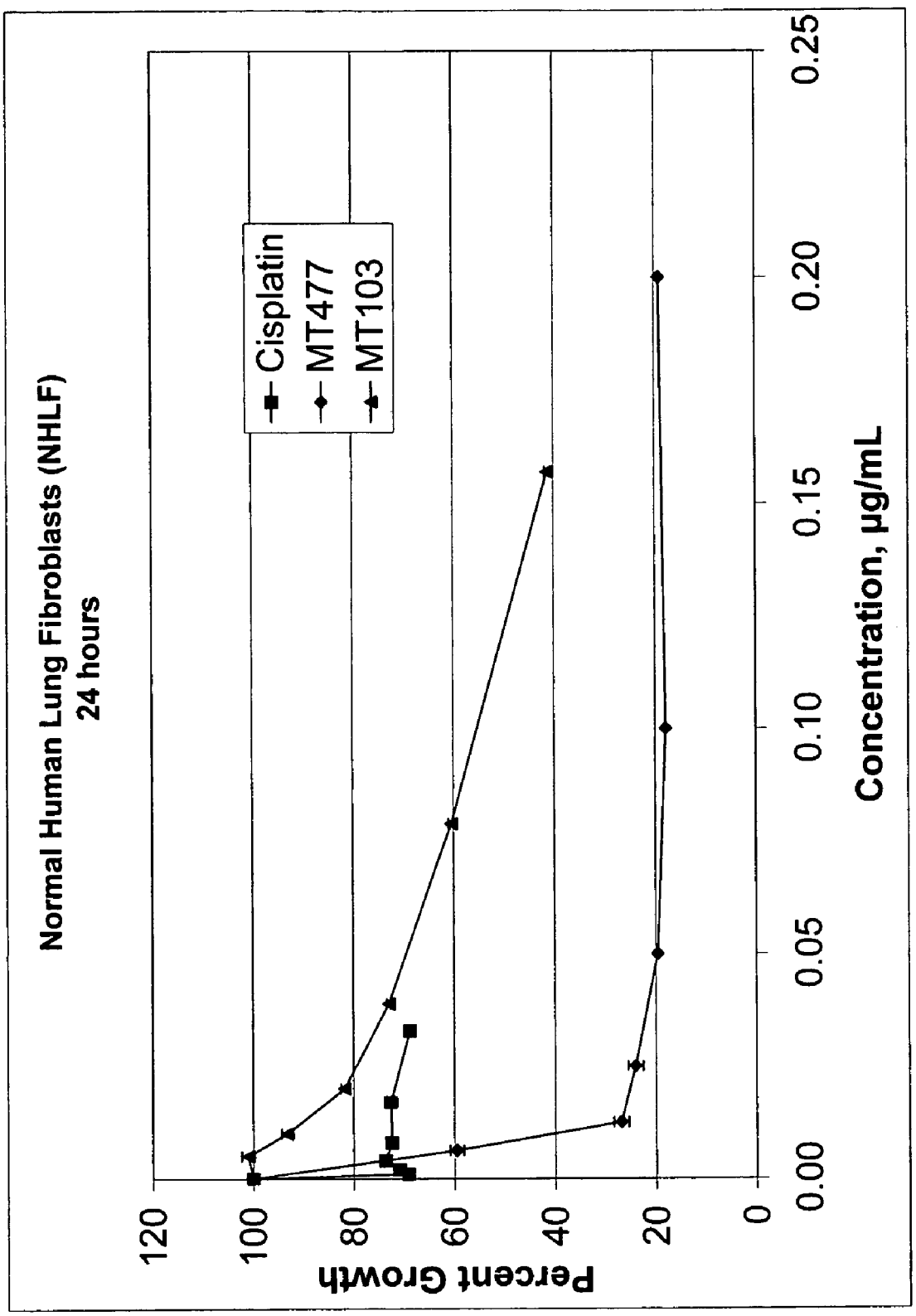
FIG. 10 is a graph of the growth human fibroblasts after 24 hours of exposure to low concentrations of cisplatin, MT477, or MT103.
Figure 11:
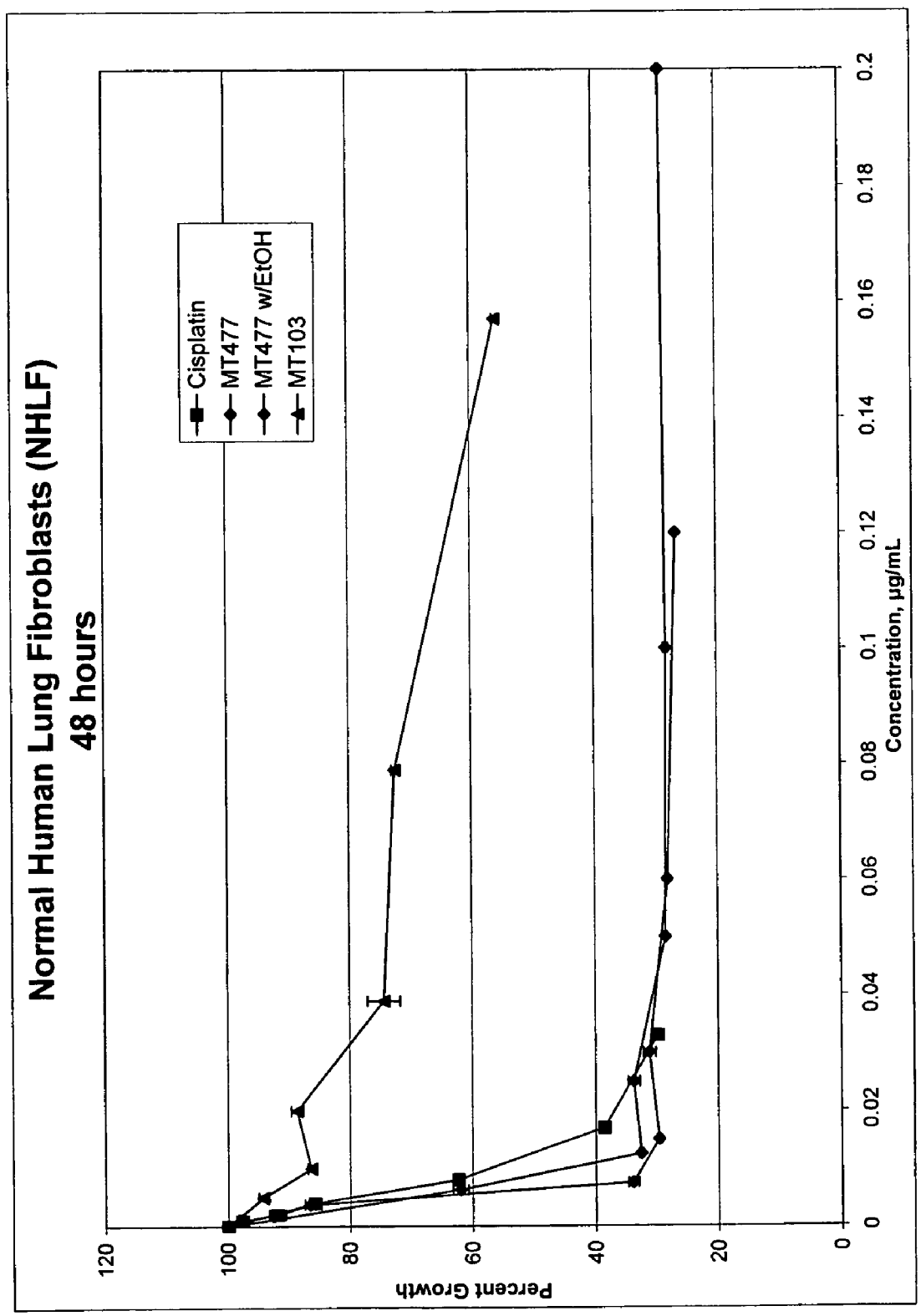
FIG. 11 is a graph of the growth human fibroblasts after 24 hours of exposure to low concentrations of cisplatin, MT477, or MT103.
Figure 12:
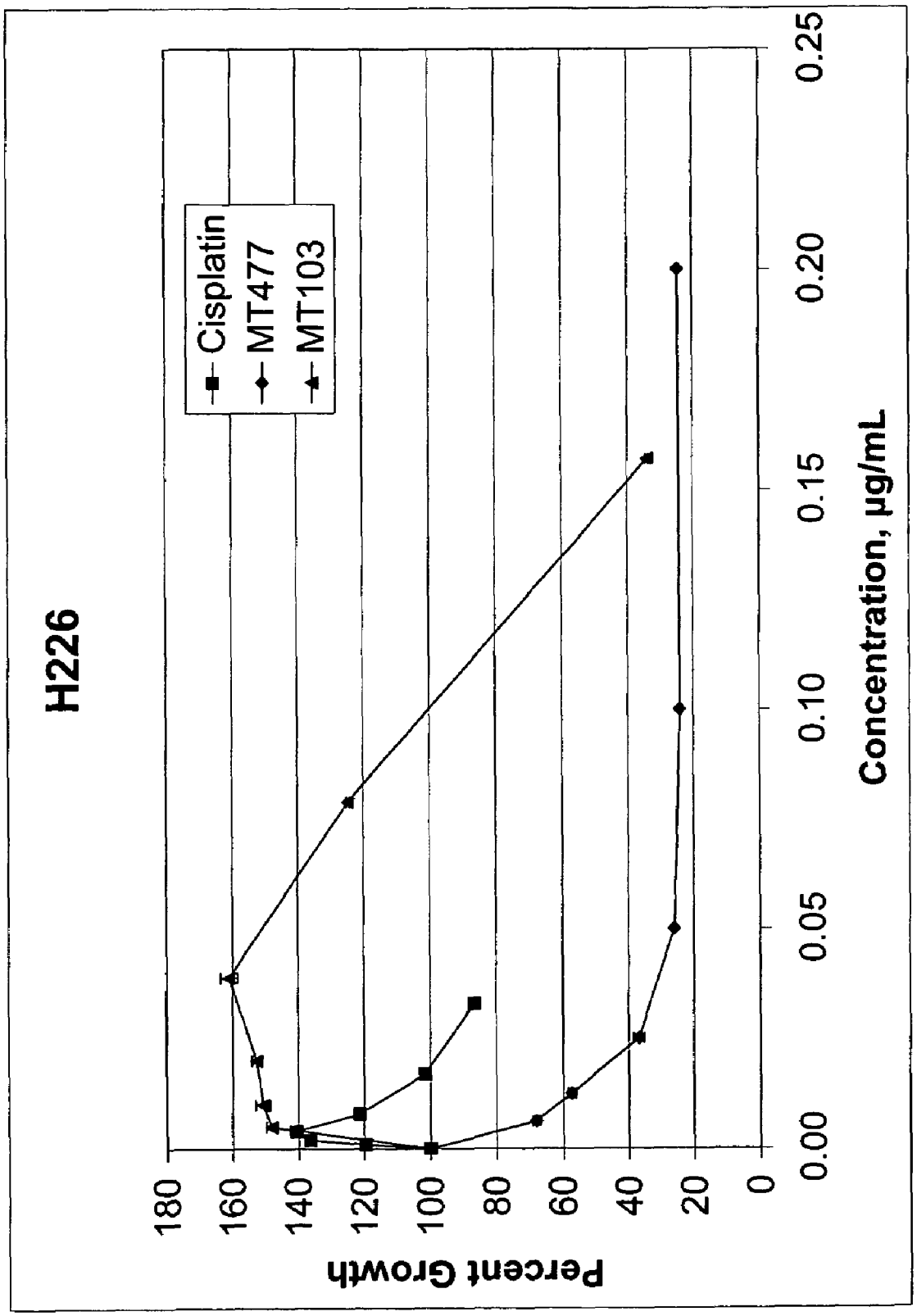
FIG. 12 is a graph of the growth response after 24 hours of H226 cells exposed to low concentrations of MT477, MT103, and Cisplatin.
Figure 13:
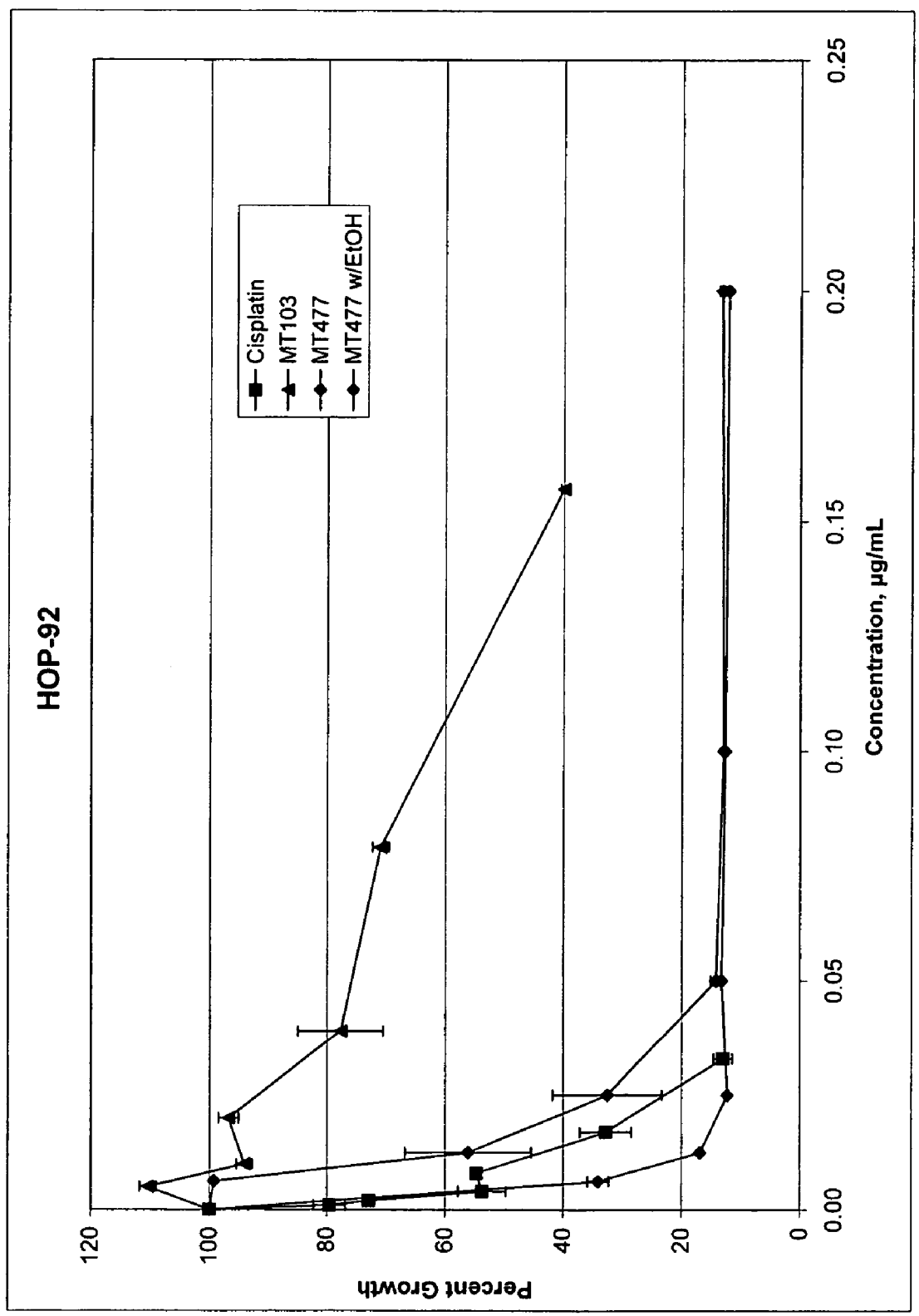
FIG. 13 is a graph of the growth response of HOP-92 cells exposed to low concentrations of MT477, MT103, and Cisplatin.

FIG. 10 shows the response of normal human lung cells at 24 and 48 hours. Surprisingly, MT477 is more effective than cisplatin. MT477 is thus effective in human and mouse cell lung lines, so that MT477 has a robust response across species.

Figure 14:
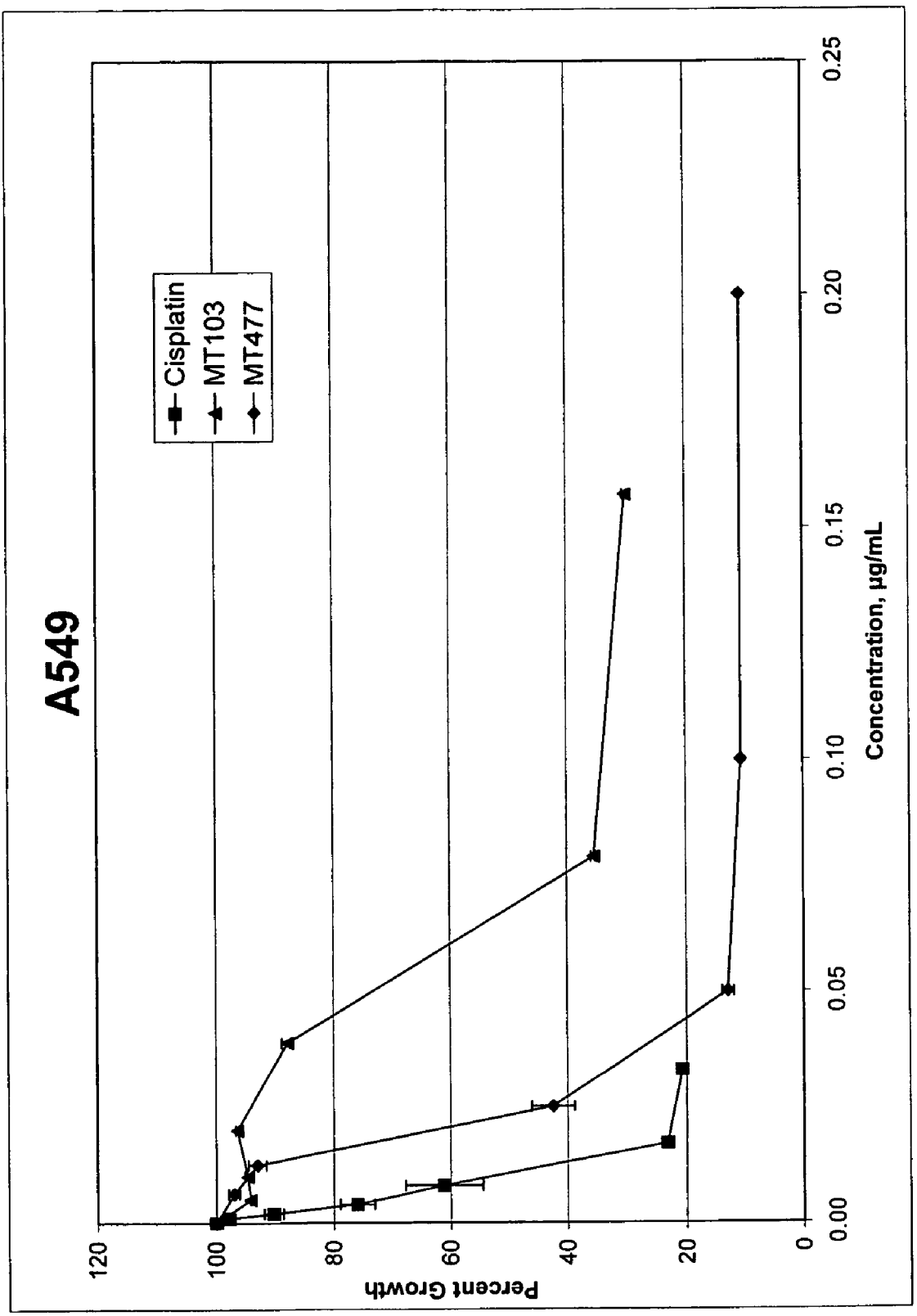
FIG. 14 is a graph of the growth response of A549 cells exposed to low concentrations of MT477, MT103, and Cisplatin.
Figure 15:
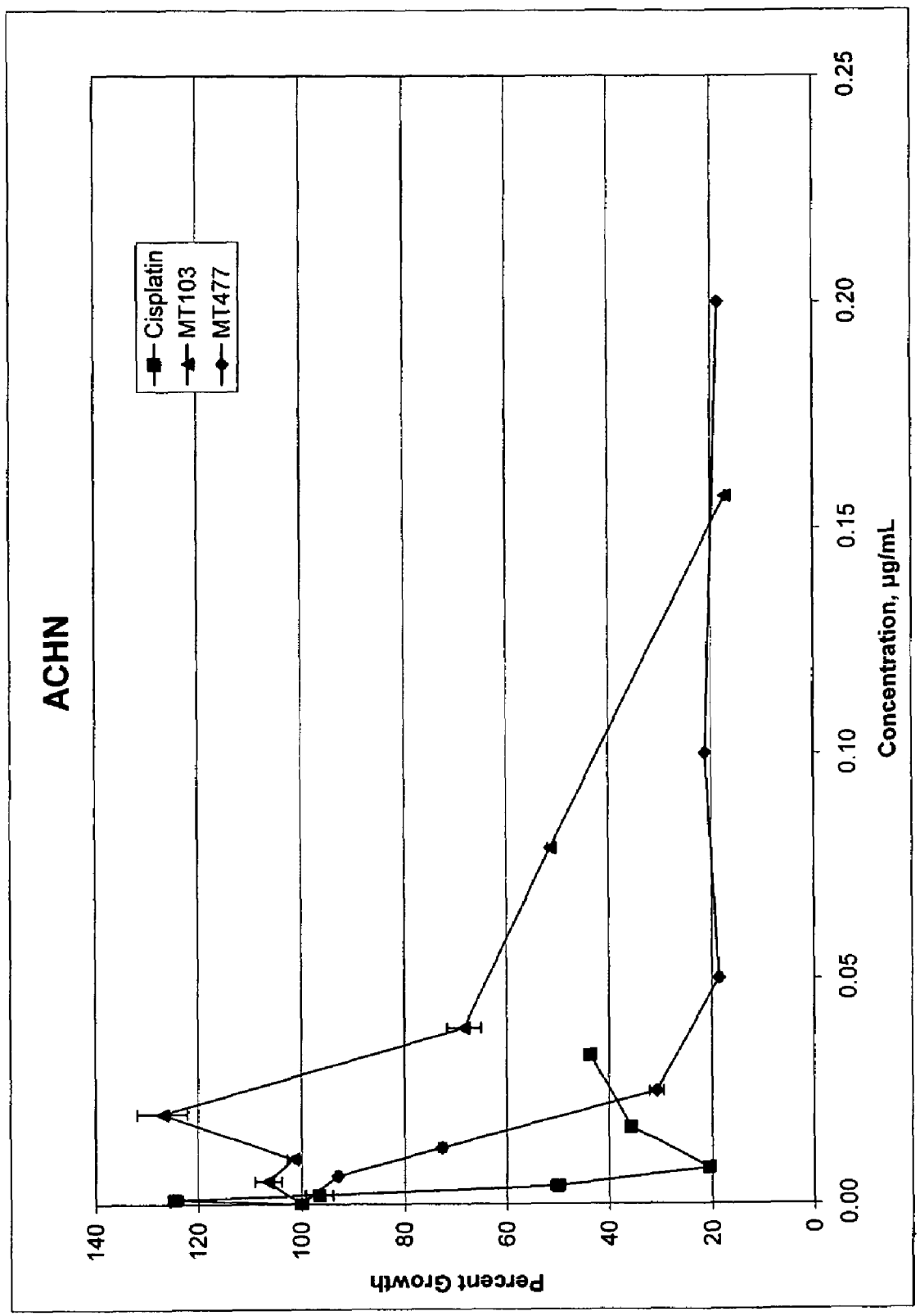
FIG. 15 is a graph of the growth response of ACHN cells exposed to low concentrations of MT477, MT103, and Cisplatin.

FIGS. 11-15 show that MT477 is effective even at very low doses, including micromolar dosages. These Figures show efficacy in H226 cells (FIG. 11), HOP-92 cells (FIG. 12), A549 cells (FIG. 13), and ACHN cells (FIG. 14).

Example 5

Analogs of MT477 Determined to be Effective Therapeutic Agents

Results of the topological computer model showed that members of the MT477 family are effective therapeutic agents. Tables 4A-4J show compounds tested with the computer model and determined to be efficacious. Various categories of efficacy were predicted. The predictions are provided only as guides and not detailed predictions of functionality. The 50% Growth Inhibition (GI50) is reported in the Tables as −log(GI50) so that higher values are relatively more efficacious than lower values, with a value of 4 or less indicating little efficacy. The MCF7 value relates to predicted activity against breast MCF7 cell line, which is predictive for breast cancer. The NCI-H460 values are predictions of efficacy against the H460 cell line, which is predictive for activity against lung cancer. The SF268 values are predictions of efficacy against the SF268 cell line, which is predictive of activity against central nervous system cancer. The H226 values predict activity against the H226 cell line, which is predictive of activity against non-small cell lung cancer. PKC Probability, PKC Activator, and PKC log(KI) refer to predictions of modulating protein kinase C (PKC) activity. AcetylCh, Probability and AcetylCh, Potency (DDT=1) refer to probabilities of affecting acetylc cholinase enzyme activity Apoptosis Probability, Apoptosis (Ind, % PKC), and Apoptosis (Caspase) refer to probabilities of being apoptotic. Antihormonal and Antihormonal (Aromatase) refer to probabilities of being antihormonal. Antimitotic, antimitotic tubulin, and antimitotic tubulin (Col) refer to potential antimitotic activity. Topoisomerase I refers to Topoisomerase activity. Pharmacological dosage and kinetics models were used to predict properties such as intestinal absorption, urinary excretion (%), nonrenal elimination, metabolites (% hep, elim,), bound in plasma (%), clearance (L/h), Vd (L), half life beta (hours), peak time (h), peak concentration (mg/L), toxicity probability, and high toxicity probability. Additional properties that were modeled and predicted are acute toxicity using the ld50 rat oral (mg/kg), toxicity of antineoplastic ld50 rat oral (mg/kg) neo, ld50 rat iv (mg/kg), HM therapeutical index, oral noel rat subchronic, oral noel rat chronic, carcinogenicity probability, carcinogenicity potency, mutagenicity probability, mutagenicity potency, neurotoxicity probability, neurotoxicity (potency), hematotoxicity probability, cytotoxicity (in micromolar), teratogenicity probability, and molecular weight. Thus PKC Probability relates to Probability to interact Protein Kinase C (PKC), PKC Activator relates to Probability to activate Protein Kinase C (PKC), PKC log (Ki) relates to interaction (activation) constant, acetylch probability relates to acetyl cholinesterase inhibition, DDT=1 elates to potency expressed relative to reference compound, in this case, DDT, apoptosis probability relates to probability of apoptosis related to PKC activation, apoptosis (caspase) relates to of apoptosis by the caspase pathway, antimitotic tubulin relates to antimitotic activity by the tubulin pathway, antimitotic tubulin (col) relates to antimitotic activity by the tubulin-colchicin pathway, clearance (L/h) relates to prediction of total clearance by a topological model I, clearance (L/h) 2 relates to prediction of total clearance by topological model II toxicity probability relates to toxicity and high-toxicity are general predictions of toxicity, LD50 relates to general model for acute toxicity, LD50-neo relates to model for antineoplastic toxicity, iv relates to intravenous, therapeutic index relates to the quotient between LD50-oral rat (mg/kg) and expected daily dose for humans in mg/day, noel relates to not observed effect level.

TABLE 4A

| Molecule | Formula | MCF7 - log(GI50) | H460 - log(GI50) | SF268 - log(GI50) | Average - log(GI50) |
|---|---|---|---|---|---|
| D10000 | 5 | 7.51 | 7.14 | 7.12 | 7.22 |
| D10000A | 6 | 7.44 | 7.1 | 7.06 | 6.98 |
| D10000B | 7 | 7.21 | 7 | 6.96 | 6.57 |
| D10000C | 8 | 5.83 | 6.12 | 6.13 | 6.97 |
| D20001 | 9 | 7.57 | 7.32 | 7.14 | 7.38 |
| D20001A | 10 | 7.47 | 7.32 | 7.11 | 7.17 |
| D20001B | 11 | 7.39 | 7.29 | 7.08 | 6.92 |
| D20001C | 12 | 7.43 | 7.29 | 7.1 | 6.79 |
| D30010 | 13 | 7.86 | 7.34 | 7.29 | 7.96 |
| D30010A | 14 | 7.76 | 7.34 | 7.25 | 7.74 |
| D40059 | 15 | 7.71 | 7.24 | 7.27 | 7.88 |
| D40059A | 16 | 7.37 | 7.09 | 7.07 | 7 |
| D40059B | 17 | 7.48 | 7.24 | 7.19 | 7.25 |
| D60015 | 18 | 7.83 | 7.42 | 7.3 | 8 |
| D60015A | 19 | 8.16 | 7.62 | 7.53 | 8.34 |
| D70017 | 20 | 8.01 | 7.51 | 7.45 | 8.01 |
| D70017A | 21 | 8.09 | 7.58 | 7.53 | 7.93 |
| D80019 | 22 | 8.17 | 7.59 | 7.49 | 8.27 |
| D80019A | 23 | 8.07 | 7.59 | 7.45 | 8.05 |
| D90002 | 24 | 7.74 | 7.34 | 7.24 | 7.82 |
| D90002A | 25 | 7.6 | 7.34 | 7.21 | 7.38 |
| DA0001 | 26 | 7.86 | 7.41 | 7.31 | 8.15 |
| DA0001A | 27 | 7.66 | 7.41 | 7.24 | 7.52 |
| DB0001 | 28 | 7.93 | 7.33 | 7.39 | 8.21 |
| DB0001A | 29 | 7.98 | 7.34 | 7.44 | 8.49 |
| DC0001 | 30 | 4 | 4 | 4 | 7.23 |
| DC0001A | 31 | 4 | 4 | 4 | 7.16 |
| DC0001B | 32 | 4 | 4 | 4 | 6.88 |
| DC0001C | 33 | 5.52 | 5.65 | 5.64 | 7.04 |
| MT477 | 2(a) | 7.42 | 7.18 | 7.11 | 8.18 |
| MT477A | 2(b) | 7.4 | 7.15 | 7.1 | 8.27 |
| MT477B | 2(c) | 7.41 | 7.17 | 7.1 | 8.13 |
| MT477C | 2(d) | 7.41 | 7.17 | 7.1 | 8.08 |
| MT477D | 2(e) | 7.41 | 7.16 | 7.09 | 7.93 |
| MT477E | 2(f) | 7.41 | 7.17 | 7.1 | 8.08 |
| MT477F | 2(g) | 7.35 | 7.09 | 7.06 | 7.73 |
| MT477-3N | 45 | 6.85 | 7.05 | 6.80 | 6.34 |
| MT477-N5 | 40 | 6.93 | 7.18 | 7.09 | 6.16 |
| MT477-N7 | 38 | 6.93 | 7.18 | 7.09 | 6.16 |
| MT477-N1 | 36 | 6.92 | 7.18 | 7.10 | 6.10 |
| MT477-N3 | 42 | 6.92 | 7.18 | 7.10 | 6.05 |
| MT477-N4 | 41 | 6.92 | 7.18 | 7.10 | 6.03 |
| MT477-N2 | 43 | 6.92 | 7.18 | 7.10 | 6.01 |
| MT477-3O | 44 | 6.83 | 7.03 | 6.75 | 6.00 |
| MT477-N6 | 39 | 6.93 | 7.18 | 7.10 | 5.99 |
| D60015A | 37 | 6.98 | 7.62 | 7.53 | 5.89 |

TABLE 4B

| Molecule | Formula | H226 - log(GI50) | PKC Probability | PKC Activator | PKC log(KI) | AcetylCh, Probability | AcetylCh, Potency (DDT = 1) |
|---|---|---|---|---|---|---|---|
| D10000 | 5 | 7.91 | Probable | Yes | 0.89 | Possible | 0.16 |
| D10000A | 6 | 7.82 | Probable | Yes | 0.77 | Possible | 0.15 |
| D10000B | 7 | 7.78 | Probable | Yes | −0.51 | No | 0.0075 |
| D10000C | 8 | 5.6 | Yes | Yes | −0.42 | No | 0.0075 |
| D20001 | 9 | 8.23 | Probable | Yes | 0.83 | Possible | 0.23 |
| D20001A | 10 | 8.23 | Yes | Yes | −1.11 | No | 0.0075 |
| D20001B | 11 | 8.21 | Yes | Yes | −1.9 | No | 0.0075 |
| D20001C | 12 | 8.21 | Yes | Yes | −1.94 | No | 0.0075 |
| D30010 | 13 | 8.23 | Possible | Yes | 2.11 | Possible | 0.24 |
| D30010A | 14 | 8.23 | Probable | Yes | −0.34 | No | 0.0075 |
| D40059 | 15 | 7.98 | Possible | Yes | 2.28 | Possible | 0.54 |
| D40059A | 16 | 7.84 | Probable | Yes | 0.25 | No | 0.0075 |
| D40059B | 17 | 7.98 | Yes | Yes | −0.63 | No | 0.0075 |
| D60015 | 18 | 8.26 | Possible | Yes | 2.43 | Possible | 0.72 |
| D60015A | 19 | 8.72 | Possible | Yes | 3.61 | Possible | 0.63 |
| D70017 | 20 | 8.46 | Possible | Yes | 3.52 | Possible | 0.88 |
| D70017A | 21 | 8.69 | Possible | Yes | 3.88 | Possible | 0.88 |
| D80019 | 22 | 8.73 | Possible | Yes | 2.83 | Possible | 0.75 |
| D80019A | 23 | 8.73 | Probable | Yes | 0.13 | No | 0.0075 |
| D90002 | 24 | 8.19 | Probable | Yes | 1.66 | Possible | 0.21 |
| D90002A | 25 | 8.19 | Probable | Yes | −1.08 | No | 0.0075 |
| DA0001 | 26 | 8.2 | Possible | Yes | 2.2 | Possible | 0.12 |
| DA0001A | 27 | 8.2 | Yes | Yes | −2.81 | No | 0.0075 |
| DB0001 | 28 | 8.16 | Possible | Yes | 3.27 | Possible | 0.44 |
| DB0001A | 29 | 8.17 | Possible | Yes | 3.67 | Possible | 0.49 |
| DC0001 | 30 | 4 | Probable | Yes | 1.7 | Possible | 0.65 |
| DC0001A | 31 | 4 | Probable | Yes | 1.66 | Possible | 0.65 |
| DC0001B | 32 | 4 | Probable | Yes | 1.31 | Possible | 0.49 |
| DC0001C | 33 | 5.04 | Yes | Yes | −0.73 | No | 0.0075 |
| MT477 | 2(a) | 7.85 | Probable | Yes | 0.23 | No | 0.0075 |
| MT477A | 2(b) | 7.75 | Probable | Yes | 1.51 | No | 0.0075 |
| MT477B | 2(c) | 7.81 | Probable | Yes | 0.59 | No | 0.0075 |
| MT477C | 2(d) | 7.83 | Probable | Yes | 0.28 | No | 0.0075 |
| MT477D | 2(e) | 7.79 | Probable | Yes | 0.3 | No | 0.0075 |
| MT477E | 2(f) | 7.83 | Probable | Yes | 0.27 | No | 0.0075 |
| MT477F | 2(g) | 7.71 | Probable | Yes | 0.24 | No | 0.0075 |
| MT477-3N | 45 | 7.79 | Yes | Yes | 0.85 | Yes | 0.00 |

TABLE 4B-continued

| Molecule | Formula | H226 - log(GI50) | PKC Probability | PKC Activator | PKC log(KI) | AcetylCh, Probability | AcetylCh, Potency (DDT = 1) |
|---|---|---|---|---|---|---|---|
| MT477-N5 | 40 | 7.85 | Probable | Yes | 0.21 | Yes | 0.00 |
| MT477-N7 | 38 | 7.85 | Probable | Yes | 0.13 | Yes | 0.00 |
| MT477-N1 | 36 | 7.85 | Probable | Yes | 0.16 | Yes | 0.00 |
| MT477-N3 | 42 | 7.85 | Probable | Yes | 0.16 | Yes | 0.00 |
| MT477-N4 | 41 | 7.85 | Probable | Yes | 0.29 | Yes | 0.00 |
| MT477-N2 | 43 | 7.85 | Probable | Yes | 0.20 | Yes | 0.00 |
| MT477-3O | 44 | 7.77 | Yes | Yes | 1.14 | Yes | 0.00 |
| MT477-N6 | 39 | 7.85 | Probable | Yes | 0.19 | Yes | 0.00 |
| D60015A | 37 | 8.72 | Possible | Yes | 3.61 | Yes | 0.00 |

TABLE 4C

| Molecule | Formula | Apoptosis Probability | Apoptosis (Ind, % PKC) | Apoptosis (Caspasa) | Antihormonal | Antihormonal (Aromatase) |
|---|---|---|---|---|---|---|
| D10000 | 5 | Yes | 0.45 | Probable | No | No |
| D10000A | 6 | Yes | 1.46 | Probable | No | No |
| D10000B | 7 | Yes | 1.46 | Probable | No | No |
| D10000C | 8 | Yes | 18.36 | Probable | No | No |
| D20001 | 9 | Yes | 15.35 | Probable | Probable | Probable |
| D20001A | 10 | Yes | 15.35 | Probable | Possible | Possible |
| D20001B | 11 | Yes | 15.35 | Probable | Possible | Possible |
| D20001C | 12 | Yes | 15.35 | Probable | Possible | Possible |
| D30010 | 13 | Yes | 15.36 | Probable | Probable | Probable |
| D30010A | 14 | Yes | 15.36 | Probable | Probable | Probable |
| D40059 | 15 | Yes | 3.57 | Probable | Probable | Probable |
| D40059A | 16 | Yes | 4.11 | Probable | Probable | Probable |
| D40059B | 17 | Yes | 3.57 | Probable | Probable | Probable |
| D60015 | 18 | Yes | 22.82 | Probable | Possible | Possible |
| D60015A | 19 | Yes | 35.4 | Yes | Probable | Probable |
| D70017 | 20 | Yes | 25.99 | Probable | Yes | Yes |
| D70017A | 21 | Yes | 22.76 | Probable | Probable | Probable |
| D80019 | 22 | Yes | 23.93 | Probable | Possible | Possible |
| D80019A | 23 | Yes | 23.93 | Probable | No | No |
| D90002 | 24 | Yes | 16.38 | Probable | Possible | Possible |
| D90002A | 25 | Yes | 16.38 | Probable | No | No |
| DA0001 | 26 | Yes | 32.28 | Probable | Probable | Probable |
| DA0001A | 27 | Yes | 32.28 | Probable | Possible | Possible |
| DB0001 | 28 | Yes | 24.67 | Probable | Probable | Probable |
| DB0001A | 29 | Yes | 24.9 | Probable | Probable | Probable |
| DC0001 | 30 | Yes | 0 | Probable | Probable | Probable |
| DC0001A | 31 | Yes | 0 | Probable | Probable | Probable |
| DC0001B | 32 | Yes | 0 | Probable | Possible | Possible |
| DC0001C | 33 | Yes | 20.17 | Probable | Possible | Possible |
| MT477 | 2(a) | Yes | 47.48 | Possible | No | No |
| MT477A | 2(b) | Yes | 51.1 | Possible | No | No |
| MT477B | 2(c) | Yes | 49.6 | Possible | No | No |
| MT477C | 2(d) | Yes | 48.51 | Possible | No | No |
| MT477D | 2(e) | Yes | 45.8 | Possible | No | No |
| MT477E | 2(f) | Yes | 49.1 | Possible | No | No |
| MT477F | 2(g) | Yes | 44.87 | Possible | No | No |
| MT477-3N | 45 | Yes | 47.48 | Yes | Possible | Probable |
| MT477-N5 | 40 | Yes | 47.48 | Yes | Possible | Probable |
| MT477-N7 | 38 | Yes | 47.48 | Yes | Possible | Probable |
| MT477-N1 | 36 | Yes | 47.48 | Yes | Possible | Probable |
| MT477-N3 | 42 | Yes | 47.48 | Yes | Possible | Probable |
| MT477-N4 | 41 | Yes | 47.48 | Yes | Possible | Probable |
| MT477-N2 | 43 | Yes | 47.48 | Yes | Possible | Probable |
| MT477-3O | 44 | Yes | 47.48 | Yes | Possible | Probable |
| MT477-N6 | 39 | Yes | 47.48 | Yes | Possible | Probable |
| D60015A | 37 | Yes | 35.40 | Yes | Possible | Probable |

TABLE 4D

| Molecule | Formula | Antimitotic | Antimitotic Tubulin | Antimitotic Tubulin (Col) | Topoisomerase I |
|---|---|---|---|---|---|
| D10000 | 5 | Yes | Probable | Probable | Probable |
| D10000A | 6 | Yes | Possible | Possible | Probable |
| D10000B | 7 | Possible | No | Possible | Yes |
| D10000C | 8 | Probable | Possible | No | Probable |
| D20001 | 9 | Probable | Possible | No | Yes |
| D20001A | 10 | Possible | Possible | No | Yes |
| D20001B | 11 | Possible | No | No | Yes |
| D20001C | 12 | Possible | No | No | Yes |
| D30010 | 13 | Yes | Yes | Yes | Probable |
| D30010A | 14 | Yes | Yes | Yes | Probable |
| D40059 | 15 | Yes | Yes | Yes | Probable |
| D40059A | 16 | Possible | Possible | Probable | Yes |
| D40059B | 17 | Yes | Yes | Yes | Probable |
| D60015 | 18 | Yes | Yes | Possible | Yes |
| D60015A | 19 | Yes | Yes | Possible | Yes |
| D70017 | 20 | Yes | Yes | Possible | Yes |
| D70017A | 21 | Yes | Yes | Possible | Yes |
| D80019 | 22 | Yes | Yes | Possible | Yes |
| D80019A | 23 | Yes | Yes | Possible | Yes |
| D90002 | 24 | Yes | Yes | Yes | Yes |
| D90002A | 25 | Yes | Probable | Probable | Yes |
| DA0001 | 26 | Yes | Yes | Yes | Yes |
| DA0001A | 27 | Yes | Probable | Probable | Yes |
| DB0001 | 28 | Yes | Yes | Yes | Probable |
| DB0001A | 29 | Yes | Yes | Yes | Probable |
| DC0001 | 30 | Yes | Yes | Yes | Probable |
| DC0001A | 31 | Yes | Yes | Yes | Probable |
| DC0001B | 32 | Yes | Probable | Probable | Probable |
| DC0001C | 33 | Yes | Yes | Possible | Probable |
| MT477 | 2(a) | Yes | Yes | Yes | Probable |
| MT477A | 2(b) | Yes | Yes | Yes | Probable |
| MT477B | 2(c) | Yes | Yes | Yes | Probable |
| MT477C | 2(d) | Yes | Yes | Yes | Probable |
| MT477D | 2(e) | Yes | Yes | Yes | Probable |
| MT477E | 2(f) | Yes | Yes | Yes | Probable |
| MT477F | 2(g) | Yes | Probable | Probable | Probable |
| MT477-3N | 45 | Probable | Probable | Possible | Yes |
| MT477-N5 | 40 | Probable | Probable | Possible | Yes |
| MT477-N7 | 38 | Probable | Probable | Possible | Yes |
| MT477-N1 | 36 | Probable | Probable | Possible | Yes |
| MT477-N3 | 42 | Probable | Probable | Possible | Yes |
| MT477-N4 | 41 | Probable | Probable | Possible | Yes |
| MT477-N2 | 43 | Probable | Probable | Possible | Yes |
| MT477-3O | 44 | Probable | Probable | Possible | Yes |
| MT477-N6 | 39 | Probable | Probable | Possible | Yes |
| D60015A | 37 | Probable | Probable | Possible | Yes |

TABLE 4E

| Molecule | Formula | Antimitotic | Antimitotic Tubulin | Antimitotic Tubulin (Col) | Topoisomerase I |
|---|---|---|---|---|---|
| D10000 | 5 | Yes | Probable | Probable | Probable |
| D10000A | 6 | Yes | Possible | Possible | Probable |
| D10000B | 7 | Possible | No | Possible | Yes |
| D10000C | 8 | Probable | Possible | No | Probable |
| D20001 | 9 | Probable | Possible | No | Yes |
| D20001A | 10 | Possible | Possible | No | Yes |
| D20001B | 11 | Possible | No | No | Yes |
| D20001C | 12 | Possible | No | No | Yes |
| D30010 | 13 | Yes | Yes | Yes | Probable |
| D30010A | 14 | Yes | Yes | Yes | Probable |
| D40059 | 15 | Yes | Yes | Yes | Probable |
| D40059A | 16 | Possible | Possible | Probable | Yes |
| D40059B | 17 | Yes | Yes | Yes | Probable |
| D60015 | 18 | Yes | Yes | Possible | Yes |
| D60015A | 19 | Yes | Yes | Possible | Yes |
| D70017 | 20 | Yes | Yes | Possible | Yes |
| D70017A | 21 | Yes | Yes | Possible | Yes |
| D80019 | 22 | Yes | Yes | Possible | Yes |
| D80019A | 23 | Yes | Yes | Possible | Yes |

TABLE 4E-continued

| Molecule | Formula | Antimitotic | Antimitotic Tubulin | Antimitotic Tubulin (Col) | Topoisomerase I |
|---|---|---|---|---|---|
| D90002 | 24 | Yes | Yes | Yes | Yes |
| D90002A | 25 | Yes | Probable | Probable | Yes |
| DA0001 | 26 | Yes | Yes | Yes | Yes |
| DA0001A | 27 | Yes | Probable | Probable | Yes |
| DB0001 | 28 | Yes | Yes | Yes | Probable |
| DB0001A | 29 | Yes | Yes | Yes | Probable |
| DC0001 | 30 | Yes | Yes | Yes | Probable |
| DC0001A | 31 | Yes | Yes | Yes | Probable |
| DC0001B | 32 | Yes | Probable | Probable | Probable |
| DC0001C | 33 | Yes | Yes | Possible | Probable |
| MT477 | 2(a) | Yes | Yes | Yes | Probable |
| MT477A | 2(b) | Yes | Yes | Yes | Probable |
| MT477B | 2(c) | Yes | Yes | Yes | Probable |
| MT477C | 2(d) | Yes | Yes | Yes | Probable |
| MT477D | 2(e) | Yes | Yes | Yes | Probable |
| MT477E | 2(f) | Yes | Yes | Yes | Probable |
| MT477F | 2(g) | Yes | Probable | Probable | Probable |
| MT477-3N | 45 | Probable | Probable | Possible | Yes |
| MT477-N5 | 40 | Probable | Probable | Possible | Yes |
| MT477-N7 | 38 | Probable | Probable | Possible | Yes |
| MT477-N1 | 36 | Probable | Probable | Possible | Yes |
| MT477-N3 | 42 | Probable | Probable | Possible | Yes |
| MT477-N4 | 41 | Probable | Probable | Possible | Yes |
| MT477-N2 | 43 | Probable | Probable | Possible | Yes |
| MT477-3O | 44 | Probable | Probable | Possible | Yes |
| MT477-N6 | 39 | Probable | Probable | Possible | Yes |
| D60015A | 37 | Probable | Probable | Possible | Yes |

TABLE 4F

| Molecule | Formula | Clearance (L/h) | Clearance (L/h) 2 | Vd (L) | Half Life Beta (hours) | Peak Time (h) |
|---|---|---|---|---|---|---|
| D10000 | 5 | 85.96 | 62.22 | 1387.96 | 71.2 | 2.66 |
| D10000A | 6 | 73.18 | 56.48 | 1133.68 | 82.16 | 2.81 |
| D10000B | 7 | 63.42 | 56.01 | 177.84 | 38.99 | 2.55 |
| D10000C | 8 | 72.12 | 59.58 | 150.39 | 55.44 | 2.45 |
| D20001 | 9 | 36.83 | 61.62 | 971.41 | 63.01 | 2.94 |
| D20001A | 10 | 37.29 | 61.62 | 608.51 | 34.22 | 2.74 |
| D20001B | 11 | 35.97 | 61.85 | 545.37 | 31.35 | 2.7 |
| D20001C | 12 | 35.82 | 61.85 | 628.87 | 36.39 | 2.74 |
| D30010 | 13 | 86.12 | 67.35 | 2703.61 | 140.21 | 3.26 |
| D30010A | 14 | 86.56 | 67.35 | 1705.18 | 76.14 | 3.08 |
| D40059 | 15 | 109.58 | 68.93 | 4017.79 | 146.68 | 2.88 |
| D40059A | 16 | 68.92 | 59.35 | 1764.77 | 87.5 | 2.96 |
| D40059B | 17 | 111.17 | 68.93 | 462.79 | 32.69 | 2.58 |
| D60015 | 18 | 37.2 | 58.52 | 2122.54 | 215.36 | 2.76 |
| D60015A | 19 | 47.9 | 71.55 | 880.59 | 488.53 | 2.59 |
| D70017 | 20 | 38.09 | 62.86 | 3918.53 | 275.35 | 2.72 |
| D70017A | 21 | 45.2 | 66.68 | 941.82 | 353.1 | 2.7 |
| D80019 | 22 | 34.49 | 62.9 | 3028.59 | 235.4 | 2.74 |
| D80019A | 23 | 34.86 | 62.9 | 1922.44 | 127.84 | 2.62 |
| D90002 | 24 | 63.82 | 59.68 | 1675.24 | 103.25 | 3.18 |
| D90002A | 25 | 64.58 | 59.68 | 860.79 | 45.19 | 2.99 |
| DA0001 | 26 | 56.15 | 62.49 | 2773.38 | 168.12 | 3.02 |
| DA0001A | 27 | 56.99 | 62.49 | 923.98 | 53.07 | 2.69 |
| DB0001 | 28 | 94.23 | 68.5 | 4806.35 | 166.93 | 2.74 |
| DB0001A | 29 | 127.85 | 71.54 | 967.83 | 151.18 | 2.51 |
| DC0001 | 30 | 30.8 | 66 | 1405.26 | 28.42 | 2.74 |
| DC0001A | 31 | 42.59 | 65.32 | 360.41 | 27.1 | 2.44 |
| DC0001B | 32 | 42.81 | 57.57 | 1436.61 | 30.55 | 2.84 |
| DC0001C | 33 | 62.86 | 71.65 | 283.47 | 16.44 | 2.04 |
| MT477 | 2(a) | 78.17 | 57.67 | 501.55 | 72.11 | 2.15 |
| MT477A | 2(b) | 104.88 | 51.86 | 622.7 | 22.4 | 1.92 |
| MT477B | 2(c) | 83.85 | 54.69 | 500.41 | 73.71 | 2.2 |
| MT477C | 2(d) | 79.15 | 53.71 | 457.93 | 69.55 | 2.29 |
| MT477D | 2(e) | 72.22 | 53.59 | 293.99 | 77.31 | 2.43 |
| MT477E | 2(f) | 77.98 | 54.69 | 447.19 | 69.49 | 2.29 |
| MT477F | 2(g) | 68.02 | 50.08 | 463.04 | 75.51 | 2.14 |
| MT477-3N | 45 | 5.74 | 67.83 | 57.56 | 28.98 | 8.67 |
| MT477-N5 | 40 | 9.68 | 78.24 | 57.67 | 48.15 | 67.23 |
| MT477-N7 | 38 | 6.15 | 78.23 | 57.67 | 61.48 | 67.50 |
| MT477-N1 | 36 | 9.65 | 78.18 | 57.67 | 59.57 | 71.42 |
| MT477-N3 | 42 | 11.72 | 78.20 | 57.67 | 54.12 | 69.53 |
| MT477-N4 | 41 | 12.49 | 78.22 | 57.67 | 48.11 | 67.83 |
| MT477-N2 | 43 | 10.50 | 78.21 | 57.67 | 56.95 | 68.70 |
| MT47T-3O | 44 | 5.01 | 66.50 | 58.00 | 25.19 | 6.31 |
| MT477-N6 | 39 | 7.84 | 78.22 | 57.67 | 64.77 | 68.15 |
| D60015A | 37 | 83.60 | 47.90 | 71.55 | 66.41 | 488.53 |

TABLE 4G

| Molecule | Formula | Peak Concentration(mg/L) | Toxicity Probability | High Toxicity Probability | LD50 rat Oral (mg/kg) | LD50 rat Oral (mg/kg)Neo |
|---|---|---|---|---|---|---|
| D10000 | 5 | 0.03 | No | No | 978.06 | 2533.45 |
| D10000A | 6 | 0.04 | No | No | 992.21 | 2334.36 |
| D10000B | 7 | 0.07 | No | No | 1032.04 | 2809.78 |

TABLE 4G-continued

| Molecule | Formula | Peak Concentration(mg/L) | Toxicity Probability | High Toxicity Probability | LD50 rat Oral (mg/kg) | LD50 rat Oral (mg/kg)Neo |
|---|---|---|---|---|---|---|
| D10000C | 8 | 0.11 | No | No | 578.82 | 2764.84 |
| D20001 | 9 | 0.04 | No | No | 1238.74 | 3608.94 |
| D20001A | 10 | 0.06 | No | No | 1445.63 | 4206.33 |
| D20001B | 11 | 0.07 | No | No | 1380.61 | 4480.59 |
| D20001C | 12 | 0.06 | No | No | 1176.53 | 4305.94 |
| D30010 | 13 | 0.01 | No | No | 1253.91 | 3582.76 |
| D30010A | 14 | 0.02 | No | No | 1464.82 | 4233.95 |
| D40059 | 15 | 0.01 | No | No | 661.94 | 9378.14 |
| D40059A | 16 | 0.03 | No | No | 716.61 | 3074.28 |
| D40059B | 17 | 0.04 | No | No | 1185.71 | 4077.87 |
| D60015 | 18 | 0.02 | No | No | 975.86 | 3125.16 |
| D60015A | 19 | 0.01 | No | No | 1065.77 | 3410.36 |
| D70017 | 20 | 0.01 | No | No | 753.11 | 3543.1 |
| D70017A | 21 | 0.01 | No | No | 701.54 | 3043.33 |
| D80019 | 22 | 0.02 | No | No | 675.1 | 3151.73 |
| D80019A | 23 | 0.03 | No | No | 786.88 | 3714.39 |
| D90002 | 24 | 0.02 | No | No | 1357.9 | 3293.27 |
| D90002A | 25 | 0.05 | No | No | 1436.58 | 3564.71 |
| DA0001 | 26 | 0.02 | No | No | 1535.54 | 4006.73 |
| DA0001A | 27 | 0.04 | No | No | 2053.37 | 5073.57 |
| DB0001 | 28 | 0.01 | No | No | 657.36 | 3241.62 |
| DB0001A | 29 | 0.01 | No | No | 648.13 | 3438.3 |
| DC0001 | 30 | 0.01 | No | No | 1612.73 | 3184.18 |
| DC0001A | 31 | 0.01 | No | No | 1515.58 | 3103.11 |
| DC0001B | 32 | 0.02 | No | No | 1245.3 | 2680.57 |
| DC0001C | 33 | 0.19 | No | No | 854.79 | 3880.65 |
| MT477 | 2(a) | 0.04 | No | No | 1636.47 | 3032.57 |
| MT477A | 2(b) | 0.04 | No | No | 3447.26 | 3307.09 |
| MT477B | 2(c) | 0.04 | No | No | 1867.49 | 2967.2 |
| MT477C | 2(d) | 0.04 | No | No | 1548.99 | 2833.43 |
| MT477D | 2(e) | 0.04 | No | No | 1597.08 | 2998.51 |
| MT477E | 2(f) | 0.04 | No | No | 1548 | 2836.98 |
| MT477F | 2(g) | 0.05 | No | No | 1581.77 | 2947.49 |
| MT477-3N | 45 | 67.83 | 57.56 | 28.98 | 8.67 | 1.66 |
| MT477-N5 | 40 | 78.24 | 57.67 | 48.15 | 67.23 | 2.14 |
| MT477-N7 | 38 | 78.23 | 57.67 | 61.48 | 67.50 | 2.14 |
| MT477-N1 | 36 | 78.18 | 57.67 | 59.57 | 71.42 | 2.15 |
| MT477-N3 | 42 | 78.20 | 57.67 | 54.12 | 69.53 | 2.15 |
| MT477-N4 | 41 | 78.22 | 57.67 | 48.11 | 67.83 | 2.14 |
| MT477-N2 | 43 | 78.21 | 57.67 | 56.95 | 68.70 | 2.14 |
| MT477-3O | 44 | 66.50 | 58.00 | 25.19 | 6.31 | 1.57 |
| MT477-N6 | 39 | 78.22 | 57.67 | 64.77 | 68.15 | 2.14 |
| D60015A | 37 | 47.90 | 71.55 | 66.41 | 488.53 | 2.59 |

TABLE 4H

| Molecule | Formula | Peak Concentration(mg/L) | Toxicity Probability | High Toxicity Probability | LD50 rat Oral (mg/kg) | LD50 rat Oral (mg/kg)Neo |
|---|---|---|---|---|---|---|
| D10000 | 5 | 0.03 | No | No | 978.06 | 2533.45 |
| D10000A | 6 | 0.04 | No | No | 992.21 | 2334.36 |
| D10000B | 7 | 0.07 | No | No | 1032.04 | 2809.78 |
| D10000C | 8 | 0.11 | No | No | 578.82 | 2764.84 |
| D20001 | 9 | 0.04 | No | No | 1238.74 | 3608.94 |
| D20001A | 10 | 0.06 | No | No | 1445.63 | 4206.33 |
| D20001B | 11 | 0.07 | No | No | 1380.61 | 4480.59 |
| D20001C | 12 | 0.06 | No | No | 1176.53 | 4305.94 |
| D30010 | 13 | 0.01 | No | No | 1253.91 | 3582.76 |
| D30010A | 14 | 0.02 | No | No | 1464.82 | 4233.95 |
| D40059 | 15 | 0.01 | No | No | 661.94 | 9378.14 |
| D40059A | 16 | 0.03 | No | No | 716.61 | 3074.28 |
| D40059B | 17 | 0.04 | No | No | 1185.71 | 4077.87 |
| D60015 | 18 | 0.02 | No | No | 975.86 | 3125.16 |
| D60015A | 19 | 0.01 | No | No | 1065.77 | 3410.36 |
| D70017 | 20 | 0.01 | No | No | 753.11 | 3543.1 |
| D70017A | 21 | 0.01 | No | No | 701.54 | 3043.33 |
| D80019 | 22 | 0.02 | No | No | 675.1 | 3151.73 |
| D80019A | 23 | 0.03 | No | No | 786.88 | 3714.39 |
| D90002 | 24 | 0.02 | No | No | 1357.9 | 3293.27 |
| D90002A | 25 | 0.05 | No | No | 1436.58 | 3564.71 |
| DA0001 | 26 | 0.02 | No | No | 1535.54 | 4006.73 |

TABLE 4H-continued

| Molecule | Formula | Peak Concentration(mg/L) | Toxicity Probability | High Toxicity Probability | LD50 rat Oral (mg/kg) | LD50 rat Oral (mg/kg)Neo |
|---|---|---|---|---|---|---|
| DA0001A | 27 | 0.04 | No | No | 2053.37 | 5073.57 |
| DB0001 | 28 | 0.01 | No | No | 657.36 | 3241.62 |
| DB0001A | 29 | 0.01 | No | No | 648.13 | 3438.3 |
| DC0001 | 30 | 0.01 | No | No | 1612.73 | 3184.18 |
| DC0001A | 31 | 0.01 | No | No | 1515.58 | 3103.11 |
| DC0001B | 32 | 0.02 | No | No | 1245.3 | 2680.57 |
| DC0001C | 33 | 0.19 | No | No | 854.79 | 3880.65 |
| MT477 | 2(a) | 0.04 | No | No | 1636.47 | 3032.57 |
| MT477A | 2(b) | 0.04 | No | No | 3447.26 | 3307.09 |
| MT477B | 2(c) | 0.04 | No | No | 1867.49 | 2967.2 |
| MT477C | 2(d) | 0.04 | No | No | 1548.99 | 2833.43 |
| MT477D | 2(e) | 0.04 | No | No | 1597.08 | 2998.51 |
| MT477E | 2(f) | 0.04 | No | No | 1548 | 2836.98 |
| MT477F | 2(g) | 0.05 | No | No | 1581.77 | 2947.49 |
| MT477-3N | 45 | 67.83 | 57.56 | 28.98 | 8.67 | 1.66 |
| MT477-N5 | 40 | 78.24 | 57.67 | 48.15 | 67.23 | 2.14 |
| MT477-N7 | 38 | 78.23 | 57.67 | 61.48 | 67.50 | 2.14 |
| MT477-N1 | 36 | 78.18 | 57.67 | 59.57 | 71.42 | 2.15 |
| MT477-N3 | 42 | 78.20 | 57.67 | 54.12 | 69.53 | 2.15 |
| MT477-N4 | 41 | 78.22 | 57.67 | 48.11 | 67.83 | 2.14 |
| MT477-N2 | 43 | 78.21 | 57.67 | 56.95 | 68.70 | 2.14 |
| MT477-3O | 44 | 66.50 | 58.00 | 25.19 | 6.31 | 1.57 |
| MT477-N6 | 39 | 78.22 | 57.67 | 64.77 | 68.15 | 2.14 |
| D60015A | 37 | 47.90 | 71.55 | 66.41 | 488.53 | 2.59 |

TABLE 4I

| Molecule | Formula | Carcinogenicity (Potency) | Mutagenicity Probability | Mutagenicity Potency | Neurotoxicity (Prob.) | Neurotoxicity (Potency) |
|---|---|---|---|---|---|---|
| D10000 | 5 | 0.005 | No | 0.005 | No | 0.0075 |
| D10000A | 6 | 0.005 | No | 0.005 | No | 0.0075 |
| D10000B | 7 | 0.005 | No | 0.005 | No | 0.0075 |
| D10000C | 8 | 0.005 | No | 0.005 | No | 0.0075 |
| D20001 | 9 | 0.005 | No | 0.005 | No | 0.0075 |
| D20001A | 10 | 0.005 | No | 0.005 | No | 0.0075 |
| D20001B | 11 | 0.005 | No | 0.005 | No | 0.0075 |
| D20001C | 12 | 0.005 | No | 0.005 | No | 0.0075 |
| D30010 | 13 | 0.005 | No | 0.005 | No | 0.0075 |
| D30010A | 14 | 0.005 | No | 0.005 | No | 0.0075 |
| D40059 | 15 | 1.05 | No | 0.005 | No | 0.0075 |
| D40059A | 16 | 0.005 | No | 0.005 | No | 0.0075 |
| D40059B | 17 | 0.005 | No | 0.005 | No | 0.0075 |
| D60015 | 18 | 0.005 | No | 0.005 | No | 0.0075 |
| D60015A | 19 | 0.005 | No | 0.005 | No | 0.0075 |
| D70017 | 20 | 0.005 | No | 0.005 | No | 0.0075 |
| D70017A | 21 | 0.005 | No | 0.005 | No | 0.0075 |
| D80019 | 22 | 0.005 | No | 0.005 | No | 0.0075 |
| D80019A | 23 | 0.005 | No | 0.005 | No | 0.0075 |
| D90002 | 24 | 0.005 | No | 0.005 | No | 0.0075 |
| D90002A | 25 | 0.005 | No | 0.005 | No | 0.0075 |
| DA0001 | 26 | 0.005 | No | 0.005 | No | 0.0075 |
| DA0001A | 27 | 0.005 | No | 0.005 | No | 0.0075 |
| DB0001 | 28 | 0.005 | No | 0.005 | No | 0.0075 |
| DB0001A | 29 | 0.005 | No | 0.005 | No | 0.0075 |
| DC0001 | 30 | 0.005 | No | 0.005 | No | 0.0075 |
| DC0001A | 31 | 0.005 | No | 0.005 | No | 0.0075 |
| DC0001B | 32 | 0.005 | No | 0.005 | No | 0.0075 |
| DC0001C | 33 | 0.005 | No | 0.005 | No | 0.0075 |
| MT477 | 2(a) | 0.005 | No | 0.005 | No | 0.0075 |
| MT477A | 2(b) | 0.005 | Possible | 15.36 | No | 0.0075 |
| MT477B | 2(c) | 0.005 | No | 0.005 | No | 0.0075 |
| MT477C | 2(d) | 0.005 | No | 0.005 | No | 0.0075 |
| MT477D | 2(e) | 0.005 | No | 0.005 | No | 0.0075 |
| MT477E | 2(f) | 0.005 | No | 0.005 | No | 0.0075 |
| MT477F | 2(g) | 0.005 | No | 0.005 | No | 0.0075 |
| MT477-3N | 45 | 0.005 | No | 0.005 | No | 0.0075 |
| MT477-N5 | 40 | 0.005 | No | 0.005 | No | 0.0075 |
| MT477-N7 | 38 | 0.005 | No | 0.005 | No | 0.0075 |
| MT477-N1 | 36 | 0.005 | No | 0.005 | No | 0.0075 |
| MT477-N3 | 42 | 0.005 | No | 0.005 | No | 0.0075 |
| MT477-N4 | 41 | 0.005 | No | 0.005 | No | 0.0075 |

TABLE 4I-continued

| Molecule | Formula | Carcinogenicity (Potency) | Mutagenicity Probability | Mutagenicity Potency | Neurotoxicity (Prob,) | Neurotoxicity (Potency) |
|---|---|---|---|---|---|---|
| MT477-N2 | 43 | 0.005 | No | 0.005 | No | 0.0075 |
| MT477-3O | 44 | 0.005 | Possible | 15.26 | No | 0.0075 |
| MT477-N6 | 39 | 0.005 | No | 0.005 | No | 0.0075 |
| D60015A | 37 | 0.005 | No | 0.005 | No | 0.0075 |

TABLE 4J

| Molecule | Formula | Hematotoxicity (Prob,) | Cytotoxicity (microM) | Teratogenicity (Prob,) | Molecular Weight |
|---|---|---|---|---|---|
| D10000 | 5 | No | 2396.34 | No | 586.66 |
| D10000A | 6 | No | 1004.89 | No | 573.64 |
| D10000B | 7 | Possible | 832.66 | No | 599.57 |
| D10000C | 8 | No | 2257.22 | No | 606.56 |
| D20001 | 9 | No | 1973.24 | No | 608.19 |
| D20001A | 10 | Possible | 1864.11 | No | 620.11 |
| D20001B | 11 | Possible | 1787.53 | No | 643.06 |
| D20001C | 12 | Possible | 1656.84 | No | 641.57 |
| D30010 | 13 | No | 12953.87 | No | 630.76 |
| D30010A | 14 | Possible | 12284.28 | No | 642.68 |
| D40059 | 15 | No | 3763.76 | No | 641.33 |
| D40059A | 16 | No | 679.97 | No | 641.22 |
| D40059B | 17 | Possible | 3452.78 | No | 653.25 |
| D60015 | 18 | No | 655.3 | No | 640.76 |
| D60015A | 19 | No | 18154.73 | No | 694.85 |
| D70017 | 20 | No | 555.65 | No | 703.4 |
| D70017A | 21 | No | 1077.02 | No | 706.9 |
| D80019 | 22 | No | 1672.48 | No | 653.29 |
| D80019A | 23 | Possible | 1591.55 | No | 665.21 |
| D90002 | 24 | No | 771.82 | No | 644.75 |
| D90002A | 25 | Possible | 606.13 | No | 656.67 |
| DA0001 | 26 | No | 3230.74 | No | 693.31 |
| DA0001A | 27 | Possible | 2760.16 | No | 717.16 |
| DB0001 | 28 | No | 2725.75 | No | 666.83 |
| DB0001A | 29 | No | 5360.52 | No | 692.87 |
| DC0001 | 30 | No | 2014.07 | No | 527.61 |
| DC0001A | 31 | No | 2185.31 | No | 515.6 |
| DC0001B | 32 | No | 769.85 | No | 508.61 |
| DC0001C | 33 | Possible | 3381.5 | No | 574.46 |
| MT477 | 2(a) | Possible | 8215.64 | No | 717.68 |
| MT477A | 2(b) | Possible | 2618.84 | No | 769.76 |
| MT477B | 2(c) | Possible | 3910.38 | No | 730.7 |
| MT477C | 2(d) | Possible | 3280.87 | No | 717.68 |
| MT477D | 2(e) | Possible | 2997.18 | No | 701.68 |
| MT477E | 2(f) | Possible | 3878.41 | No | 717.68 |
| MT477F | 2(g) | Possible | 3524.87 | No | 688.66 |
| MT477-3N | 45 | Possible | 8167.18 | No | Possible |
| MT477-N5 | 40 | Possible | 7682.18 | No | Possible |
| MT477-N7 | 38 | Possible | 7284.55 | No | Possible |
| MT477-N1 | 36 | Possible | 8312.38 | No | Possible |
| MT477-N3 | 42 | Possible | 8037.90 | No | Possible |
| MT477-N4 | 41 | Possible | 9030.15 | No | Possible |
| MT477-N2 | 43 | Possible | 8215.64 | No | Possible |
| MT477-3O | 44 | No | 18154.73 | No | No |
| MT477-N6 | 39 | Possible | 8167.18 | No | Possible |
| D60015A | 37 | Possible | 7284.55 | No | Possible |

The examples set forth herein are exemplary and are not intended to limit the scope or spirit of the invention. Many embodiments of the MT477 family have been set forth herein; persons of ordinary skill in these arts will appreciate, after reading this disclosure, additional variations and alternatives that may be accomplished; such variations and alternative would therefore fall within the scope of this disclosure. Patents, patent applications, journal articles, and publications that have been referenced in this application are hereby incorporated by reference herein.

What is claimed is:

1. A method for treating a cancer selected from leukemia, non-small cell lung cancer, colon cancer, CNS cancer. melanoma, ovarian cancer, renal cancer, prostate cancer, breast cancer, and pancreatic cancer in a patient, comprising administering to said patient a therapeutically effective amount of a compound selected from

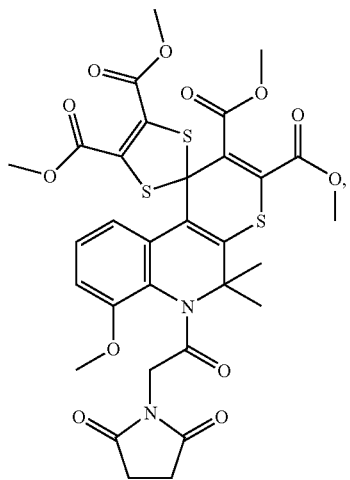

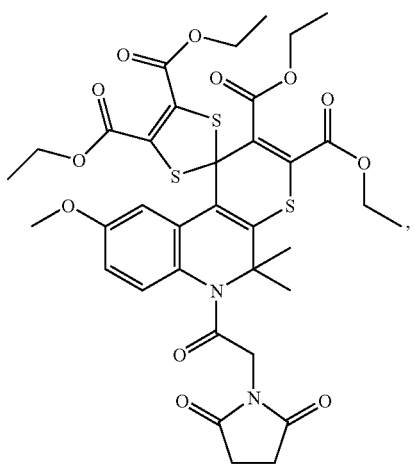

-continued
61
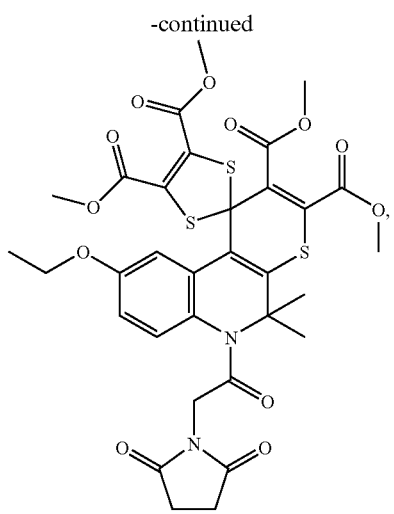
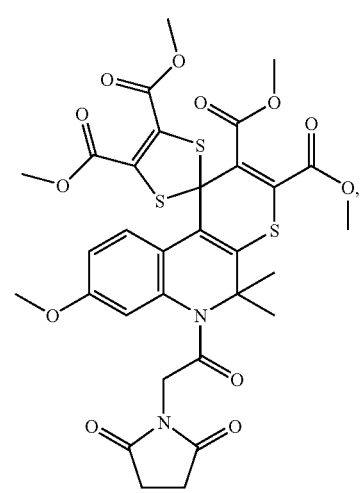
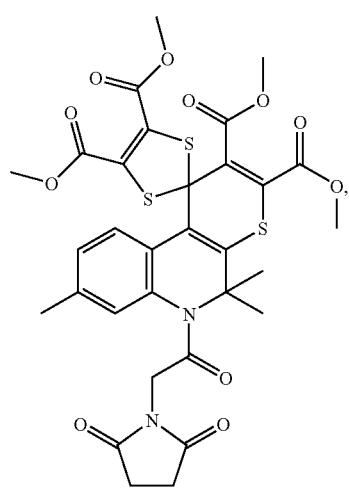
62
-continued
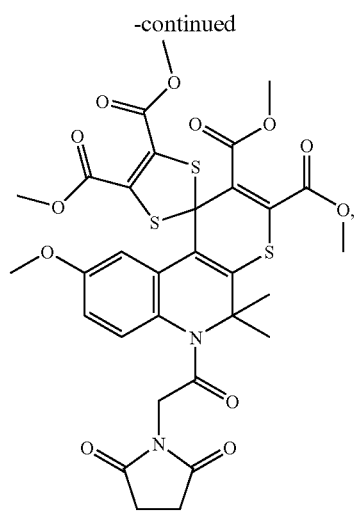
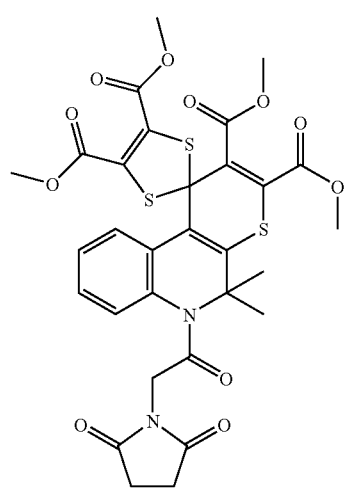
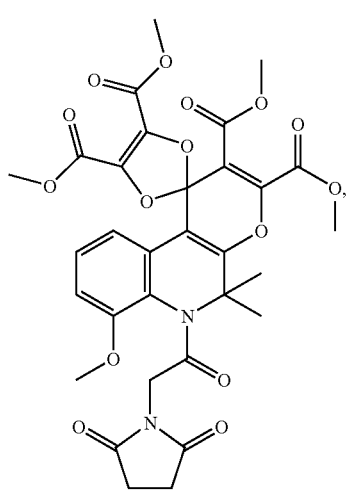

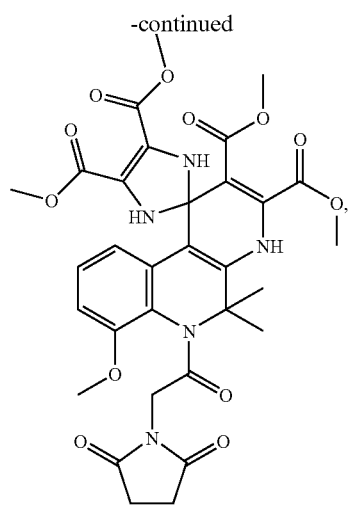

or a pharmaceutically acceptable salt thereof.

2. A method for treating a cancer selected from leukemia, non-small cell lung cancer, colon cancer, CNS cancer, melanoma, ovarian cancer, renal cancer, prostate cancer, breast cancer, and pancreatic cancer in a patient comprising administering to said patient a therapeutically effective amount of a compound having a structure

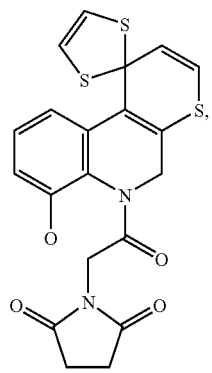

or a pharmaceutically acceptable salt thereof.

3. A pharmaceutical composition comprising a pharmaceutically acceptable carrier or diluent and a compound selected from

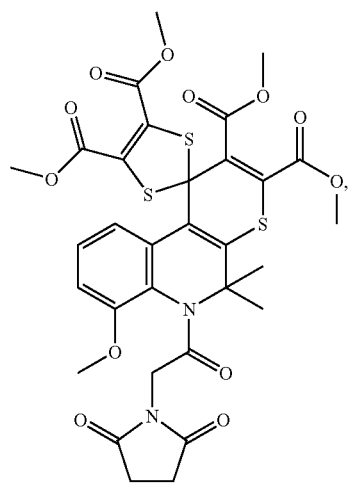

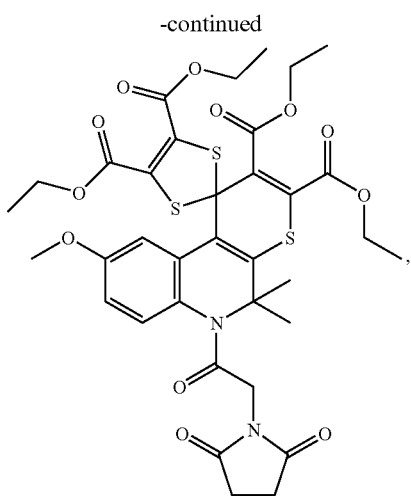

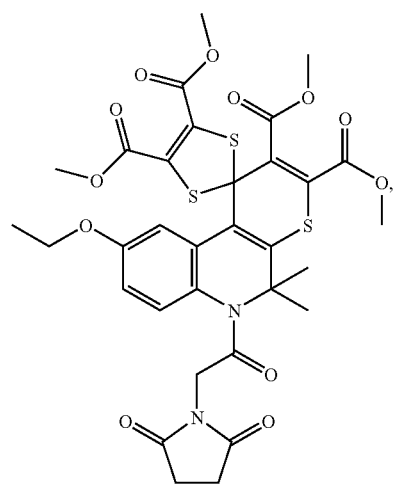

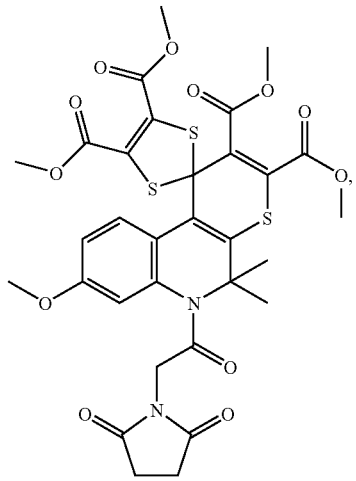

-continued
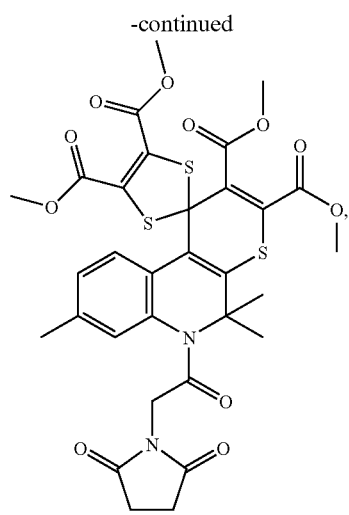
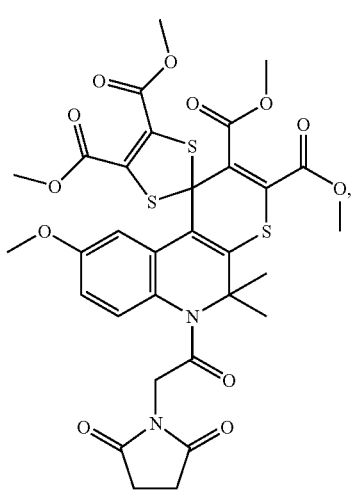
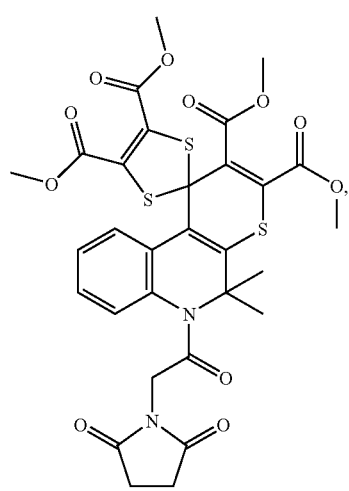
-continued
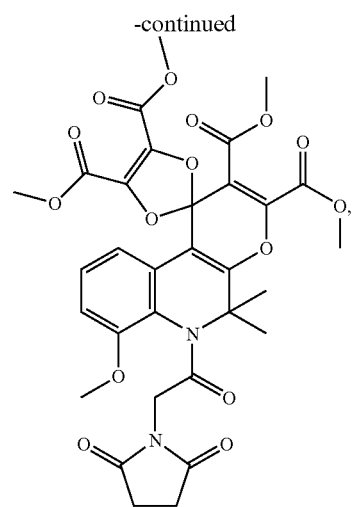
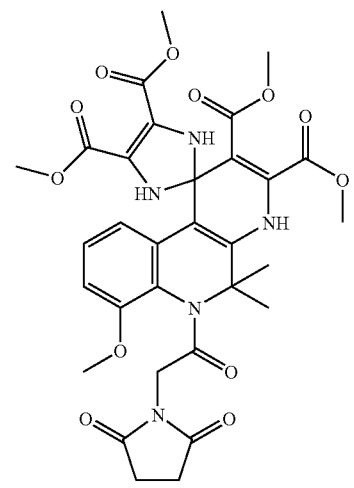
or a pharmaceutically acceptable salt thereof.
4. A pharmaceutical composition comprising a pharmaceutically acceptable carrier or diluent and a compound having a structure
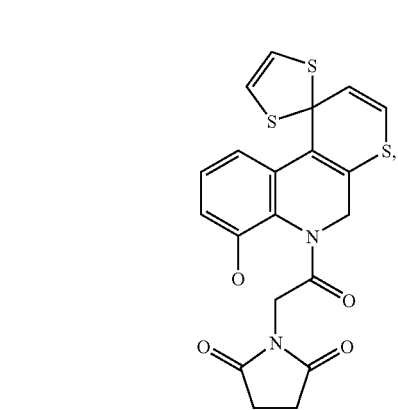
or a pharmaceutically acceptable salt thereof.

5. The pharmaceutical composition of claim 3, wherein the compound is:

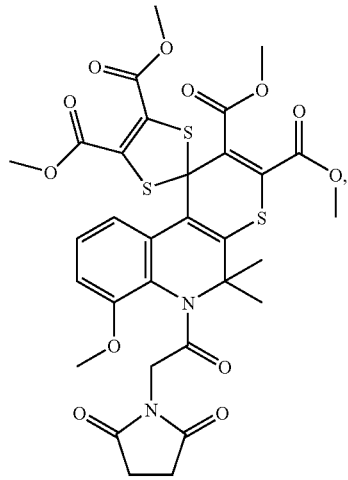

or a pharmaceutically acceptable salt thereof.

6. The method of claim 1, wherein the compound is:

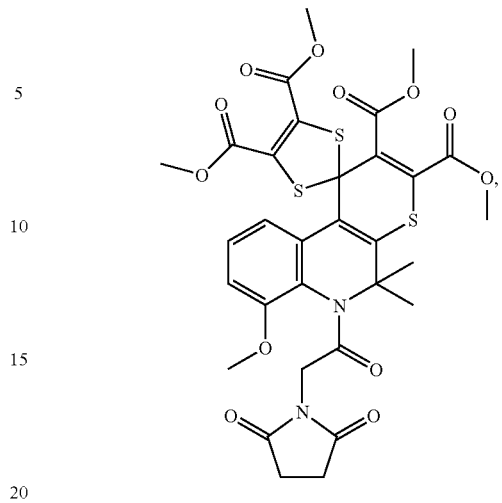

or a pharmaceutically acceptable salt thereof.

7. A method for treating a cancer selected from leukemia, non-small cell lung cancer, colon cancer, CNS cancer, melanoma, ovarian cancer, renal cancer, prostate cancer, breast cancer, and pancreatic cancer in a patient, comprising administering to said patient a pharmaceutical composition of claim 3, 4, or 5.

8. The method of any one of claims 1, 2, or 6, wherein the cancer is non-small cell lung cancer.

9. The method of any one of claims 1, 2, or 6, wherein the cancer is pancreatic cancer.

10. The method of claim 7, wherein the cancer is non-small cell lung cancer.

11. The method of claim 7, wherein the cancer is pancreatic cancer.

* * * * *